United States Patent
Ueno et al.

(10) Patent No.: US 10,442,843 B2
(45) Date of Patent: *Oct. 15, 2019

(54) METHOD FOR PRODUCING PROTEIN

(71) Applicant: NIPPI, INCORPORATED, Tokyo (JP)

(72) Inventors: Tomonori Ueno, Tokyo (JP); Yuki Taga, Tokyo (JP); Kiyoko Goto, Tokyo (JP); Yuko Kaku, Tokyo (JP)

(73) Assignee: NIPPI, INCORPORATED, Tokyo (JP)

( * ) Notice: Subject to any disclaimer, the term of this patent is extended or adjusted under 35 U.S.C. 154(b) by 14 days.

This patent is subject to a terminal disclaimer.

(21) Appl. No.: 15/685,053

(22) Filed: Aug. 24, 2017

(65) Prior Publication Data
US 2018/0118796 A1    May 3, 2018

Related U.S. Application Data

(63) Continuation of application No. 14/780,313, filed as application No. PCT/JP2014/058702 on Mar. 26, 2014, now Pat. No. 9,884,897.

(30) Foreign Application Priority Data

Mar. 26, 2013 (JP) .................. 2013-064357
Dec. 18, 2013 (JP) .................. 2013-261178

(51) Int. Cl.
*C07K 14/47* (2006.01)
*C12N 15/85* (2006.01)
*C12P 21/00* (2006.01)
*C12P 21/02* (2006.01)
*C12N 15/67* (2006.01)
*C07K 14/705* (2006.01)

(52) U.S. Cl.
CPC ........ *C07K 14/47* (2013.01); *C07K 14/70553* (2013.01); *C12N 15/67* (2013.01); *C12N 15/85* (2013.01); *C12P 21/00* (2013.01); *C12P 21/02* (2013.01)

(58) Field of Classification Search
CPC .......... C07K 14/47; C12N 15/85; C12P 21/00
See application file for complete search history.

(56) References Cited

U.S. PATENT DOCUMENTS

| 5,593,859 | A | 1/1997 | Prockop et al. |
| 8,232,377 | B2 | 7/2012 | Chiba et al. |
| 9,884,897 | B2 * | 2/2018 | Ueno ............... C12P 21/02 |
| 2006/0068434 | A1 | 3/2006 | Stoerker |
| 2006/0172416 | A1 | 8/2006 | Li et al. |
| 2014/0065620 | A1 | 3/2014 | Perez et al. |

FOREIGN PATENT DOCUMENTS

| JP | 2002507894 | 3/2002 |
| JP | 2013085498 | 5/2013 |
| WO | 1999/001565 | 1/1999 |
| WO | 2007/132949 | 11/2007 |
| WO | 2011/111829 | 9/2011 |

OTHER PUBLICATIONS

Champion-Arnaud P. et al. "The prespliceosome components SAP 49 and SAP 145 interact in a complex implicated in tethering U2 snRNP to the branch site," Genes Dev. Aug. 15, 1994;8(16):1974-83.
Cui XA, et al. "p180 promotes the ribosome-independent localization of a subset of mRNA to the endoplasmic reticulum," PLoS Biol. 2012; 10(5):e1001336(1-18).
Tanaka Y, et al. "Polycistronic expression and RNA-binding specifically of the C. elegans homologue of the spliceosome-associated protein SAP49," J. Biochem. Apr. 1997;121(4):739-45.
Ueno T, et al. "Regulation of polysome assembly on the endoplasmic reticulum by a coiled-coil protein, p180," Nucleic Acids Res. Apr. 2012;40(7):3006-17.
Ueno T, et al. "Enhancement of procollagen biosynthesis by p180 through augmented ribosome association on the endoplasmic reticulum in response to the stimulated secretion," J Biol Chem. Sep. 24, 2010;285(39):29941-50.
Telikicheria et al. 2012; Overexpression of ribosome binding protein 1 (RRBP1) in breast cancer. Clinical Proteomics 9:7.
Edvardsen et al. 1997; Effect of NCAM-trasnfection on growth and invasion of a human cancer cell line. APMIS 103:919-930.
Watanabe et al. 2007; Splicing factor 3b subunit 4 binds BMPR-1A and inhibits osteochondral cell differentiation. J. Bio. Chem. 282 (28): 20728-20738.
Mahmood et al. 2012; Western blot: technique, theory, and trouble shooting. N Am J. Med Sci 4(9): 429-434.

* cited by examiner

*Primary Examiner* — Karen Cochrane Carlson
(74) *Attorney, Agent, or Firm* — Robin L. Teskin; Baker, Donelson, Bearman, Caldwell & Berkowitz, PC

(57) ABSTRACT

It has been believed that promoting the assembly of polysomes composed of many ribosomes attached to mRNA is very effective for highly efficient protein synthesis. However, the mechanism for p180 protein's capability of promoting polysome formation has been yet to be elucidated. The inventors of the present application newly discovered SF3b4 protein as a protein that specifically interacts with the coiled-coil domain of p180 protein, a responsible region for its capability of promoting polysome formation, and which is capable of promoting mRNA localization to an endoplasmic reticulum (ER). The inventors also found that, in cells capable of highly expressing both p180 protein and a protein promoting mRNA localization to an endoplasmic reticulum (ER) (e.g., SF3b4 protein), the mRNA localization to the endoplasmic reticulum can be significantly elevated so that the secretory capacity in cultured cells can be enhanced. Further, the inventors demonstrated that when a particular nucleotide sequence is inserted into an expression plasmid, SF3b4 protein exhibiting protein expression enhancing ability can be localized onto the endoplasmic reticulum membrane, and the mRNA distribution in polysomes can be shifted towards heavier fractions, whereby the secretory capacity in cells can be enhanced.

11 Claims, 10 Drawing Sheets

Specification includes a Sequence Listing.

FIG. 4
A
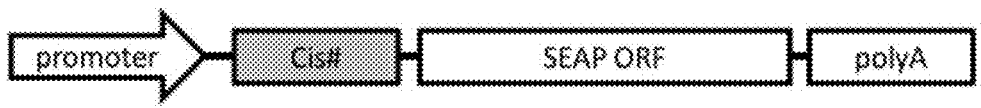
B
|  | SEAP activity, fold increase cis#1/control |
|---|---|
| CHO | 2.7 ± 0.2 |
| 3D5 | 3.2 ± 0.1 |
| 5g | 3.0 ± 0.2 |
| YA7 | 3.2 ± 0.1 |
C
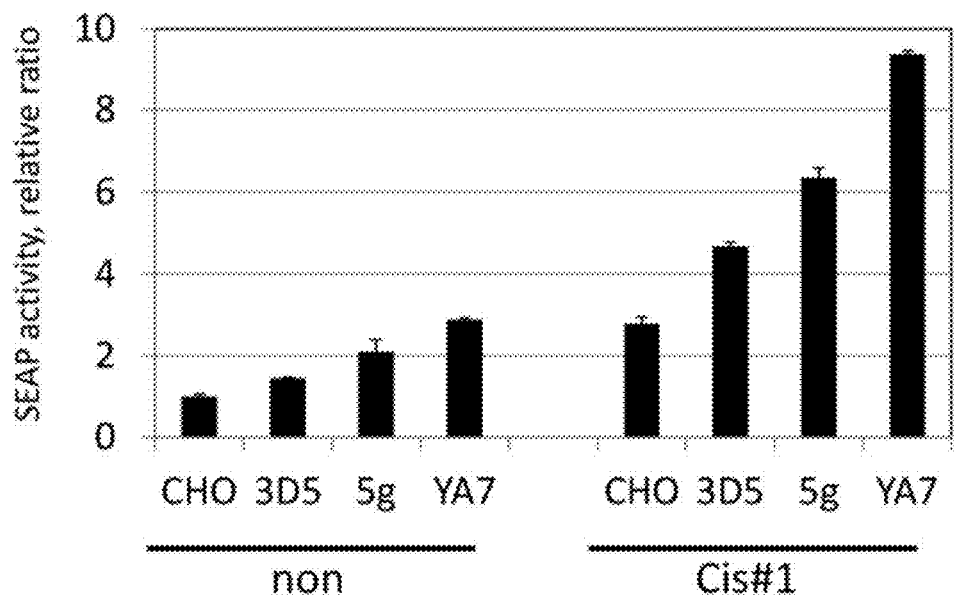

|     | COL1A1 procollagen secretion, relative ratio |
| --- | --- |
| CHO | 1 |
| 3D5 | 1.6 ± 0.6 |
| YA7 | 20.2 ± 4.9 |

B

|     | cis#1 | COL1A1 homotrimer secretion, relative ratio |
| --- | --- | --- |
| CHO |   | 1 |
| 3D5 | - | 1.5 |
| YA7 |   | 2.1 |
| CHO |   | 1.9 |
| 3D5 | + | 1.7 |
| YA7 |   | 3.3 |

C

|     | COL2A1 homotrimer secretion, relative ratio |
| --- | --- |
| CHO | 1 |
| 3D5 | 1.4 |
| YA7 | 1.9 |

D

|     | COL3A1 homotrimer secretion, relative ratio |
| --- | --- |
| CHO | 1 |
| YA7 | 3.7 |

FIG. 9

A n=1 TCGTCGGAGGACGGGAGTTTCTCCT (SEQ ID NO. 40)
n=2 TCGTCGGAGAGACGGGAGTTTCTCCT (SEQ ID NO. 41)
n=3 TCGTCGGAGCAGACGGGAGTTTCTCCT (cis#3) (SEQ ID NO. 7)
n=4 TCGTCGGAGCAGaACGGGAGTTTCTCCT (SEQ ID NO. 42)
n=5 TCGTCGGAGCAGaaACGGGAGTTTCTCCT (SEQ ID NO. 43)
n=6 TCGTCGGAGCAGaaaACGGGAGTTTCTCCT (SEQ ID NO. 44)
n=7 TCGTCGGAGCAGaaaaACGGGAGTTTCTCCT (SEQ ID NO. 45)
n=8 TCGTCGGAGCAGaaaaaACGGGAGTTTCTCCT (SEQ ID NO. 46)
n=9 TCGTCGGAGCAGaaaaaaACGGGAGTTTCTCCT (SEQ ID NO. 47)
Motif delete TCGTCG    CAG           GGAGTTTCTCCT (SEQ ID NO. 48)

B

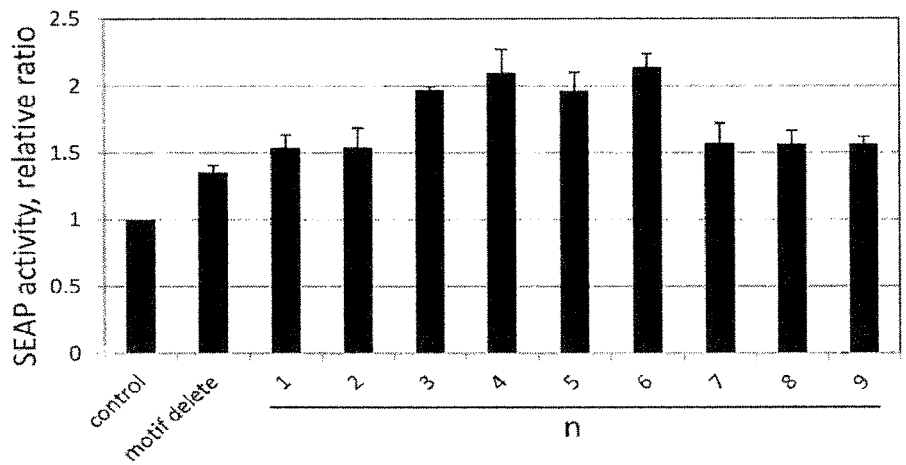

FIG. 10A

```
              GAN₁XXX ACN₂
     N₂=G  TCGTCGGAGCAGACGGGAGTTTCTCCT  (cis#3)
     N₂=A  TCGTCGGAGCAGACAGGAGTTTCTCCT
     N₂=C  TCGTCGGAGCAGACCGGAGTTTCTCCT
     N₂=T  TCGTCGGAGCAGACTGGAGTTTCTCCT
 Motif in A  AAAAAAGAGAAAACGAAAAAAAAAAAA
       allA  AAAAAAAAAAAAAAAAAAAAAAAAAAA
     N₁=G  CCCCCCGAGCCCACACCCCCCCCCCCC
     N₁=A  CCCCCCGAACCCACACCCCCCCCCCCC
     N₁=C  CCCCCCGACCCCACACCCCCCCCCCCC
     N₁=T  CCCCCCGATCCCACACCCCCCCCCCCC
       all C  CCCCCCCCCCCCCCCCCCCCCCCCCCC
```

FIG. 10B

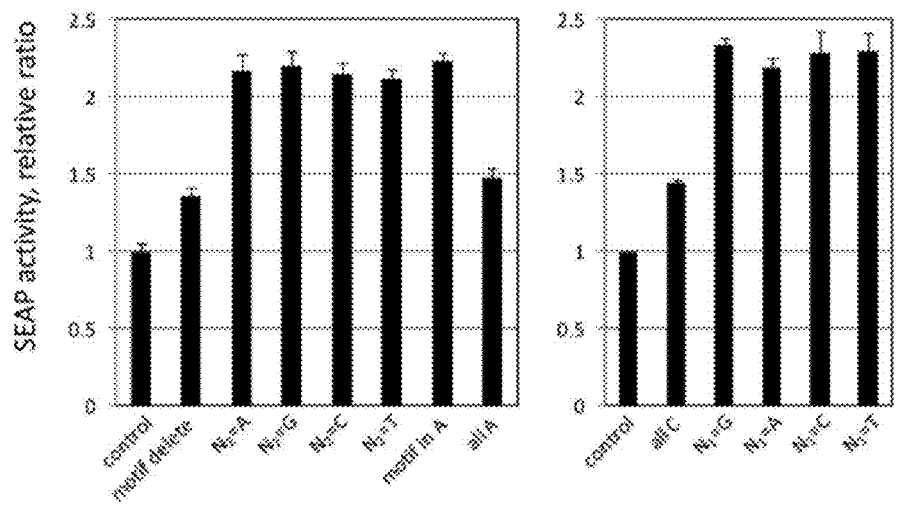

|  | SF3b4 expression (relative ratio) | COL1A1 secretion (relative ratio) |
|---|---|---|
| Control cells | 1 | 1 |
| SF3b4 knockdown cells | 0.2±0.1 | 0.1±0.1 |

METHOD FOR PRODUCING PROTEIN

This application is a continuation of U.S. National Phase application Ser. No. 14/780,313 which has a 371(c) date of Sep. 25, 2015, now U.S. Pat. No. 9,884,897, which is based on International Application No. PCT/JP2014/058702 filed Mar. 26, 2014 (published as WO2014/157429 on Oct. 2, 2014) which claims the benefit of Japanese Applications 2013-064357 filed Mar. 26, 2013 and 2013-261178 filed Dec. 18, 2013, each of which is hereby incorporated by reference in its entirety.

SEQUENCE LISTING

This application includes as part of its disclosure a biological sequence listing text file which is being submitted via EFS-Web. Said biological sequence listing is contained in the file named "4941601001.txt" having a size of 57,570 bytes that was created Feb. 4, 2019, which is hereby incorporated by reference in its entirety.

TECHNICAL FIELD

The present application relates to a recombinant cell for enhancing protein expression from an exogenous gene in recombinant cells, as well as an invention using such a cell. More specifically, this application relates to providing a cell having enhanced expression of p180 protein and/or SF3b4 protein, or a method for enhancing a synthetic or secretory capacity of a protein as a product of interest and consequently producing a protein, with the use of a cell having such characteristics. The method for enhancing a synthetic or secretory capacity of a protein as a product of interest and consequently producing a protein, with the use of a cell having such characteristics, is also characterized by using a cis-element in a vector for expressing the protein as a product of interest.

BACKGROUND ART

In the field of biotechnological pharmaceuticals developed by applying genetic recombination technologies, particularly the market for antibody pharmaceuticals has grown rapidly in recent years while there have been raised concerns about their loading on medical expenses; so there has always been a demand for developing a technique for producing biotechnological pharmaceuticals that enable more efficient protein production and are more low-cost than conventional ones.

Examples of hosts that have been used for protein production using genetic recombination technologies include animal cells, yeast, and *Escherichia coli. E. coli* and the like are capable of producing a protein as a product of interest with low costs, but are unfit for glycoprotein production because no post-translational modification such as sugar-chain modification can be achieved in such microorganisms. In addition, *E. coli* has a tendency to form an inclusion body containing a produced protein, and thus has a disadvantage in that, in order to obtain a protein as a product of interest, a solubilization process is further required after synthesis, thereby causing heavy workload.

Particularly in the case of glycoproteins such as antibodies, an added sugar chain has an influence on the water solubility of a protein as a product of interest, its resistance to a protease, its tissue-targeting capability, and its biological activity; thus, there has been a need for production technologies using animal cells from higher eukaryotes, and these technologies have advanced considerably in recent years. Under these circumstances, many current antibody pharmaceuticals are produced using Chinese hamster ovary (CHO) cells, and optimizing production processes for such pharmaceuticals is still an important challenge.

Proteins secreted extracellularly from eukaryotic cells including mammalian cells are synthesized in the endoplasmic reticulum which is intracellular organelle divided by endomembranes. The endoplasmic reticulum is broadly classified into the following two types: a rough endoplasmic reticulum studded on its surface with ribosomes which are machines for protein synthesis composed of a RNA-protein macrocomplex, and a smooth endoplasmic reticulum with no ribosomes, but the detailed mechanism of formation of the rough endoplasmic reticulum has been yet to be elucidated.

In the living body, there are professional secretory cells specialized in secreting particular proteins, and these professional secretory cells have highly developed rough endoplasmic reticulum which are considered to enable highly efficient protein production. Examples of such professional secretory cells include fibroblasts secreting collagen, and pancreatic exocrine secretory cells secreting a group of digestive enzymes. As compared to those professional secretory cells, rough endoplasmic reticulum such as CHO cells and HEK293 cells, which are now often used for genetically engineered protein production, are problematic in that they are present only in a very small amount and are inferior in secretory activity.

In the process of production of biotechnological pharmaceuticals using genetic recombination technologies, the genes of a protein as a product of interest are under the control of a promoter showing high transcription activity in an expression vector, and are presumed to express their mRNA at a high level. However, even under these conditions, the mRNA level is often not correlated with the expressed protein amount per se, and one of the factors for this may be due to low efficiency of mRNA translation on the endoplasmic reticulum membranes.

These observation suggest that there may be room for further enhancement of the protein synthetic capacity in the aforementioned cells that are now widely used for genetically engineered protein production, if mRNA can be provided in a more appropriate manner to be used to the machines for translation on the endoplasmic reticulum membranes like in the case of fibroblasts.

It is known that fibroblasts permanently secreting collagen constantly express a high level of collagen protein-encoding mRNAs, the majority of which is detected on the endoplasmic reticulum, a place of biosynthesis of the secretory proteins (Non-patent Literature 1). However, its more localization of the collagen mRNA on the endoplasmic reticulum is not sufficient to activate collagen synthesis, but the formation of a polysome having high translation efficiency is also needed for activated synthesis.

The previous analyses made by the present inventors revealed that the mRNAs for some types of proteins, including collagen genes, have a tendency to form a polysome in which multiple ribosomes, machines for protein synthesis are associated to each other (Patent Literature 1, Non-patent Literature 2). This finding led to the conjecture that the reason why, in the process of production of biotechnological pharmaceuticals using genetic recombination technologies, gene transcripts encoding a protein of interest are expressed at a high level and nevertheless the protein is synthesized or secreted only in a small amount, it may be because in used cells, mRNA is not provided to the machines for translation on the endoplasmic reticulum membranes in an easy-to-use form.

CITATION LIST

Non-Patent Literatures

Non-patent Literature 1: Ueno, T., et al., (2010). J Biol Chem 285 (39), 29941-50.

Non-patent Literature 2: Ueno, T., et al., (2012). Regulation of polysome assembly on the endoplasmic reticulum by a coiled-coil protein, p180. Nucleic Acids Res.

Patent Literature

Patent Literature 1: Japanese Patent Application Publication No. JP 2011-227462

SUMMARY OF INVENTION

Technical Problem

For the purpose of protein synthesis on the endoplasmic reticulum, the localization of mRNA to the endoplasmic reticulum (polysome formation) is indispensable. Further, it has been believed that promoting the formation of polysomes composed of many ribosomes attached to mRNA is very effective for highly efficient protein synthesis. However, the mechanism for p180 protein's capability of promoting polysome formation has been yet to be elucidated.

Solution to Problem

The inventors of the subject application have made in-depth analysis, and as a result newly discovered SF3b4 (splicing factor 3B subunit 4) protein as a protein that specifically interacts with the coiled-coil domain of p180 protein, a responsible region for promotion of polysome formation (Non-patent Literature 2), to thereby promote mRNA localization to the endoplasmic reticulum (ER). Further, the inventors created cells capable of highly expressing both SF3b4 protein and p180 protein, and as a result found that, in those cells having such a characteristic, the mRNA localization to the endoplasmic reticulum can be significantly elevated so that the secretory capacity in cultured cells can be enhanced. Thus, the inventors have completed the present invention.

The present inventors demonstrated that there can be provided a recombinant cell having enhanced intracellular expression of the full length or a portion of p180 protein and enhanced intracellular expression of a protein promoting mRNA localization to an endoplasmic reticulum (ER), and having enhanced intracellular synthetic or secretory capacity of a protein as a product of interest.

The present inventors also demonstrated that, in the second mode of the present invention, there can be provided a method in which, in a recombinant cell having enhanced expression of the full length or a portion of p180 protein and enhanced expression of a protein promoting mRNA localization to an endoplasmic reticulum (ER), a nucleic acid molecule encoding a protein as a product of interest is transformed or production of the protein as a product of interest is increased, whereby biosynthetic or secretory capacity of the protein as a product of interest is enhanced and consequently the protein as a product of interest is produced.

It was demonstrated that the present invention can solve the aforementioned problems by providing such a characteristic recombinant cell, or by using said characteristic recombinant cell and enhancing the synthetic or secretory capacity of a protein as a product of interest.

[1] A recombinant cell having enhanced intracellular expression of the full length or a portion of p180 protein, or a protein promoting mRNA localization to an endoplasmic reticulum (ER), or both of said proteins, and having enhanced intracellular synthetic or secretory capacity of a protein as a product of interest.

[2] The recombinant cell as set forth in [1], wherein the p180 protein is selected from the group consisting of:

(a) a protein that consists of an amino acid sequence with at least 70% sequence identity to the amino acid sequence (SEQ ID NO: 2) of human-derived p180 protein, and which has a capability of promoting polysome formation on an intracellular endoplasmic reticulum membrane;

(b) a protein that consists of an amino acid sequence derived from the amino acid sequence (SEQ ID NO: 2) of the human-derived p180 protein by deletion, substitution, or addition of one or more amino acids, and which has a capability of promoting polysome formation on the intracellular endoplasmic reticulum membrane;

(c) a protein that consists of an amino acid sequence specified by a nucleotide sequence with at least 70% sequence identity to the nucleotide sequence (SEQ ID NO: 1) of a gene encoding the human-derived p180 protein, and which has a capability of promoting polysome formation on the intracellular endoplasmic reticulum membrane;

(d) a protein that consists of an amino acid sequence specified by a nucleotide sequence derived from the nucleotide sequence (SEQ ID NO: 1) of the gene encoding the human-derived p180 protein by deletion, substitution, or addition of one or more nucleotides, and which has a capability of promoting polysome formation on the intracellular endoplasmic reticulum membrane; and (e) a protein that consists of an amino acid sequence specified by a nucleotide sequence hybridizable under stringent conditions with a nucleotide sequence complementary to the nucleotide sequence (SEQ ID NO: 1) of the gene encoding the human-derived p180 protein, and which has a capability of promoting polysome formation on the intracellular endoplasmic reticulum membrane.

[3] The recombinant cell as set forth in [1] or [2], wherein the p180 protein is derived from a mammalian animal.

[4] The recombinant cell as set forth in [3], wherein the full length or the portion of the mammalian p180 protein is the human p180 protein (SEQ ID NO: 2), murine p180 protein (GenBank Accession No. NP_077243), rat p180 protein (GenBank Accession No. XP_230637), Chinese hamster p180 protein (GenBank Accession No. XM_003496471), canine p180 protein (GenBank Accession No. NP_001003179), equine p180 protein (GenBank Accession No. XP_001915027), simian p180 protein (GenBank Accession No. XP_002798281), chimpanzee p180 protein (GenBank Accession No. XP_514527), porcine p180 protein (GenBank Accession No. XP_001926148), or a portion thereof.

[5] The recombinant cell as set forth in any one of [1] to [4], wherein the portion of the p180 protein is selected from: a portion comprising an amino acid sequence corresponding to a region consisting of the amino acids at positions 27 to 157 of a protein having the amino acid sequence of SEQ ID NO: 2 (human p180 protein); a portion comprising an amino acid sequence corresponding to a region consisting of the amino acids at positions 623 to 737 of said protein; a portion comprising an amino acid sequence corresponding to a region consisting of the amino acids at positions 738 to 944 of said protein; and a portion comprising an amino acid sequence corresponding to a region consisting of the amino acids at positions 945 to 1540 of said protein.

[6] The recombinant cell as set forth in any one of [1] to [5], wherein the protein promoting mRNA localization to the endoplasmic reticulum (ER) is selected from the group consisting of the full length or a portion of splicing factor 3B subunit 4 (SF3b4) protein (the full-length amino acid sequence 424 AA of SEQ ID NO: 4; RRM1 consisting of 13 to 91 AA of SEQ ID NO: 4; and RRM2 consisting of 100 of SEQ ID NO: 4).

[7] The recombinant cell as set forth in [6], wherein the SF3b4 protein is selected from the group consisting of:
 (i) a protein that consists of an amino acid sequence with at least 70% sequence identity to the amino acid sequence (SEQ ID NO: 4) of human-derived SF3b4 protein, and which has a capability of promoting mRNA localization to the endoplasmic reticulum;
 (ii) a protein that consists of an amino acid sequence derived from the amino acid sequence (SEQ ID NO: 4) of the human-derived SF3b4 protein by deletion, substitution, or addition of one or more amino acids, and which has a capability of promoting mRNA localization to the endoplasmic reticulum;
 (iii) a protein that consists of an amino acid sequence specified by a nucleotide sequence with at least 70% sequence identity to the nucleotide sequence (SEQ ID NO: 3) of a gene encoding the human-derived SF3b4 protein, and which has a capability of promoting mRNA localization to the endoplasmic reticulum;
 (iv) a protein that consists of an amino acid sequence specified by a nucleotide sequence derived from the nucleotide sequence (SEQ ID NO: 3) of the gene encoding the human-derived SF3b4 protein by deletion, substitution, or addition of one or more nucleotides, and which has a capability of promoting mRNA localization to the endoplasmic reticulum; and
 (v) a protein that consists of an amino acid sequence specified by a nucleotide sequence hybridizable under stringent conditions with a nucleotide sequence complementary to the nucleotide sequence (SEQ ID NO: 3) of the gene encoding the human-derived SF3b4 protein, and which has a capability of promoting mRNA localization to the endoplasmic reticulum.

[8] The recombinant cell as set forth in [6] or [7], wherein the SF3b4 protein is derived from a mammalian animal.

[9] The recombinant cell as set forth in [8], wherein the full length or the portion of mammalian SF3b4 protein is the human SF3b4 protein (SEQ ID NO: 4), murine SF3b4 protein (GenBank Accession No. NP_694693.1), rat SF3b4 protein (GenBank Accession No. NP_001011951.1), Chinese hamster SF3b4 protein (GenBank Accession No. XP_003498680.1), canine SF3b4 protein (GenBank Accession No. XP_540295.3), equine SF3b4 protein (GenBank Accession No. XP_001488649.2), simian SF3b4 protein (GenBank Accession No. NP_001097793.1), chimpanzee SF3b4 protein (GenBank Accession No. XP_513768.2), porcine SF3b4 protein (GenBank Accession No. XP_001926524.1), or a portion thereof.

[10] The recombinant cell as set forth in any one of [1] to [9], wherein the synthetic or secretory capacity of the protein as a product of interest is enhanced by transforming a nucleic acid molecule encoding the protein as a product of interest or increasing production of the protein as a product of interest.

[11] A cell line designated by Accession No. NITE BP-01753 (CHO 3D5), Accession No. NITE BP-1535 (CHO YA7), or Accession No. NITE ABP-01811 (CHO 1B2).

[12] A method for producing a protein as a product of interest, wherein, in a recombinant cell having enhanced expression of the full length or a portion of p180 protein, a protein promoting mRNA localization to an endoplasmic reticulum (ER), or both of said proteins, a nucleic acid molecule encoding the protein as a product of interest is transformed or production of the protein as a product of interest is increased, whereby the protein as a product of interest is produced.

[13] The method as set forth in [12], wherein the p180 protein is derived from a mammalian animal.

[14] The method as set forth in [13], wherein the full length or the portion of the mammalian p180 protein is human p180 protein (SEQ ID NO: 2), murine p180 protein (GenBank Accession No. NP_077243), rat p180 protein (GenBank Accession No. XP_230637), Chinese hamster p180 protein (GenBank Accession No. XM_003496471), canine p180 protein (GenBank Accession No. NP_001003179), equine p180 protein (GenBank Accession No. XP_001915027), simian p180 protein (GenBank Accession No. XP_002798281), chimpanzee p180 protein (GenBank Accession No. XP_514527), porcine p180 protein (GenBank Accession No. XP_001926148), or a portion thereof.

[15] The method as set forth in [13] or [14], wherein the portion of the mammalian p180 protein is selected from: a portion comprising a region consisting of the amino acids at positions 27 to 157 of a protein having the amino acid sequence of SEQ ID NO: 2 (human p180 protein); a portion comprising a region consisting of the amino acids at positions 623 to 737 of said protein; a portion comprising a region consisting of the amino acids at positions 738 to 944 of said protein; and a portion comprising a region consisting of the amino acids at positions 945 to 1540 of said protein.

[16] The method as set forth in any one of [12] to [15], wherein the protein promoting mRNA localization to the endoplasmic reticulum (ER) is selected from the group consisting of the full length or a portion of splicing factor 3B subunit 4 (SF3b4) protein (the full-length amino acid sequence 424 AA of SEQ ID NO: 4; RRM1 consisting of 13 to 91 AA of SEQ ID NO: 4; and RRM2 consisting of 100 of SEQ ID NO: 4).

[17] The method as set forth in [16], wherein the SF3b4 protein is derived from a mammalian animal.

[18] The method as set forth in [17], wherein the full length or the portion of mammalian SF3b4 protein is the human SF3b4 protein (SEQ ID NO: 4), murine SF3b4 protein (GenBank Accession No. NP_694693.1), rat SF3b4 protein (GenBank Accession No. NP_001011951.1), Chinese hamster SF3b4 protein (GenBank Accession No. XP_003498680.1), canine SF3b4 protein (GenBank Accession No. XP_540295.3), equine SF3b4 protein (GenBank Accession No. XP_001488649.2), simian SF3b4 protein (GenBank Accession No. NP_001097793.1), chimpanzee SF3b4 protein (GenBank Accession No. XP_513768.2), porcine SF3b4 protein (GenBank Accession No. XP_001926524.1), or a portion thereof.

[19] The method as set forth in any one of [12] to [18], wherein the recombinant cell is a cell line designated by Accession No. NITE BP-01753 (CHO 3D5), Accession No. NITE BP-1535 (CHO YA7), or Accession No. NITE ABP-01811 (CHO 1B2).

[20] The method as set forth in any one of [12] to [19], wherein the protein as a product of interest is a glycoprotein.

[21] The method as set forth in [20], wherein the protein as a product of interest is a collagen, a fibronectin, or an antibody.

[22] A method for increasing an amount of a protein as a product of interest to be expressed in a cell as an expression system, wherein, in an expression unit for expressing the protein as a product of interest, a cic-element to be recognized/bound (or interacted with) by an RNA-binding protein is inserted, downstream of a promoter and upstream of the start codon in the nucleotide sequence of a DNA encoding the protein as a product of interest, whereby the amount of the protein as a product of interest to be expressed in the cell as an expression system is increased.

[23] The method as set forth in [22], wherein the cis-element is to be recognized/bound (or interacted with) by an RNA recognition motif (RRM)-type RNA-binding protein.

[24] The method as set forth in [23], wherein the cis-element is to be recognized/bound (or interacted with) by an RNA recognition motif (RRM) of the SF3b4 protein.

[25] The method as set forth in any one of [22] to [24], wherein the cis-element has a nucleotide sequence containing one or more 9mer to 12mer sequence motifs GAN-$(X)_n$-ACN$_2$ (n=3 to 6) (N$_1$ and N$_2$ can be independently any of the nucleotides A, T, C and G).

[26] The method as set forth in [25], wherein the cis-element has a nucleotide sequence containing one or more 9mer to 12mer sequence motifs (GAG-$(X)_n$-ACV (n=3 to 6) (V represents A, G or C), SEQ ID NOs: 17 to 20).

[27] The method as set forth in any one of [22] to [26], wherein the nucleotide sequence of the cis-element is a sequence selected from the group consisting of: a sequence derived from the nucleotide sequence of the 5' untranslated region of a type I collagen gene; a sequence derived from the nucleotide sequence of the 5' untranslated region of a fibronectin gene; a sequence derived from the nucleotide sequence of the 5' untranslated region of the matrix metalloproteinase 14 (MMP14) gene; a sequence derived from the nucleotide sequence of the 5' untranslated region of the prolyl 4-hydroxylase A2 (P4HA2) gene; and a sequence derived from the nucleotide sequence of the 5' untranslated region of the prolyl 4-hydroxylase A1 (P4HA1) gene.

[28] The method as set forth in any one of [22] to [27], wherein the nucleotide sequence of the cis-element is any sequence selected from the group consisting of the full length of SEQ ID NO: 5 or the full length of SEQ ID NO: 7, and the nucleotides at positions 1 to 102, positions 1 to 78, positions 1 to 60, positions 61 to 126, positions 16 to 57, positions 79 to 126, positions 103 to 126, positions 58 to 78, positions 51 to 78, positions 1 to 27, and positions 70 to 78 of SEQ ID NO: 5.

[29] The method as set forth in any one of [22] to [28], wherein the cell as an expression system is an intact host cell, a cell having enhanced expression of the full length or a portion of p180 protein, a cell having enhanced expression of the full length or a portion of SF3b4 protein, or a cell having enhanced expression of both of said proteins.

[30] A medicinal composition for suppressing collagen synthesis and preventing the alveolar epithelium and aggravation of fibrosis due to abnormal collagen through functional inhibition or expression suppression of SF3b4.

Advantageous Effects of Invention

It was found that, by means of using the recombinant cell of the present invention which has enhanced expression of the full length or a portion of p180 protein and/or a protein promoting mRNA localization to the endoplasmic reticulum (ER) (e.g., the full length or a portion of SF3b4 protein), as well as transforming a DNA encoding a protein as a product of interest, a synthetic or secretory capacity of the protein as a product of interest is dramatically enhanced, and consequently the protein as a product of interest is produced efficiently. It is also demonstrated that when a cis-element is added into an expression unit, SF3b4 protein that exhibits protein expression enhancing ability can be localized onto an endoplasmic reticulum, and the mRNA distribution in polysomes can be shifted towards heavier fractions, whereby the secretory capacity in the cells can be enhanced.

BRIEF DESCRIPTION OF DRAWINGS

FIGS. 4A-C shows a schematic diagram of a position for insertion of a cis-element-containing expression vector (FIG. 4A), and the results of evaluating cis-element's secretion activation capability (FIG. 4B and FIG. 4C).

FIG. 5 shows variations in protein secretory activity in the cases where collagens were expressed.

FIG. 9 shows that an example of the motif in a cis-element is GAG-$(X)_n$-ACN$_2$ (n=3 to 6) (A), and also shows a diagram for evaluating various elements for SEAP secretory activity (B).

FIG. 10 shows an investigation of the influences of substitutions, deletions, or insertions of nucleotides in the motif GAN$_1$-$(X)_N$-ACN$_2$ on the motif activity (FIG. 10A and FIG. 10B).

DESCRIPTION OF EMBODIMENTS

Figure 1:
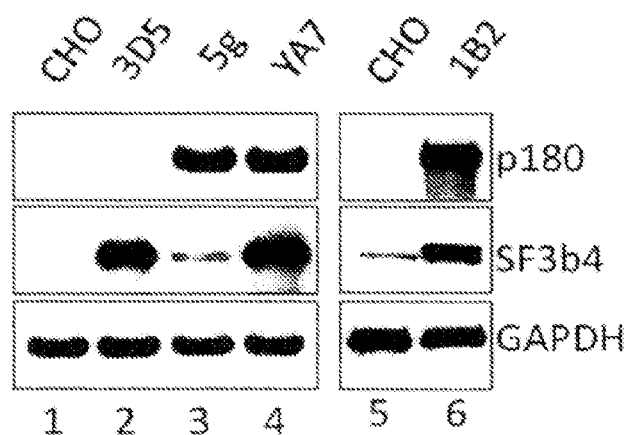
FIG. 1 shows the results of Western blotting analysis of the different types of cells prepared in Example 1 (CHO cells, CHO 3D5 cells, CHO 5 g cells, and CHO YA7 cells) for intracellular expression of p180 protein as well as SF3b4 protein, a protein promoting mRNA localization to an endoplasmic reticulum (ER).

The present inventors demonstrated that, in the first mode of the present invention, there can be provided a recombinant cell having enhanced intracellular expression of the full length or a portion of p180 protein and/or the full length or a portion of splicing factor 3B subunit 4 (SF3b4) protein, and having enhanced intracellular synthetic or secretory capacity of a protein as a product of interest.

In this mode of the present invention, the full length or a portion of p180 protein and/or the full length or a portion of SF3b4 protein are/is caused to be expressed in a cell, thereby making it possible to promote polysome formation on an intracellular endoplasmic reticulum, which is involved by mRNA, an expression product of a nucleic acid molecule encoding a protein as a product of interest. As referred to herein, the polysome refers to a complex in which multiple ribosomes on the intracellular endoplasmic reticulum are bound to one mRNA molecule. Such up-regulated polysome formation results in an enhancement of a biosynthetic or secretory capacity of a protein as a product of interest, thereby enabling production of the protein.

The aforementioned recombinant cell of the present invention is firstly characterized by having enhanced intracellular expression of the full length or a portion of p180 protein, particularly mammalian p180 protein. The p180 protein refers to an essential endoplasmic reticulum membrane protein which is abundantly expressed in secretory tissues and capable of promoting polysome formation.

In this connection, it is known that as compared to human p180 protein (GenBank Accession No. AB287347), murine p180 protein has 87% similarity in amino acid sequence, rat p180 protein has 87% similarity, Chinese hamster p180 protein has 88% similarity, canine p180 protein has 91% similarity, equine p180 protein has 89% similarity, simian p180 protein has 91-92% similarity, chimpanzee p180 protein has 98% similarity, and porcine p180 protein has 86% similarity. It is reported that the amino acid identities of all mammalian p180 proteins fall within a range not lower than 84%, and that even those of the p180 proteins of other living organisms fall within a range not lower than 76%.

TABLE 1

Sequence homologies of p180 of various species to human p180

| Organism | Classification | | Protein similarity to human (%): amino acid | Gene identity to human (%): nucleotide | Gene ID |
|---|---|---|---|---|---|
| Pan paniscus | chimpanzee | Mammalia | 98 | 98 | XM_003810595 |
| Mus musculus | mouse | Mammalia | 87 | 75 | NM_024281 |
| Bos mutus | yak | Mammalia | 38 | 78 | XM_005904566 |
| Bos taurus | cow | Mammalia | 87 | 74 | XM_003582930 |
| Canis familiaris | dog | Mammalia | 91 | 84 | NM_001003179 |
| Monodelphis domestica | oppossum | Mammalia | 83 | 68 | XM_001382073 |
| Pongo abelii | orangutan | Mammalia | 92 | 85 | XM_003779288 |
| Macaca mulatta | monkey | Mammalia | 91 | 85 | XM_001086541 |
| Macaca fascicularis | monkey | Mammalia | 92 | 85 | XM_005568285 |
| Cricetulus griseus | Chinese hamster | Mammalia | 88 | 78 | XM_003496471 |
| Jaculus jaculus | rodent | Mammalia | 86 | 76 | XM_004668728 |
| Otolemur garnettii | galago | Mammalia | 90 | 79 | XM_003801321 |
| Spermophilus tridecemlineatus | gopher | Mammalia | 88 | 78 | XM_005320449 |
| Myotis brandtii | bat | Mammalia | 88 | 79 | XM_005860586 |
| Rattus norvegicus | rat | Mammalia | 87 | 75 | XM_230637 |
| Mustela putorius furo | ferret | Mammalia | 88 | 78 | XM_004754183 |
| Microtus ochrogaster | vole | Mammalia | 87 | 74 | XM_005365517 |
| Octodon degus | rodent | Mammalia | 85 | 74 | XM_004635679 |
| Ochotona princeps | pica | Mammalia | 87 | 74 | XM_004585968 |
| Heterocephalus glaber | rat | Mammalia | 86 | 75 | XM_004909847 |
| Callithrix jacchus | marmoset | Mammalia | 84 | 69 | XM_002806762 |
| Papio anubis | baboon | Mammalia | 91 | 83 | XM_003905099 |
| Gorilla gorilla gorilla | gorilla | Mammalia | 93 | 88 | XM_004061840 |
| Saimiri boliviensis boliviensis | monkey | Mammalia | 92 | 84 | XM_003933177 |
| Odobenus rosmarus divergens | walrus | Mammalia | 87 | 76 | XM_004412293 |
| Orcinus orca | whale | Mammalia | 87 | 76 | XM_004270397 |
| Myotis lucifugus | bat | Mammalia | 88 | 76 | XM_006087977 |
| Equus caballus | horse | Mammalia | 89 | 82 | XM_005604466 |
| Ceratotherium simum simum | rhinoceros | Mammalia | 90 | 81 | XM_004433726 |
| Dasypus novemcinctus | armadillo | Mammalia | 88 | 77 | XM_004472392 |
| Felis catus | cat | Mammalia | 90 | 81 | XM_003983802 |
| Sus scrofa | pig | Mammalia | 86 | 74 | XM_005672713 |
| Trichechus manatus latirostris | Trichechidae | Mammalia | 88 | 77 | XM_004376447 |
| Condylura cristata | mole | Mammalia | 89 | 78 | XM_004687152 |
| Pantholops hodgsonii | antelope | Mammalia | 87 | 77 | XM_005985103 |
| Chinchilla lanigera | chinchilla | Mammalia | 86 | 73 | XM_005380908 |
| Echinops telfairi | tenrec | Mammalia | 88 | 75 | XM_004697814 |
| Ovis aries | sheep | Mammalia | 84 | 73 | XM_004014691 |
| Chrysemys pieta bellii | turtle | Reptilia | 82 | 63 | XM_005287452 |
| Geospiza fortis | bird | Aves | 82 | 66 | XM_005426202 |
| Zonotrichia albicollis | bird | Aves | 82 | 66 | XM_005488513 |

TABLE 1-continued

Sequence homologies of p180 of various species to human p180

| Organism | Classification | Protein similarity to human (%): amino acid | Gene identity to human (%): nucleotide | Gene ID |
|---|---|---|---|---|
| Pseudopodoces humilis | bird | Aves | 81 | 64 | XM_005523241 |
| Taeniopygia guttata | Finch | Aves | 82 | 65 | XM_002196328 |
| Gallus gallus | Junglefowl | Aves | 82 | 64 | NM_001257346 |
| Ficedula albicollis | Flycatcher | Aves | 81 | 65 | XM_005042941 |
| Alligator sinensis | alligator | Reptilia | 81 | 62 | XM_006030436 |
| Pelodiscus sinensis | turtle | Reptilia | 80 | 61 | XM_006118575 |
| Sarcophilus harrisii | Tasmanian devil | Mammalia | 81 | 62 | XM_003758168 |
| Melopsittacus undulatus | budgerigar | Aves | 81 | 63 | XM_005152037 |
| Latimeria chalumnae | coelacanth | Sarcopterygii | 81 | 59 | XM_005992924 |
| Capra hircus | goat | Mammalia | 80 | 62 | XM_005688109 |
| Xenopus tropicalis | frog | Amphibia | 78 | 55 | BC074706 |
| Xenopus laevis | frog | Amphibia | 78 | 55 | NM_001089623 |
| Mesocricetus auratus | hamster | Mammalia | 80 | 57 | XM_005068495 |
| Danio rerio | zebrafish | Actinopterygii | 76 | 50 | AY398408 |
| Perca flavescens | yellow perch | Actinopterygii | 78 | 58 | HQ206468 |

Thus, as referred to in the present invention, the "p180 protein" refers to:

(a) a protein that consists of an amino acid sequence with at least 70% sequence identity to the amino acid sequence (SEQ ID NO: 2) of human-derived p180 protein, and which has a capability of promoting polysome formation on an intracellular endoplasmic reticulum membrane;

(b) a protein that consists of an amino acid sequence derived from the amino acid sequence (SEQ ID NO: 2) of the human-derived p180 protein by deletion, substitution, or addition of one or more amino acids, and which has a capability of promoting polysome formation on the intracellular endoplasmic reticulum membrane;

(c) a protein that consists of an amino acid sequence specified by a nucleotide sequence with at least 70% sequence identity to the nucleotide sequence (SEQ ID NO: 1) of a gene encoding the human-derived p180 protein, and which has a capability of promoting polysome formation on the intracellular endoplasmic reticulum membrane;

(d) a protein that consists of an amino acid sequence specified by a nucleotide sequence derived from the nucleotide sequence (SEQ ID NO: 1) of the gene encoding the human-derived p180 protein by deletion, substitution, or addition of one or more nucleotides, and which has a capability of promoting polysome formation on the intracellular endoplasmic reticulum membrane; or (e) a protein that consists of an amino acid sequence specified by a nucleotide sequence hybridizable under stringent conditions with a nucleotide sequence complementary to the nucleotide sequence (SEQ ID NO: 1) of the gene encoding the human-derived p180 protein, and which has a capability of promoting polysome formation on the intracellular endoplasmic reticulum membrane.

With regard to (a) in this mode, by the statement regarding amino acid sequence identity, which reads "with at least 70% sequence identity to the amino acid sequence (SEQ ID NO: 2) of human-derived p180 protein", it is meant that any value for percent sequence identity can be selected from 70% to 100%, and examples of the percent sequence identity value that can be selected include 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and 100%.

With regard to (b) in this mode, by "deletion, substitution, or addition of one or more amino acids", it is meant that the number of amino acids to be deleted, substituted or added ranges from 1 to about 10, and examples of the number of amino acids that can be selected include 1, 2, 3, 4, 5, 6, 7, 8, 9 and 10.

With regard to (c) in this mode, by "with at least 70% sequence identity to the nucleotide sequence (SEQ ID NO: 1) of a gene encoding the human-derived p180 protein", it is meant that any value for percent sequence identity can be selected from 70% to 100%, and examples of the percent sequence identity value that can be selected include 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and 100%.

With regard to (d) in this mode, by "deletion, substitution, or addition of one or more nucleotides", it is meant that the number of nucleotides to be deleted, substituted or added ranges from 1 to about 10, and examples of the number of nucleotides that can be selected include 1, 2, 3, 4, 5, 6, 7, 8, 9 and 10. Additionally, it is presupposed that such "deletion, substitution, or addition of one or more nucleotides" makes it possible to specify a protein having a desired function, without introduction of a stop codon.

With regard to (e) in this mode, by "under stringent conditions", it is meant that the hybridization conditions can be easily determined by a person having an ordinary skill in the art on the basis of, for example, the nucleotide sequence length of a gene. As typically described in *Current Protocols in Molecular Biology*, vol. 1 (John Wiley and Sons, Inc.) and *Molecular Cloning*, 2nd Edition (Sambrook, et al. (1989)), exemplary basic hybridization conditions are hybridization in 5×SSC, 5×Denhardt's solution, and 1% SDS at 25-68° C. for several hours to overnight. In this case, the hybridization temperature is preferably in the range of 45-68° C. (no formamide) or 30-42° C. (50% formamide). Exemplary washing conditions are washing in 0.2×SSC at 45-68° C. It is well known to those skilled in the art that determining hybridization conditions including formamide concentration, salt concentration and temperature as appropriate enables cloning of nucleic acid molecules comprising a nucleotide sequence with a sequence identity above a certain level; and the thus cloned nucleic acid molecules are all included in the scope of the present invention.

The full length of the human p180 protein is the protein having the amino acid sequence of SEQ ID NO: 2 (GenBank Accession No. AB287347), and this protein is encoded by the nucleotide sequence of SEQ ID NO: 1 (GenBank Accession No. AB287347). Also, the aforementioned murine p180 protein is encoded by the nucleotide sequence of GenBank Accession No. NP_077243, the aforementioned rat p180 protein is encoded by the nucleotide sequence of GenBank Accession No. XP_230637, the aforementioned Chinese hamster p180 protein is encoded by the nucleotide sequence of GenBank Accession No. XM_003496471, the aforementioned canine p180 protein is encoded by the nucleotide sequence of GenBank Accession No. NP_001003179, the aforementioned equine p180 protein is encoded by the nucleotide sequence of GenBank Accession No. XP_001915027, the aforementioned simian p180 protein is encoded by the nucleotide sequence of GenBank Accession No. XP_002798281, the aforementioned chimpanzee p180 protein is encoded by the nucleotide sequence of GenBank Accession No. XP_514527, and the aforementioned porcine p180 protein is encoded by the nucleotide sequence of GenBank Accession No. XP_001926148.

For example, when the p180 protein used is the human p180 protein, polysome formation on an intracellular endoplasmic reticulum can be promoted by expressing a portion comprising any of the following regions: a region consisting of the amino acids at positions 27 to 157 of a protein having the amino acid sequence of SEQ ID NO: 2 (human p180 protein); a region consisting of the amino acids at positions 623 to 737 of said protein; a region consisting of the amino acids at positions 738 to 944 of said protein; and a region consisting of the amino acids at positions 945 to 1540 of said protein (Patent Literature 1).

Thus, as referred to in the present invention, the "portion of p180 protein" refers to, for example: a portion comprising an amino acid sequence corresponding to a region consisting of the amino acids at positions 27 to 157 of a protein having the amino acid sequence of SEQ ID NO: 2 (human p180 protein); a portion comprising an amino acid sequence corresponding to a region consisting of the amino acids at positions 623 to 737 of said protein; a portion comprising an amino acid sequence corresponding to a region consisting of the amino acids at positions 738 to 944 of said protein; or a portion comprising an amino acid sequence corresponding to a region consisting of the amino acids at positions 945 to 1540 of said protein. Proteins comprising such a portion can have a capability of promoting polysome formation. With regard to humans, examples of the thus-specified portion of the p180 protein include not only such portions as mentioned above, per se, including: a portion comprising a region consisting of the amino acids at positions 27 to 157 of a protein having the amino acid sequence of SEQ ID NO: 2 (human p180 protein); a portion comprising a region consisting of the amino acids at positions 623 to 737 of said protein; a portion comprising a region consisting of the amino acids at positions 738 to 944 of said protein; and a portion comprising a region consisting of the amino acids at positions 945 to 1540 of said protein, but also MTB-2 domain adjacent to the C-terminal side of the N-terminal transmembrane domain of the human p180 protein, or a highly basic N-terminal region containing a ribosome-binding repeat domain, a highly basic tandem repeat domain, or a microtubule binding and bundling domain (MTB-1 domain) (Patent Literature 1).

As mentioned above, also in the cases of using portions of other mammalian p180 proteins, since the amino acid sequence of the human p180 protein and the amino acid sequences of other mammalian p180 proteins are generally highly conserved, the amino acid sequences of fragments comprising portions or regions corresponding to the amino acid sequences of the proteins (a) to (e) mentioned above can also be used as the "portion of the p180 protein".

The aforementioned recombinant cell of the present invention is secondly characterized by having enhanced intracellular expression of a protein promoting mRNA localization to an endoplasmic reticulum (ER). Examples of such a protein promoting mRNA localization to an endoplasmic reticulum (ER) include SF3b4 protein, especially the full length or a portion of a mammalian SF3b4 protein (e.g., the full-length amino acid sequence 424 AA of SEQ ID NO: 4; RRM1 consisting of 13 to 91 AA of SEQ ID NO: 4; RRM2 consisting of 100 to 179 AA of SEQ ID NO: 4; a C-terminal region consisting of 180 to 424 AA of SEQ ID NO: 4).

In particular, the SF3b4 protein is a protein that is generally detected only in the nucleus. However, further detailed investigation found that in fibroblasts actively secreting collagen, most of the SF3b4 protein is detected in the nucleus but some of said protein is found in the membrane fraction containing cytoplasmic endoplasmic reticulum. The SF3b4 protein (also referred to as "SAP49/SF3b49") is a substance that is classified as an RNA recognition motif (RRM)-type RNA-binding protein (RBP) family due to containing two RNA recognition motifs (RRM) on its amino-terminal side, and which has a proline-rich domain with an unknown function on its carboxy-terminal side. The normal splicing reaction process requires both of these two RNA recognition motifs (RRM) (RRM1, RRM2). These motifs are highly conserved even in yeast, and are presumed to constitute an important functional domain. Further, the SF3b4 protein binds to the other constitutional protein of an SF3b complex, i.e., SAP145 protein, and this binding is also shown to require both of the two RNA recognition motifs (RRM) (RRM1, RRM2) (Champion-Arnaud & Reed, 1994). Thus, it is considered that the RRM domain of the SF3b4 protein not only requires RNA recognition but also acts on a protein-protein interaction.

In this connection, speaking of the comparison between the amino acid sequences of SF3b4 proteins, it is known that the SF3b4 proteins of all the mammalian species investigated show 100% amino acid sequence similarity to the human SF3b4 protein, and that also in the case of other species, the yeast and insect SF3b4 proteins have amino acid sequence similarities of 40 to 54% and 63 to 81%, respectively, to the human SF3b4 protein—thus, the SF3b4 protein is reported to be a very conservative protein in all living organisms.

TABLE 2

Sequence homologies of SF3b4 of various species to human SF3b4

| Organism | Classification | | Protein similarity to human (%): amino acid | Gene identity to human (%): nucleotide | Gene ID |
|---|---|---|---|---|---|
| Pan troglodytes | chimpanzee | Mammalia | 100 | 99 | XM_513768 |
| Gorilla gorilla gorilla | gorilla | Mammalia | 100 | 99 | XM_004026557 |
| Papio anubis | baboon | Mammalia | 100 | 97 | XM_003892563 |
| Pan paniscus | bonobo | Mammalia | 100 | 97 | XM_003817322 |
| Callithrix jacchus | marmoset | Mammalia | 100 | 98 | XM_002759857 |
| Mus musculus | mouse | Mammalia | 100 | 92 | NM_153053 |
| Bos mutus | yak | Mammalia | 100 | 95 | XM_005894874 |
| Bos taurus | cow | Mammalia | 100 | 95 | NM_001205584 |
| Tursiops truncatus | dolphin | Mammalia | 100 | 96 | XM_004315506 |
| Macaca mulatta | monkey | Mammalia | 100 | 99 | NM_001261232 |
| Macaca fascicularis | monkey | Mammalia | 100 | 97 | XM_005542035 |
| Canis lupus | wolf | Mammalia | 100 | 93 | XM_540295 |
| Cricetulus griseus | Chinese hamster | Mammalia | 100 | 91 | XM_003498632 |
| Jaculus jaculus | rodent | Mammalia | 100 | 88 | XM_004668225 |
| Otolemur garnettii | galago | Mammalia | 100 | 95 | XM_003800416 |
| Spermophilus tridecemlineatus | gopher | Mammalia | 100 | 94 | XM_005331144 |
| Rattus norvegicus | rat | Mammalia | 100 | 91 | NM_001011951 |
| Mustela putorius furo | ferret | Mammalia | 100 | 94 | XM_004776825 |
| Microtus ochrogaster | vole | Mammalia | 100 | 91 | XM_005356945 |
| Ochotona princeps | pica | Mammalia | 100 | 91 | XM_004588838 |
| Heterocephalus glaber | rat | Mammalia | 100 | 94 | XM_004853946 |
| Saimiri boliviensis boliviensis | monkey | Mammalia | 100 | 96 | XM_003941980 |
| Odobenus rosmarus divergens | walrus | Mammalia | 100 | 94 | XM_004404182 |
| Orcinus orca | whale | Mammalia | 100 | 95 | XM_004285129 |
| Myotis lucifugus | bat | Mammalia | 100 | 94 | XM_006095177 |
| Equus caballus | horse | Mammalia | 100 | 95 | XM_001488599 |
| Capra hircus | goat | Mammalia | 100 | 95 | XM_005677701 |
| Mesocricetus auratus | Golden hamster | Mammalia | 100 | 92 | XM_005084248 |
| Sarcophilus harrisii | Tasmanian devil | Mammalia | 100 | 86 | XM_003769946 |
| Cavia porcellus | guinea pig | Mammalia | 100 | 93 | XM_003478880 |
| Sorex araneus | shrew | Mammalia | 100 | 92 | XM_004618056 |
| Ceratotherium simum simum | rhinoceros | Mammalia | 100 | 95 | XM_004435941 |
| Dasypus novemcinctus | armadillo | Mammalia | 100 | 91 | XM_004461651 |
| Felis catus | cat | Mammalia | 100 | 95 | XM_004001496 |
| Sus scrota | pig | Mammalia | 100 | 95 | XM_001926489 |
| Trichechus manatus latirostris | Trichechidae | Mammalia | 100 | 94 | XM_004389600 |
| Condylura cristata | mole | Mammalia | 100 | 92 | XM_004689571 |
| Pantholops hodgsonii | antelope | Mammalia | 100 | 95 | XM_005970739 |
| Chinchilla lanigera | chinchilla | Mammalia | 100 | 93 | XM_005378708 |
| Echinops telfairi | tenrec | Mammalia | 100 | 93 | XM_004716571 |
| Ovis aries | sheep | Mammalia | 100 | 95 | XM_004002436 |
| Geospiza fortis | bird | Aves | 98 | 77 | XM_005430326 |
| Pseudopodoces humilis | bird | Aves | 98 | 84 | XM_005533471 |
| Gallus gallus | Junglefowl | Aves | 98 | 81 | XM_423721 |
| Falco peregrinus | Peregrine Falcon | Aves | 97 | 74 | XM_005244315 |
| Chrysemys picta bellii | turtle | Reptilia | 97 | 83 | XM_005293645 |
| Alligator sinensis | alligator | Reptilia | 96 | 79 | XM_006033517 |
| Danio rerio | zebrafish | Actinopterygii | 92 | 79 | NM_153661 |
| Pundamilia nyererei | lapsus | Actinopterygii | 91 | 80 | XM_005728504 |
| Maylandia zebra | Mbuna | Actinopterygii | 91 | 80 | XM_004549154 |
| Capsaspora owczarzaki | monotypic genus | Filasterea | 88 | 77 | XM_004345599 |
| Xenopus tropicalis | frog | Amphibia | 88 | 79 | NM_203785 |
| Xenopus laevis | frog | Amphibia | 87 | 78 | NM_001086631 |
| Aplysia californica | California sea hare | Gastropoda | 77 | 66 | XM_005109109 |
| Drosophila melanogaster | fruit fly | Insecta | 81 | 63 | NM_078503.41 |
| Anopheles gambiae | mosquito | Insecta | 75 | 65 | XM_321584.4 |
| Apis mellifera | honey bee | Insecta | 63 | 57 | Group13.4(31702-33391) |
| Caenorhabditis elegans | worm | Secernentea | 73 | 65 | II(8034428-8035787) |
| Daphnia pulex | common water flea | Crustacea | 79 | 65 | scaffold_1(3898136-3899124) |
| Trichoplax adhaerens | Trichoplax | Tricoplacia | 76 | 64 | scaffold_6(4430698-4432902) |
| Nematostella vectensis | sea anemone | Anthozoa | 68 | 62 | scaffold_59(938974-944852) |
| Strongylocentrotus purpuratus | sea urchin | Echinoidea | 66 | 62 | scaffold_1412 |
| Schistosoma mansoni | schistosome parasite | Trematoda | 65 | 60 | Smp_scaff000217(455137-459876) |
| Arabidopsis thaliana | thale cress | eudicotyledons | 65 | 60 | NM_127407.3 |
| Phytophthora infestans | Chromalveolata | Oomycota | 62 | 56 | Supercont1.42(913888-914494) |

TABLE 2-continued

Sequence homologies of SF3b4 of various species to human SF3b4

| Organism | Classification | | Protein similarity to human (%): amino acid | Gene identity to human (%): nucleotide | Gene ID |
|---|---|---|---|---|---|
| Neurospora crassa | bread mold | Ascomycetes | 52 | 53 | XM_956049.1 |
| Schizosaccharomyces pombe | fission yeast | Schizosaccharomycetes | 54 | 55 | NM_001019427 |
| Saccharomyces cerevisiae | baker's yeast | Saccharomycetes | 41 | 50 | NP_014964 |
| Ashbya gossypii | A. gossypii yeast | Saccharomycetes | 41 | 50 | NM_208241.1 |
| Kluyveromyces lactis | K. lactis yeast | Saccharomycetes | 40 | 47 | XM_452844.1 |
| Chlamydomonas reinhardtii | green algae | Chlorophyceae | 50 | 46 | DS496110 |
| Chlamydomonas reinhardtii | green alga | Chlorophyceae | 50 | 56 | XM_001696328 |

Given the aforementioned fact that the primary amino acid sequence of the SF3b4 protein is widely and highly conserved beyond biological species, it is easily presumed that a function verified using the human SF3b4 protein would be reproduced also in the case of using SF3b4 proteins derived from other biological species.

Thus, as referred to in the present invention, the "SF3b4 protein" refers to:

(i) a protein that consists of an amino acid sequence with at least 70% sequence identity to the amino acid sequence (SEQ ID NO: 4) of human-derived SF3b4 protein, and which has a capability of promoting mRNA localization to an endoplasmic reticulum;

(ii) a protein that consists of an amino acid sequence derived from the amino acid sequence (SEQ ID NO: 4) of the human-derived SF3b4 protein by deletion, substitution, or addition of one or more amino acids, and which has a capability of promoting mRNA localization to the endoplasmic reticulum;

(iii) a protein that consists of an amino acid sequence specified by a nucleotide sequence with at least 70% sequence identity to the nucleotide sequence (SEQ ID NO: 3) of a gene encoding the human-derived SF3b4 protein, and which has a capability of promoting mRNA localization to the endoplasmic reticulum;

(iv) a protein that consists of an amino acid sequence specified by a nucleotide sequence derived from the nucleotide sequence (SEQ ID NO: 3) of the gene encoding the human-derived SF3b4 protein by deletion, substitution, or addition of one or more nucleotides, and which has a capability of promoting mRNA localization to the endoplasmic reticulum; or (v) a protein that consists of an amino acid sequence specified by a nucleotide sequence hybridizable under stringent conditions with a nucleotide sequence complementary to the nucleotide sequence (SEQ ID NO: 3) of the gene encoding the human-derived SF3b4 protein, and which has a capability of promoting mRNA localization to the endoplasmic reticulum.

With regard to (i) in this mode, by the statement regarding amino acid sequence identity, which reads "with at least 70% sequence identity to the amino acid sequence (SEQ ID NO: 4) of human-derived SF3b4 protein", it is meant that any value for percent sequence identity can be selected from 70% to 100%, and examples of the percent sequence identity value that can be selected include 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and 100%.

With regard to (ii) in this mode, by "deletion, substitution, or addition of one or more amino acids", it is meant that the number of amino acids to be deleted, substituted or added ranges from 1 to about 10, and examples of the number of amino acids that can be selected include 1, 2, 3, 4, 5, 6, 7, 8, 9 and 10.

With regard to (iii) in this mode, by "with at least 70% sequence identity to the nucleotide sequence (SEQ ID NO: 3) of a gene encoding the human-derived SF3b4 protein", it is meant that any value for percent sequence identity can be selected from 70% to 100%, and examples of the percent sequence identity value that can be selected include 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and 100%.

With regard to (iv) in this mode, by "deletion, substitution, or addition of one or more nucleotides", it is meant that the number of nucleotides to be deleted, substituted or added ranges from 1 to about 10, and examples of the number of nucleotides that can be selected include 1, 2, 3, 4, 5, 6, 7, 8, 9 and 10. Additionally, it is presupposed that such "deletion, substitution, or addition of one or more nucleotides" makes it possible to specify a protein having a desired function, without introduction of a stop codon.

With regard to (v) in this mode, by "under stringent conditions", it is meant that the hybridization conditions that can be adopted are as described above in relation to the p180 protein.

The full length of the human SF3b4 protein is the protein having the amino acid sequence of SEQ ID NO: 4 (GenBank Accession No. NP_005841.1), and this protein is encoded by the nucleotide sequence of SEQ ID NO: 3 (GenBank Accession No. NP_005841.1). Also, the aforementioned murine SF3b4 protein is encoded by the nucleotide sequence of GenBank Accession No. NP_694693.1, the aforementioned rat SF3b4 protein is encoded by the nucleotide sequence of GenBank Accession No. NP_001011951.1, the aforementioned Chinese hamster SF3b4 protein is encoded by the nucleotide sequence of GenBank Accession No. XP_003498680.1, the aforementioned canine SF3b4 protein is encoded by the nucleotide sequence of GenBank Accession No. XP_540295.3, the aforementioned equine SF3b4 protein is encoded by the nucleotide sequence of GenBank Accession No. XP_001488649.2, the aforementioned simian SF3b4 protein is encoded by the nucleotide sequence of GenBank Accession No. NP_001097793.1, the aforementioned chimpanzee SF3b4 protein is encoded by the nucleotide sequence of GenBank Accession No. XP_513768.2, and the aforementioned porcine SF3b4 protein is encoded by the nucleotide sequence of GenBank Accession No. XP_001926524.1.

When a DNA encoding a protein as a product of interest which is required to be expressed in the present invention is transformed into the cell to be used in a protein expression system, the mRNA (precursor) transcribed from the DNA is converted into a mature mRNA through removal of introns with no genetic information on amino acids by splicing. This process is assumed by a spliceosome, a small nuclear RNA (snRNA)-protein macrocomplex. The spliceosome has five types of low-molecular-weight ribonucleoprotein complexes (snRNPs), and among these snRNPs, the SF3b4 protein is a constituent of U2-snRNP, which contains an RNA-binding domain.

There had hitherto been no report that splicing factors including SF3b4 protein perform some function at the protein translation level. However, the analysis made by the present inventors found that levels of SF3b4 protein in the membrane fraction containing endoplasmic reticulum significantly increases, which occurs concomitantly with the SF3b4 protein association with mRNA and binding to the coiled-coil domain of p180 protein, thereby promoting mRNA localization to the endoplasmic reticulum, and consequently the secretory capacity in the cultured cells can be enhanced.

In other words, it was found that, when a nucleic acid molecule encoding a protein as a product of interest is transformed in the recombinant cell having enhanced expression of either or both of these two types of proteins, the mRNA transcribed from the DNA encoding the protein as a product of interest acts with the SF3b4 protein expressed intracellularly or interacts with the p180 protein expressed intracellularly, or the mRNA transcribed from the DNA encoding the protein as a product of interest interacts with the SF3b4 protein and then the coiled-coil domain of the p180 protein interacts with the SF3b4 protein, whereupon mRNA localization to an endoplasmic reticulum is promoted thereby enhancing the cell's synthetic or secretory capacity of the protein as a product of interest.

All types of fibrosis which can cause long-term injury to various tissues to fibrose them are unknown as to their cause, detailed mechanism of development, and effective therapy, and are poor in prognosis. For example, in the case of idiopathic pulmonary fibrosis, the fibrosis is believed to progress because of an increase in the production of collagen and the like to repair alveolar epithelium injury resulting from various stimuli, which leads to an abnormal repair reaction, but no effective therapy has been established. There had not been a clue to the prevention of abnormal increase in collagen production under such pathological conditions, but it was newly found in the present invention that the SF3b4 protein, which was hitherto believed to function as a splicing factor, plays an essential role in collagen synthesis/secretion, which indicated that collagen synthesis can be suppressed by functional inhibition or expression suppression of SF3b4. Since it is believed that the expression suppression of SF3b4 can be achieved by administration of its specific shRNA or the like and that the functional inhibition of SF3b4 can be induced by various agents inhibiting a splicing process, a possibility was suggested that the functional inhibition or expression suppression of SF3b4 may suppress an abnormal accumulation of collagen in fibrosis and prevent further aggravation of fibrosis.

The cell that can be used to prepare a recombinant cell in the present invention can be of any type as long as it is suitable for protein expression, and examples of the source cell that can be used include mammal-derived cells such as CHO cell, HEK293 cell and HeLa cell. By transfecting the aforementioned full length or portion p180 protein and/or the aforementioned full length or portion of SF3b4 protein into these cells using a method commonly used in the art, the full length or portion of p180 protein and/or the full length or portion SF3b4 protein can be expressed in said cells.

In order to express the aforementioned full length or portion of p180 protein and/or the full length or portion of SF3b4 protein in these cells, a transformation method commonly used in the art can be used. For the purpose of the transformation, the following method can be used: a DNA encoding the full length or portion of p180 protein and/or a DNA encoding the full length or portion of SF3b4 protein are/is incorporated into an expression vector such as pcDNA, pEGFP or pCAGGS, and each expression vector is transformed into the cells.

In the present invention, the CHO cell-derived cell line CHO 5 g was prepared as a recombinant cell stably expressing p180 protein, the CHO cell-derived cell line CHO 3D5 was prepared as a recombinant cell stably expressing SF3b4 protein; and the CHO cell-derived cell line CHO YA7 was prepared as a recombinant cell having enhanced expression of these two proteins at the same time (refer to Example 1 described below), and these cell lines were deposited to the Patent Microorganisms Depositary of the National Institute of Technology and Evaluation (the accession number for the CHO 3D5 is NITE BP-01753; the accession number for the CHO YA7 cell is NITE BP-1535; or the accession number for the CHO 1B2 cell is NITE ABP-01811).

The present inventors also demonstrated that there can be provided a method in which, in a recombinant cell having enhanced expression of the full length or a portion of p180 protein and/or the full length or a portion of SF3b4 protein, a nucleic acid molecule encoding the protein as a product of interest is transformed or production of the protein as a product of interest is increased, whereby a synthetic or secretory capacity of a protein as a product of interest is enhanced and consequently the protein as a product of interest is produced.

In this method, the protein as a product of interest which is produced as a result of enhancing a synthetic or secretory capacity can be any protein intended to be produced by a biotechnological technique. For example, the protein as a product of interest can be exemplified by glycoproteins, and examples of the glycoproteins that can be selected include, but are not limited to, antibodies, collagens, fibronectins, and laminins.

The present inventors provide, in the second mode of the present invention, a method for increasing an amount of a protein as a product of interest to be expressed in a cell as an expression system, wherein, in an expression unit for expressing the protein as a product of interest, a cic-element is inserted, downstream of a promoter and upstream of the start codon in the nucleotide sequence of a DNA encoding the protein as a product of interest, whereby the amount of the protein as a product of interest to be expressed in the cell as an expression system is increased. The aforementioned insertion of the sequence of a cis-element into an expression unit can be exemplified not only by inserting the sequence of a cis-element downstream of a promoter and upstream of the start codon in the nucleotide sequence of a DNA encoding the protein as a product of interest, in an expression plasmid for the protein as a product of interest, but also by inserting the sequence of a cis-element downstream of a promoter and upstream of the ORF start codon of the gene of interest, in a site-specific manner in a case where the promoter and the product of interest have already been genetically introduced into the cell.

As described in the Background Art section, it has been shown that the mRNAs for some proteins, including collagen genes, have a tendency to form a polysome in which multiple ribosomes, machines for protein synthesis, are attached to each other (Patent Literature 1, Non-patent Literature 2). However, there have often been problems where only a small amount of a protein as a product of interest was synthesized or secreted in spite of the fact that a gene transcript encoding the protein as a product of interest was expressed at a high level in cells transfected with a DNA encoding the protein as a product of interest. This was presumed to be possibly because mRNA was not provided in an adequate manner to be used to machines for translation on the endoplasmic reticulum membranes in used cells.

The analysis made based on these considerations found that a cic-element present in the 5' untranslated region of a collagen gene has a capability of increasing an expressed protein amount. More specifically, it was considered that an RRM protein recognizing the cis-element sequence in the 5' untranslated region of a mature mRNA binds to said sequence, thereby leading to an augmentation of mRNA transport/localization onto the endoplasmic reticulum membrane, a place of synthesis of secretory proteins, and to a further increase in translation efficiency.

The cis-element observed in the present invention was proved from the results of the analysis of a type I collagen gene, and the nucleotide sequence of this cis-element was found to be present in the 5' untranslated region of a type I collagen gene. Therefore, in the present invention, the nucleotide sequence of such a cis-element can be exemplified by a sequence derived from the nucleotide sequence of the 5' untranslated region of a type I collagen gene, but cis-element sequences derived from other genes, such as those listed below, can also be used as long as they have a desired effect: a sequence derived from the nucleotide sequence of the 5' untranslated region of a fibronectin gene; a sequence derived from the nucleotide sequence of the 5' untranslated region of the matrix metalloproteinase 14 (MMP14) gene; a sequence derived from the nucleotide sequence of the 5' untranslated region of the prolyl 4-hydroxylase A2 (P4HA2) gene; and a sequence derived from the nucleotide sequence of the 5' untranslated region of the prolyl 4-hydroxylase A1 (P4HA1) gene.

The cis-element that can be used in the present invention is structurally characterized by containing one or more 9- to 12-nucleotide motifs "$GAN_1$-$(X)_n$-$ACN_2$," (n=3 to 6) ($N_1$ and $N_2$ can be independently any of the nucleotides A, T, C and G) in the 5' untranslated region of a gene present in an expression plasmid for expressing a protein as a product of interest. Specific examples of the motifs include motifs present as native cis-elements, which are characterized in that $N_1$ is G and that $N_2$ is A or G or C. More specifically, such motifs can be expressed as "GAG xxx ACV" (SEQ ID NO: 17), "GAG xxxx ACV" (SEQ ID NO: 18), "GAG xxxxx ACV" (SEQ ID NO: 19), and "GAG xxxxxx ACV" (SEQ ID NO: 20) (in these sequences, V represents A or G or C). For example, it was found that in the case of a type I collagen gene, four motifs are included in the 5' untranslated region.

In the case of using a cis-element derived from a type I collagen gene, the nucleotide sequence of the cis-element that can be used is any sequence selected from the group consisting of the full length of SEQ ID NO: 5 or the full length of SEQ ID NO: 7, and the nucleotides at positions 1 to 102, positions 1 to 78, positions 1 to 60, positions 61 to 126, positions 16 to 57, positions 79 to 126, positions 103 to 126, positions 58 to 78, positions 51 to 78, positions 1 to 27, and positions 70 to 78 of SEQ ID NO: 5.

Also, in the case of using a cis-element derived from a fibronectin gene, the nucleotide sequence of the cis-element that can be used is any sequence selected from the group consisting of the full length of SEQ ID NO: 6 and the full length of SEQ ID NO: 8.

TABLE 3

Table 3: List of the sequences of cis-elements

| Cis-element | Sequence | SEQ ID NO |
|---|---|---|
| #1 | tcgtcggagc agacgggagt ttctcctcgg ggtcggagca ggaggcacgc ggagtgtgag gccacgcatg agcggacgct aaccccctcc ccagccacaa agagtctaca tgtctagggt ctagac | 5 |
| #2 | gccgcgccg gctgtgctgc acaggggag gagagggaac cccaggcgcg agcgggaaga ggggacctgc agccacaact tctctggtcc tctgcatccc ttctgtccct ccaccgtcc ccttcccac cctctggccc ccaccttctt ggaggcgaca accccggga ggcattagaa gggatttttc ccgcaggttg cgaagggaag caaacttggt ggcaacttgc ctcccggtgc gggcgtctct cccccaccgt ctcaac | 6 |
| #3 | tcgtcggagc agacgggagt ttctcct | 7 |
| #4 | ccaccttctt ggaggcgaca accccggga gg | 8 |
| #5 | tcgtcggagc agacgggagt ttctcctcgg ggtcggagca ggaggcacgc ggagtgtgag | 21 |
| #6 | gccacgcatg agcggacgct aaccccctcc ccagccacaa agagtctaca tgtctagggt ctagac | 22 |
| #7 | aacgggcgcc gcggcgggga gaagacgcag agcgctgctg ggctgccggg tctcccgctt cccctcctg ctccaaggc ctcctgcatg agggcgcggt agagacccgg acccgcgccg tgctcctgcc gttcgctgc gctccgcccg ggcccggctc agccaggccc cgcggtgagc c | 23 |
| #8 | cagggggagg agagggaacc ccaggcgcga | 24 |
| #9 | gagcgggaag aggggacctg cagccacaac tt | 25 |
| #10 | cagggggagg agagggaacc ccaggcgcga gcgggaagag gggacctgca gccacaactt | 26 |
| #11 | tcgtcggagc agacgggagt ttctcctcgg ggtcggagca ggaggcacgc ggagtgtgag gccacgcatg agcggacgct aaccccctcc ccagccacaa agagtctaca tgt | 27 |

Expression plasmids containing such a cis-element can be used not only in intact host cells, but also in the cells prepared in the present invention: i.e., a cell having enhanced expression of the full length or a portion of p180 protein, a cell having enhanced expression of the full length or a portion of splicing factor 3B subunit 4 (SF3b4) protein, or a cell having enhanced expression of both of these proteins.

Examples are provided herein below for the purpose of more specifically describing the present invention described above, but the examples provided below are not intended to limit this invention.

EXAMPLES

Example 1: Establishment of a Cell Line Expressing SF3b4 Protein, or Coexpressing p180 Protein and SF3b4 Protein Preparation of Plasmids Establishment of a cell line expressing SF3b4 protein, or coexpressing p180 protein and SF3b4 protein was achieved by separately preparing an expression plasmid containing a nucleic acid encoding p180 protein and an expression plasmid containing a nucleic acid encoding SF3b4 protein, and sequentially transfecting these plasmids into CHO cells.

The expression plasmid encoding the full length of human p180 protein (GenBank Accession No. AB287347), pcDNA-p180/54R, was prepared according to the procedure described in Patent Literature 1 (JP 2005-312409).

The expression plasmid encoding the full length of human SF3b4 protein, pEF-SF3b4, was prepared according to the procedure described below. More specifically, the cDNA sequence encoding the full length of human SF3b4 protein (GenBank Accession No. NP_005841.1) was amplified by PCR, and then inserted and ligated into the KpnI-EcoRV site of pEF1/Myc-His vector (produced by Life Technologies) to thereby obtain the plasmid pEF-SF3b4.

The expression plasmid encoding the full length of Chinese hamster SF3b4 protein, pEF-CHO-SF3b4, was prepared according to the procedure described below. More specifically, total RNA was extracted from CHO cells, and the cDNA sequence encoding the full length of Chinese hamster SF3b4 protein (GenBank Accession No. XP_003498680.1) was amplified by PCR. Then, the cDNA sequence was inserted and ligated into the KpnI-EcoRV site of pEF1/Myc-His vector to thereby obtain the plasmid pEF-CHO-SF3b4.

The expression plasmid encoding the sequence of a human cis-element (e.g., cis-elements #1 to #11), pEF-Cis, was prepared according to the procedure described below. More specifically, a nucleic acid sequence encoding a human cis-element (e.g., SEQ ID NO: 5 in the case of cis-element #1) was amplified by PCR, and then inserted and ligated into the BglII-HindIII site of pEGFP vector (produced by Clontech) to thereby obtain the plasmid prCMV-cis#-SEAP. The details of expression vectors each containing a different cis-element will be described in Example 9.

Preparation of Cells Stably Expressing p180 Protein

Establishment of CHO cells stably expressing human p180 protein was achieved according to the procedure described in Patent Literature 1. More specifically, the human p180 protein-expressing plasmid pcDNA-p180/54R was transfected into CHO cells by a lipofection method, and then the transfected cells were cultured in the presence of 400 µg/mL of zeocin, whereby drug selection was done. After the culture for 10 days, zeocin-resistant cell line colonies were isolated to establish the cell line CHO 5 g which stably expresses p180 protein.

Preparation of Cells Stably Expressing SF3b4 Protein

To prepare CHO cells stably expressing human SF3b4 protein, the human SF3b4 protein-expressing plasmid pEF-SF3b4 was transfected into CHO cells by a lipofection method, and then the transfected cells were cultured in the presence of 400 µg/mL of G418, whereby drug selection was done. After the culture for 10 days, G418-resistant cell line colonies were isolated to establish the cell line CHO 3D5 which stably expresses SF3b4 protein (deposited to the Patent Microorganisms Depositary of the National Institute of Technology and Evaluation (NPMD), 2-5-8 Kazusakamatari, Kisarazu-shi, Chiba, Japan; Accession Number: NITE BP-01753; Deposit date: Nov. 21, 2013).

Preparation of Cells Stably Coexpressing p180 Protein and SF3b4 Protein

Next, to establish CHO cells stably coexpressing human p180 protein and human SF3b4 protein, the SF3b4 protein-expressing plasmid pEF-SF3b4 was transfected into the cell line CHO 5 g by a lipofection method. Then, the transfected cells were cultured in the presence of 400 µg/mL of G418 and 100 µg/mL of zeocin, whereby drug selection was done.

After the culture for 14 days, G418- and zeocin-resistant cell line colonies were isolated to establish the cell line CHO YA7 which stably coexpresses human p180 protein and human SF3b4 protein (deposited to the Patent Microorganisms Depositary of the National Institute of Technology and Evaluation (NPMD), 2-5-8 Kazusakamatari, Kisarazu-shi, Chiba, Japan; Accession Number: NITE BP-1535; Deposit date: Feb. 13, 2013).

Thereafter, to establish CHO cells stably coexpressing human p180 protein and Chinese hamster SF3b4 protein, a plasmid expressing human p180 and Chinese hamster SF3b4 was transfected into CHO cells by a lipofection method. Then, the transfected cells were cultured in the presence of 300 µg/mL of hygromycin, whereby drug selection was done. After the culture for 14 days, hygromycin-resistant cell line colonies were isolated to establish the cell line CHO 1B2 which stably expresses human p180 protein and Chinese hamster SF3b4 protein (deposited to the Patent Microorganisms Depositary of the National Institute of Technology and Evaluation (NPMD), 2-5-8 Kazusakamatari, Kisarazu-shi, Chiba, Japan; Accession Number: NITE ABP-01811; Deposit date: Mar. 4, 2014).

Verification of Cell Properties

To verify that CHO 5 g cells stably expressed p180 protein, that CHO 3D5 cells stably expressed SF3b4 protein, and that CHO YA7 cells and CHO 1B2 cells coexpressed p180 protein and SF3b4 protein, CHO 5 g cells, CHO 3D5 cells, CHO YA7 cells, and CHO 1B2 cells were each cultured in a Dulbecco's modified Eagle's medium (DMEM) supplemented with 5% fetal bovine serum at 37° C. in the presence of 5% $CO_2$. CHO cells were also cultured as control cells.

After 40 hours, $1 \times 10^5$ of each type of the cells suspended by trypsin treatment were harvested by centrifugation as samples for analysis, and then analyzed by Western blotting for intracellularly expressed p180 protein using an anti-p180 antibody (refer to Ogawa-Goto, K. et. al., *J. Virol.*, 76 (2002) 2350-2362), and for intracellularly expressed SF3b4 protein using an anti-SF3b4 antibody (produced by Santacruz).

According to FIG. 1, as for the CHO cells, the expressed p180 amount was below the limit of detection, and SF3b4 protein was observed to be endogenously expressed at a low level (lane 1). As for the CHO 3D5 cells, the expressed p180 protein amount was below the limit of detection as in the case of the CHO cells, but SF3B4 protein was highly expressed (lane 2). As for the CHO 5 g cells, p180 protein was highly expressed, but SF3b4 protein was observed to be endogenously expressed at a low level (lane 3). As for the CHO YA7 cells and the CHO 1B2 cells, p180 protein and SF3b4 protein were both highly expressed (lanes 4 and 6). These results verified that there were successfully established the CHO 5 g cells highly expressing p180 protein, the CHO 3D5 cells highly expressing SF3b4 protein, and the CHO cell-derived cell lines CHO YA7 and CHO 1B2 coexpressing p180 protein and SF3b4 protein.

Example 2: Activation of Secretion by p180 Protein Expression and/or SF3b4 Protein Expression Using the cell lines prepared in Example 1, i.e., the CHO 5 g cells expressing p180 protein, the CHO 3D5 cells expressing SF3b4 protein, and the cell line CHO YA7 coexpressing p180 protein and SF3b4 protein, investigation was made of p180 protein expression and/or SF3b4 protein expression, and activation of protein secretion.

An expression plasmid for human placental secreted alkaline phosphatase (SEAP) as a secretory marker was constructed according to the procedure described below. More specifically, a cDNA fragment encoding the full length of SEAP protein (GenBank Accession No. NP_001623.3) was inserted and ligated into the NheI-XhoI site of an expression vector for mammalian cells (pEGFP-C3; produced by Clontech) to thereby obtain the SEAP protein expression plasmid prCMV-SEAP.

To evaluate the respective types of cells for the secretory capacity of SEAP protein, the SEAP expression plasmid and a β-galactosidase-expressing plasmid for internal normalization, pEF1-LacZ (produced by Life Technologies), were cotransfected into each of the CHO 3D5 cells, the CHO 5 g cells, the CHO YA7 cells, and the CHO cells using the Lipofectamine LTX reagent (produced by Life Technologies). The transfected cells were cultured in a DMEM supplemented with 0.1% fetal bovine serum for 20 hours, and then the culture supernatant was mixed with a substrate solution containing p-Nitrophenyl phosphate (pNPP; produced by Sigma). After the reaction at room temperature for 30 minutes, the mixture was measured for absorbance at a wavelength of 405 nm using an absorbance spectrophotometer. The β-galactosidase activity in cell fractions was measured according to the standard protocol for the β-Galactosidase Enzyme Assay System (produced by Promega).

Figure 2:
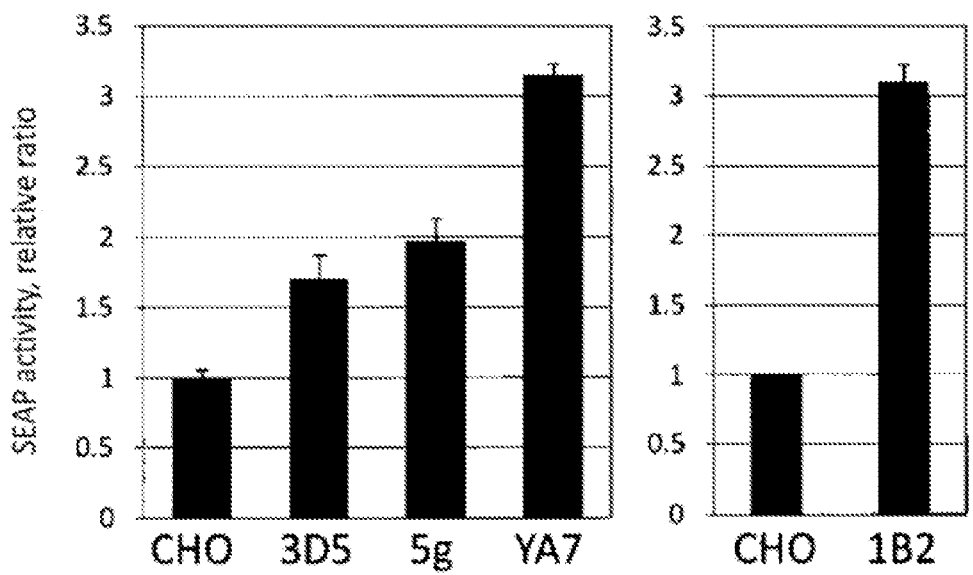
FIG. 2 comparatively shows the results of expression of secreted alkaline phosphatase (SEAP) protein in the cases of exogenously introducing an expression plasmid for human placental SEAP as a secretory marker into each of the different types of cells prepared in Example 1.

The SEAP activities normalized by the measured β-galactosidase values are shown in FIG. 2. In the cases of the CHO 5 g cells expressing p180 protein alone and the CHO 3D5 cells expressing SF3b4 protein alone, the SEAP secretory activity in culture supernatant increased significantly by 1.7 to 2.0 times as compared to the CHO cells (FIG. 2). In the case of the CHO YA7 cells coexpressing p180 protein and SF3b4 protein, the SEAP activity increased more significantly by 3.1 times as compared to the CHO cells. These facts demonstrated that in both cases of the expression of p180 protein alone and the expression of SF3b4 protein alone, the SEAP secretory activity was increased significantly as compared to the case of the CHO cells, but in the case of the coexpression of p180 protein and SF3b4 protein, the secretory capacity in cells was increased more remarkably than in the case of the CHO cells.

Also, as compared to the SEAP activity of the CHO cells, which was taken as 1, the SEAP activity ratio of the CHO 1B2 cells was 3.1, which indicates that the CHO 1B2 cells showed a remarkable increase in SEAP activity. This fact demonstrated that Chinese hamster SF3b4 highly similar to human SF3b4 has comparable secretion enhancement activity to human SF3b4.

Example 3: Promotion of mRNA Localization to a Membrane Fraction by Coexpression of p180 Protein and SF3b4 Protein Using the cell lines prepared in Example 1, i.e., the cell line CHO 5 g expressing p180 protein, the cell line CHO 3D5 expressing SF3b4 protein, and the cell line CHO YA7 coexpressing p180 protein and SF3b4 protein, investigation was made of the relationship of p180 protein expression and/or SF3b4 protein expression with promotion of mRNA localization to a membrane fraction.

Figure 3:
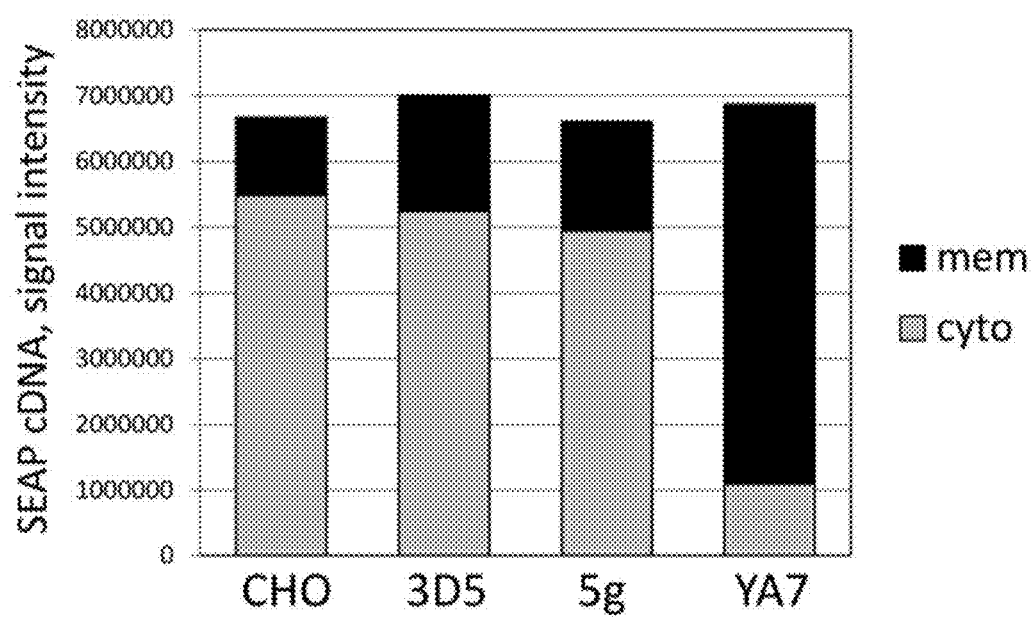
FIG. 3 comparatively shows the degrees of localization of secreted alkaline phosphatase (SEAP) mRNAs to the membrane fractions in the cases of exogenously introducing an expression plasmid for human placental SEAP as a secretory marker into each of the different types of cells prepared in Example 1.

The aforementioned SEAP expression plasmid was transfected into each of the CHO YA7 cells and the control cells using the Lipofectamine LTX reagent, and after 40 hours, the transfected cells were fractionated into a cytoplasmic fraction and a membrane fraction. The fractionation was performed according to the procedure described in Non-patent Literature 1 (Ueno, et al., (2010) *J Biol Chem* 285, 29941-29950). RNA was extracted from each of these fractions according to the standard protocol for the Trizol-LS reagent (produced by Life Technologies). Then, quantitative PCR was performed with SEAP-specific primers to quantitate SEAP mRNA (FIG. 3).

The results showed that the total mRNA content in both of the cytoplasmic and membrane fractions was almost the same among the CHO 3D5 cells, the CHO 5 g cells, the CI-TO YA7 cells, and the CI-TO cells. However, about 30% of the total mRNA was present in the membrane fraction in the cases of the CHO cells, the CHO 3D5 cells, and the CHO 5 g cells, whereas in the case of the CHO YA7 cells, about 70% of the total mRNA was localized in the membrane fraction—mRNA localization was greatly shifted from the cytoplasm to the membrane fraction.

These facts demonstrated that the CHO YA7 cells coexpressing p180 protein and SF3b4 protein have a capability of actively localizing mRNA to a membrane fraction during biosynthesis of secretory proteins.

Example 4: Construction of an Expression Vector in which a Cis-Element is Inserted into a Secreted Alkaline Phosphatase Expression Unit In this example, using the cell lines prepared in Example 1, i.e., the cell line CHO 3D5 expressing SF3b4 protein, and the cell line CHO YA7 coexpressing p180 protein and SF3b4 protein, investigation was made of the structure of an expression plasmid for the purpose of further increasing protein expression efficiency.

An expression vector in which a cis-element was inserted into the SEAP expression plasmid prCMV-SEAP mentioned in Example 2 was constructed according to the procedure described below. RNA derived from human fibroblasts was prepared according to the procedure described in Non-patent Literature 1 (Ueno, et al., (2010) *J Biol Chem* 285, 29941-29950), and RT-PCR was performed using the prepared RNA as a template. In the process of amplification, cis-element #1 (SEQ ID NO: 5) derived from human type I collagen α1 was amplified using the primers (SEQ ID NO: 15, SEQ ID NO: 16) in which the BglII and HindIII recognition sequences were added towards the 5' and 3' ends, respectively. The amplified fragment was treated with BglII-HindIII, and then inserted and ligated into the BglII-HindIII site located between the CMV promoter and SEAP ORF in prCMV-SEAP. Thus, there was obtained the expression plasmid prCMV-cis#1-SEAP in which cis-element #1 was inserted between the CMV promoter and the SEAP start methionine codon (FIG. 4A).

Example 5: Activation of Protein Secretion by Cis-Element

Using the cis-element-containing expression plasmid prepared in Example 4, investigation was made of the influence on secretion of expression protein. The two expression plasmids provided in Example 4, i.e. prCMV-cis#1-SEAP and prCMV-SEAP, were transfected using the Lipofectamine LTX reagent (produced by Life Technologies). The cells used in the transfection were the four cell lines prepared in Example 1. The transfected cells were cultured in a DMEM supplemented with 0.1% FBS for 20 hours, and then the culture supernatant was mixed with a substrate solution containing the fluorescent substrate 4-Methylumbelliferyl phosphate (4-MUP; produced by Sigma). After the reaction at room temperature for 30 minutes, the mixture was measured for fluorescence intensity (excitation at 360 nm, emission at 440 nm) using a fluorophotometer. Also, in order to correct transfection efficiency by total SEAP cDNA content, total mRNA was extracted from cell fractions using a Trizol reagent (produced by Life Technologies), and quantitative PCR was performed with SEAP-specific primers to quantitate SEAP cDNA. The SEAP activity ratio of prCMV-cis#1-SEAP to prCMV-SEAP, which was corrected by total SEAP cDNA content, is shown in FIGS. 4B and 4C.

According to the results of this investigation, in the case of using the CHO cells, SEAP activity was increased by 2.7 times by insertion of cis-element #1. Also in all the cases of using the CHO 3D5 cells, the CHO 5 g cells, and the CHO YA7 cells, SEAP activity was increased by 3.0 to 3.2 times by insertion of cis-element #1. These results showed that in the different types of CHO cells, the amount of protein synthesized and secreted per transcript can be increased by inserting cis-element #1 into an expression unit.

Thereafter, in order to compare the SEAP activity ratios of the aforementioned different types of cells after insertion of cis-element #1 with the SEAP activity of the CHO cells without insertion of cis-element #1, the SEAP activities of these types of cells upon introduction of prCMV-cis#1-SEAP were determined, with the SEAP activity of the CHO cells upon introduction of prCMV-SEAP being taken as 1 (FIG. 4C). The SEAP activity ratios of the CHO 3D5 cells and the CHO 5 g cells upon use of cis-element #1 increased by 4.7 and 6.3 times, respectively, as compared to that of the control CHO cells. Also, the SEAP secretory activity of the CHO YA7 cells remarkably increased by 9.4 times as compared to that of the control CHO cells.

Hence, it was demonstrated that the activity for secreting a protein expressed from an expression plasmid can be increased by the coexistence of cis-element #1 and SF3b4 protein or the coexistence of cis-element #1 and p180 protein, and that the protein secretory activity of cells can be more remarkably enhanced by the coexistence of the three factors cis-element #1, SF3b4 protein and p180 protein.

Example 6: Activation of Collagen Secretion by Cis-Element #1

In this example, using a cis-element-containing expression plasmid, investigation was made of the influence on collagen expression.

An expression plasmid for human type I collagen α1 (COL1A1) was constructed according to the procedure described below. More specifically, a cDNA fragment encoding the full length of COL1A1 (GenBank Accession No. NM_000088.3) was inserted and ligated into the NheI-XhoI site of an expression vector for mammalian cells (pEGFP-C3; produced by Clontech) to thereby obtain the cis-element #1-containing and COL1A1 (1 to 5297 nt)-expressing plasmid prCMV-COL1A1 under the control of a CMV promoter. Also, gene fragments each consisting of 127 to 4251 nt or 127 to 5297 nt, which encode the full length of COL1A1 ORF alone instead of the full length of the COL1A1 gene, were amplified in the same way to construct prCMV-COL1A1-ORF and prCMV-COL1A1-ORF-UTR. Further, expression plasmids for human type II collagen α1 (COL2A1) and human type III collagen α1 (COL3A1) were constructed according to the procedure described below. More specifically, a cDNA fragment encoding the full length of COL2A1 (GenBank Accession No. NP_001835.3) or COL3A1 (GenBank Accession No. NP_000081.1) was inserted and ligated into the EcoRV-NotI site of pcDNA-cis#1 in which cis-element #1 was inserted into an expression vector for mammalian cells (pcDNA; produced by Invitrogen), whereby the COL2A1 (1 to 4464 nt)-expressing plasmid pcDNA-cis#1-COL2A1 or the COL3A1 (1 to 4401 nt)-expressing plasmid peDNA-cis#1-COL3A1 was obtained under the control of a CMV promoter.

Next, in order to investigate the ability of cis-element #1 to activate procollagen secretion, prCMV-COL1A1 was transfected by a lipofection method into the three cell lines prepared in Example 1. After the transfected cells were cultured for 40 hours in a DMEM supplemented with 0.1% fetal bovine serum and 200 μM ascorbic acid, COL1A1 procollagen content in culture supernatant was analyzed by Western blotting (FIG. 5A).

According to the results of this analysis, as compared to the procollagen content in the control CHO cells, which was taken as 1, the procollagen content in the CHO YA7 cells increased by about 20 times. Also, for the purpose of evaluation of cis-element #1, the cis-element #1-free plasmid prCMV-COL1A1-ORF or prCMV-COL1A1-ORF-UTR was genetically introduced into the control CHO cells in the same way. In these cases, the procollagen contents in culture supernatant were below the limit of detection by Western blotting.

Further, in order to investigate the secreted amount of homotrimer-forming collagen, pcDNA-cis#1-COL2A1, pcDNA-cis#1-COL3A1, or prCMV-COL1A1 or prCMV-COL1A1-ORF, which were prepared in this example, was transfected by a lipofection method into each of the three cell lines prepared in Example 1. After the transfected cells were cultured for 72 hours in a DMEM supplemented with 2% fetal bovine serum and 200 μM ascorbic acid, the culture supernatant was harvested, HCl was added to 0.1 N to make the pH acidic, pepsin (produced by Sigma) was added to 0.5 mg/mL, and digestion reaction was carried out at 4° C. for 16 hours. NaCl was added to the reaction mixture to give a concentration of 1 M, and the mixture was left on ice for 3 hours and then centrifuged. The resulting precipitate was washed with 1 M NaCl and 95% ethanol. The thus-obtained purified collagen samples were subjected to electrophoresis by SDS-PAGE to compare the band intensities of the collagens. According to the results of this comparison, the amounts of the homotrimers COL1A1, COL2A1 and COL3A1 secreted in the CHO YA7 cells significantly increased by 1.8, 1.9 and 3.7 times, respectively, as compared to those in the control CHO cells, which are taken as 1 (FIGS. 5B to 5D). Even in the absence of cis-element #1, the homotrimer amounts secreted in the CHO 3D5 cells and the CHO YA7 cells increased by 1.5 and 2.1 times, respectively, as compared to the control.

Hence, it was demonstrated that cis-element #1 is capable of enhancing the expression of collagen molecules in the different types of CHO cells, and that the secreted amount of collagen with maintained triple-helical structure is further increased by using cis-element #1 in the presence of SF3b4 protein and/or p180 protein.

Example 7: Enhancement Effect of Cis-Element on Expression of Antibody Molecules The influence of cis-element on antibody expression was investigated according to the procedure described below.

An expression plasmid for full-length antibody heavy and light chains was constructed according to the procedure described below. More specifically, full-length antibody heavy chain (I-IC) and light chain (LC) sequences encoded by the anti-IL-8 antibody-expressing plasmid (p6G425V11N35A.choSD, ATCC 209552) were synthesized by the gene synthesis service (provided by MBL). Then, the full-length heavy chain ORF and light chain ORF were inserted and ligated into the NheI-SpeI site and the KpnI-EcoRV site of the pEF1/Myc-His vector, respectively. Thereafter, the light chain expression cassette was cleaved with ClaI, and inserted and ligated into the ClaI site of the heavy chain expression vector, whereby the anti-IL-8 antibody (HC, LC) coexpression plasmid pEF-HC-LC was constructed. Further, cis#1 was inserted upstream of the heavy chain and light chain ORFs in this plasmid to construct the expression plasmid pEF-cis#1-HC-LC.

Figure 6:
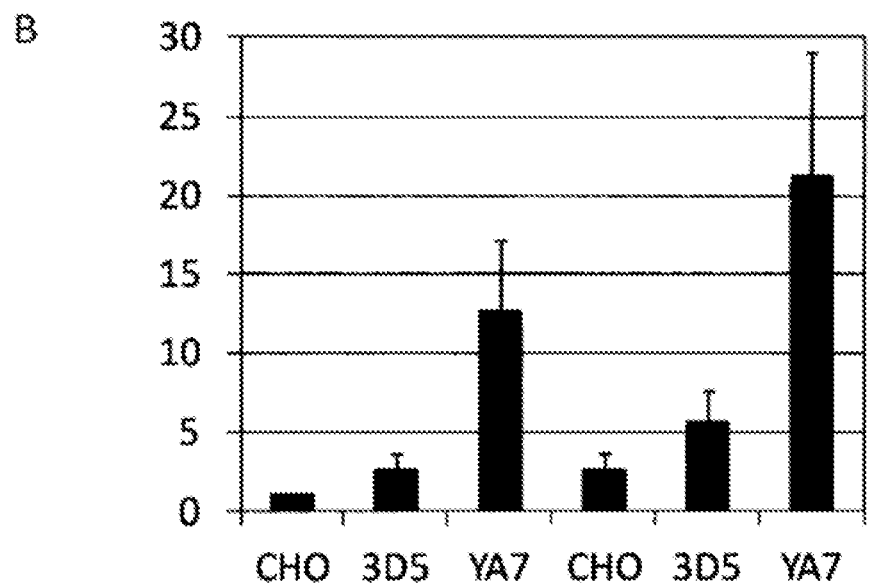
FIG. 6 shows that antibody secretion is activated by cis-element insertion.

Each of pEF-HC-LC and pEF-cis#1-HC-LC was transfected by a lipofection method into each of the three cell lines prepared in Example 1. After the transfected cells were cultured in a DMEM supplemented with 0.1% fetal bovine serum for 96 hours, antibody production in culture supernatant was quantified by ELISA using the Human IgG ELISA Quantitation Set (produced by Bethyl). According to the results of this investigation, the secreted antibody amount in the CHO cells was increased by 2.7 times by insertion of cis-element #1. Likewise, the secreted antibody amounts in the CHO 3D5 cells and the CHO YA7 cells were also increased by 2.5 and 1.8 times, respectively, by insertion of cis-element #1 (FIG. 6A). These results showed that the secreted antibody amount in the different types of CHO cells can be increased by inserting cis-element #1 into an expression unit.

As shown in FIG. 6B, as compared to the secreted antibody amount in the CHO cells upon introduction of pEF-HC-LC, which was taken as 1, the secreted antibody amounts in the CHO 3D5 cells incorporating SF3b4 and in the CHO YA7 cells incorporating SF3b4 and p180 increased by 2.5 and 12.6 times, respectively, which demonstrated that secreted antibody amount can be increased by insertion of p180 protein and/or SF3b4 protein. These tendencies become more significant when cis-element #1 is used—in the presence of this element, the secreted antibody amounts in the CHO 3D5 cells and the CHO YA7 cells remarkably increased by 5.6 and 21.3 times, respectively, as compared to the control CHO cells.

Hence, it was demonstrated that cis-element #1 acts positively on antibody production, and that the activity of this element becomes more significant in the presence of SF3b4 protein or p180 protein, or both of these proteins.

Example 8: Comparison Between Kozak Sequence and Cis-Element #1 in Terms of Secretion Activation Effect This example was intended to compare the secretion activation effect of a cis-element with that of the kozak sequence which is known as a consensus sequence involved in the initiation of translation in the mRNA of eukaryocytes.

The expression plasmids prCMV-SEAP-kozak and prCMV-cis#1-SEAP-kozak, in which the 6-bp sequence TCCTGC immediately preceding the start methionine codon ATG of each of prCMV-SEAP and prCMV-cis#1-SEAP prepared in Example 4 was substituted by the sequence GCCACC, were constructed according to the procedure described below. More specifically, PCR was first performed with SEAP-specific primers to amplify a SEAP fragment (1 to 132 nt) in which the sequence GCCACC was added immediately preceding ATG. Then, a SEAP (1 to 132 nt) region was excised from prCMV-SEAP and prCMV-cis#1-SEAP with HindIII-PstI and replaced with the amplified fragment treated with HindIII-PstI, whereby there were obtained the SEAP expression plasmids prCMV-SEAP-kozak and prCMV-cis#1-SEAP-kozak in which the kozak sequence was inserted upstream of SEAP ORF.

The plasmids prCMV-SEAP, prCMV-SEAP-kozak, prCMV-cis#1-SEAP, and prCMV-cis#1-SEAP-kozak were each transfected into each of the CHO cells, the CHO 3D5 cells and the CHO YA7 cells, and after the culture for 20 hours, SEAP activity in culture supernatant was measured according to the procedure described in Example 5. The results confirmed that as compared to the case of prCMV-SEAP, the SEAP activity of the CHO cells was enhanced by at least twice with prCMV-cis#1-SEAP and prCMV-cis#1-SEAP-kozak (FIG. 7)—the effect of these plasmids is comparable to or greater than that of the kozak sequence which is known to be effective for protein expression.

Figure 7:
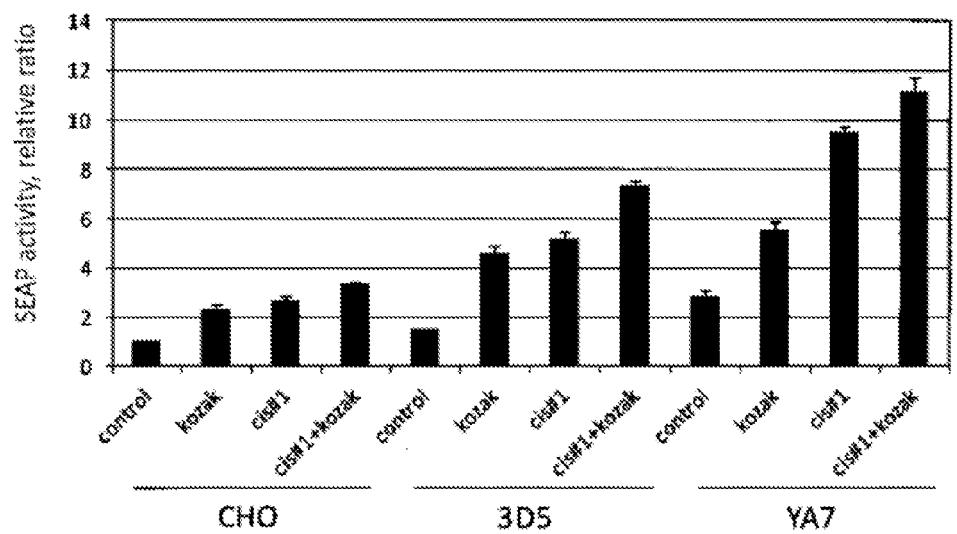
FIG. 7 shows a comparison of the effects of the kozak sequence and cis-element #1 on secretion activation, using the CHO cells and the CHO YA7 cells.

This tendency of enhancement was also strongly observed in the CHO 3D5 cells and the CHO YA7 cells. The SLAP activity ratio increased by 3.3 to 3.4 times in the presence of cis-element #1, and by 3.3 to 4.9 times in the presence of both the kozak sequence and cis-element #1 (FIG. 7).

Hence, it was demonstrated that cis-element #1 has a stronger secretion activation effect on CHO cells, CHO 3D5 cells, and CHO YA7 cells than the kozak sequence, and that the secretory activity of these types of cells can be further enhanced by using the three factors cis-element #1, SF3b4 protein, and p180 protein in combination with the kozak sequence.

Example 9: Protein Expression Enhancement Effect of Addition of Cis-Element

Expression plasmids containing various types of cis-element were each used in each of the cell lines prepared in Example 1 to investigate the details of cis-element sequences with a protein expression enhancement effect.

The expression vector prCMV-cis#2-SEAP, in which the cis-element sequence of human-derived fibronectin gene, cis-element #2 (SEQ ID NO: 6), was inserted into prCMV-SEAP, was constructed according to the procedure described below. More specifically, RNA derived from human fibroblasts was prepared according to the procedure described in Non-patent Literature 1 (Ueno, et al., (2010) *J Biol Chem* 285, 29941-29950), and RT-PCR was performed using the prepared RNA as a template. In the process of amplification, a fragment comprising cis-element #2 was amplified using the primers (SEQ ID NO: 13, SEQ ID NO: 14) in which the BglII and HindIII recognition sequences were added to sites towards the 5' and 3' ends, respectively. The amplified fragment was treated with BglII-HindIII, and then inserted and ligated into the BglII-HindIII site located between the CMV promoter and SEAP ORF in prCMV-SEAP. Thus, there was obtained an expression plasmid in which cis-element #2 was inserted between the CMV promoter and the SEAP start methionine codon.

The expression vectors prCMV-cis#3-SEAP and the like, in which the cis-element sequence of human-derived type I collagen a1 gene, cis-element #3, or the cis-element sequence of human-derived fibronectin gene, cis-element #4, was inserted into prCMV-SEAP, were constructed according to the procedure described below. More specifically, cis-element-containing primers designed for cis-element #3 (SEQ ID NO: 9, SEQ ID NO: 10) or cis-element-containing primers designed for cis-element #4 (SEQ ID NO: 11, SEQ ID NO: 12) were subjected to heat treatment at 95° C. for 10 minutes and then the temperature was lowered in stages to 25° C. to anneal the two primers, whereby each type of linker was prepared. These types of linker were each inserted and ligated into the BglII-HindIII site located between the CMV promoter and SEAP ORF in prCMV-SEAP. Thus, there were obtained expression plasmids in which cis-element #3 (SEQ ID NO: 7) or cis-element #4 (SEQ ID NO: 8) was inserted between the CMV promoter and the SEAP start methionine codon.

The expression vectors prCMV-cis#5-SEAP and prCMV-cis#6-SEAP in which cis-element #5 or #6 was inserted into prCMV-SEAP were constructed according to the procedure described below. Fragments comprising cis-element #5 (1-60) or cis-element #6 (61-126) were amplified using respective sets of primers (SEQ ID NOs: 28 and 29, or SEQ ID NOs: 30 and 31), each having added thereto the partial BglII and HindIII recognition sequences of cis-element #1. The amplified fragments were each treated with BglII-HindIII, and then inserted and ligated into the BglII-HindIII site located between the CMV promoter and SEAP ORF in prCMV-SEAP. Thus, there were obtained expression plasmids in which cis-element #5 or cis-element #6 was inserted between the CMV promoter and the SEAP start methionine codon.

The expression vector prCMV-cis#7-SEAP, in which cis-element #7 was inserted into prCMV-SEAP, was constructed according to the procedure described below. A COL2A1 gene-derived sequence was synthesized, and then inserted and ligated into the BglII-HindIII site located between the CMV promoter and SEAP ORF in prCMV-SEAP, using the BglII and HindIII recognition sequences added to the ends. Thus, there was obtained an expression plasmid in which cis-element #7 was inserted between the CMV promoter and the SEAP start methionine codon.

The expression vectors prCMV-cis#8-SEAP, prCMV-cis#9-SEAP, and prCMV-cis#10-SEAP, in which a cis-element #2-derived sequence—cis-element #8, #9 or #10— was inserted into prCMV-SEAP, were constructed according to the procedure described below. More specifically, cis-element-containing primers designed for cis-element #8 (SEQ ID NO: 32, SEQ ID NO: 33), cis-element-containing primers designed for cis-element #9 (SEQ ID NO: 34, SEQ ID NO: 35), or cis-element-containing primers designed for cis-element #10 (SEQ ID NO: 36, SEQ ID NO: 37) were subjected to heat treatment at 95° C. for 10 minutes and then the temperature was lowered in stages to 25° C. to anneal the two primers, whereby each type of linker was prepared. These types of linker were each inserted and ligated into the BglII-HindIII site located between the CMV promoter and SEAP ORF in prCMV-SEAP. Thus, there were obtained expression plasmids in which cis-element #8 (SEQ ID NO: 24), cis-element #9 (SEQ ID NO: 25), or cis-element #10 (SEQ ID NO: 26) was inserted between the CMV promoter and the SEAP start methionine codon.

The expression vector prCMV-cis#11-SEAP, in which cis-element #11 was inserted into prCMV-SEAP, was constructed according to the procedure described below. A fragment comprising cis-element #11 (1-113) was amplified using primers (SEQ ID NO: 38, SEQ ID NO: 39) having added thereto the partial BglII and HindIII recognition sequences of cis-element #1. The amplified fragment was treated with BglII-HindIII, and then inserted and ligated into the BglII-HindIII site located between the CMV promoter and SEAP ORF in prCMV-SEAP. Thus, there was obtained an expression plasmid in which cis-element #11 (SEQ ID NO: 27) was inserted between the CMV promoter and the SEAP start methionine codon.

TABLE 4

Table 4: List of primers for cis-element amplification

| Target cis# | Primer sequence | SEQ ID NO |
|---|---|---|
| #1 | aaaaaaagat cttcgtcgga gcagacg | 15 |
| #1 | aaaaaaagc ttgtctagac cctagac | 16 |
| #2 | aaaaaaagat ctgcccgcgc cggctgt | 13 |
| #2 | aaaaaaagc ttgttgagac ggtgggga | 14 |
| #3 | gatcttcgtc ggagcagacg ggagtttctc cta | 9 |
| #3 | agcttaggag aaactcccgt ctgctccgac gaa | 10 |
| #4 | gatcttctgc atcccttctg tccctccaca | 11 |
| #4 | agcttgtgga gggacagaag ggatgcagaa | 12 |
| #5 | aaaaaaagat cttcgtcgga gcagacggga gt | 28 |
| #5 | aaaaaaagc ttctcacact ccgcgtgcct cc | 29 |
| #6 | aaaaaaagat ctgccacgca tgagcggacg ct | 30 |
| #6 | aaaaaaagc ttgtctagac cctagacatg ta | 31 |
| #8 | gatctcaggg ggaggagagg gaaccccagg cgcgaa | 32 |
| #8 | agctttcgcg cctggggttc cctctcctcc ccctga | 33 |
| #9 | gatctgagcg ggaagagggg acctgcagcc acaactta | 34 |
| #9 | agcttaagtt gtggctgcag gtcccctctt cccgctca | 35 |
| #10 | gatctcaggg ggaggagagg gaaccccagg cgcgagcggg aagaggggac ctgcagccac aactta | 36 |
| #10 | agcttaagtt gtggctgcag gtcccctctt cccgctcgcg cctggggttc cctctcctcc ccctga | 37 |
| #11 | aaaaaaagat cttcgtcgga gcagacggga gt | 38 |
| #11 | aaaaaaagc ttacatgtag actctttgtg gc | 39 |

Figure 8:
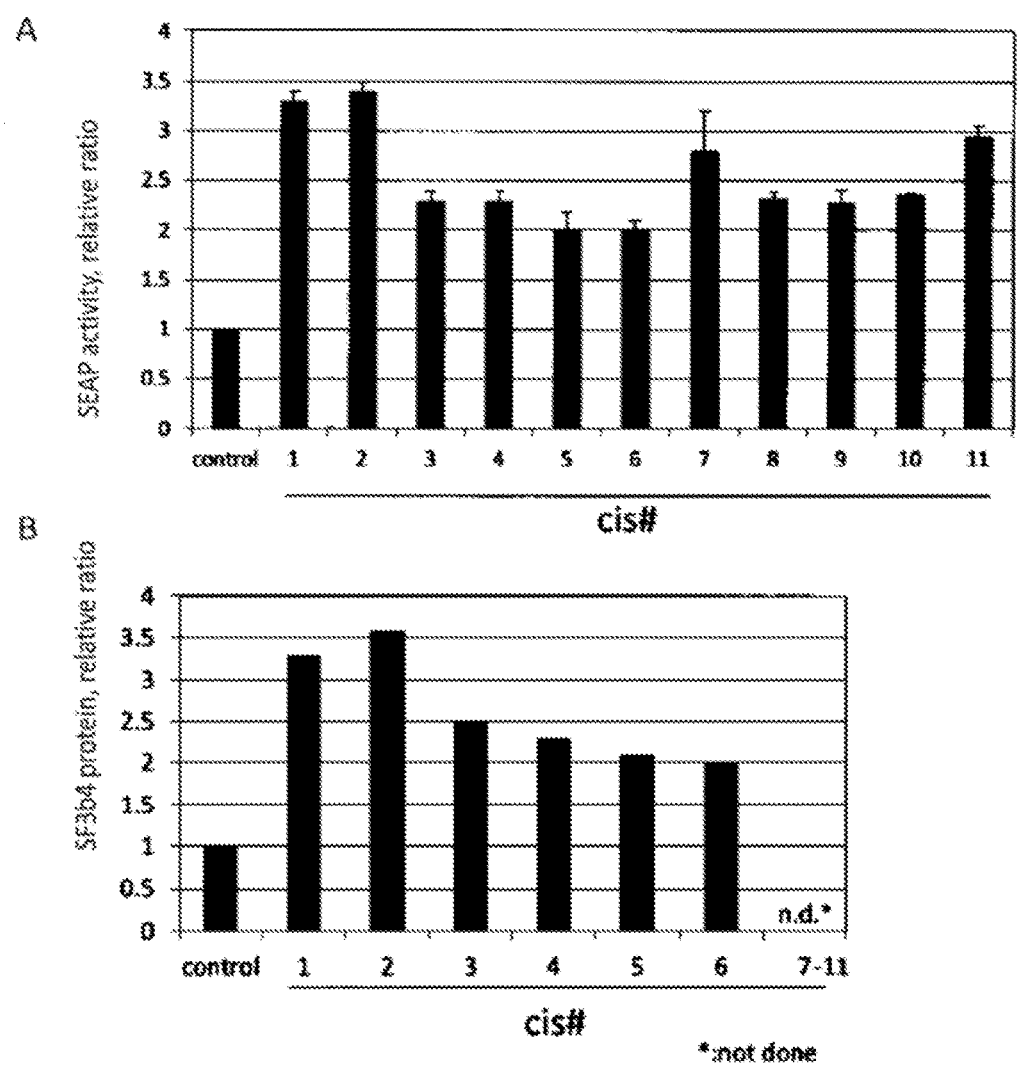
FIG. 8 shows the relationship of cis-element structure with protein expression enhancement effect, using cis-element #1, cis-element #2, cis-element #3, and cis-element #4.

The thus-obtained plasmids prCMV-cis#1-SEAP, prCMV-cis#2-SEAP, prCMV-cis#3-SEAP, prCMV-cis#4-SEAP, prCMV-cis#5-SEAP, prCMV-cis#6-SEAP, prCMV-cis#7-SEAP, prCMV-cis#8-SEAP, prCMV-cis#9-SEAP, prCMV-cis#10-SEAP, prCMV-cis#11-SEAP, and prCMV-SEAP were each transfected into the CHO YA7 cells, and after the culture for 20 hours, SEAP activity in culture supernatant was measured according to the procedure described in Example 5. As compared to the SEAP activity in the case of using prCMV-SEAP, which was taken as 1, the SEAP secretory activity ratio was increased by about 2.0 to 3.4 times with all the cis-elements used (FIG. 8A). In this process, the SF3b4 protein content in membrane fraction was analyzed by Western blotting and quantified by densitometry; then, it was found that in the cases of using cis-element #1, cis-element #2, cis-element #3, cis-element #4, cis-element #5, and cis-element #6, the SF3b4 protein content in membrane fraction increased significantly by 2.0 to 3.6 times as compared to the control (FIG. 8B).

These results showed that SF3b4 protein with a protein expression enhancement effect can be localized onto an endoplasmic reticulum membrane by adding each of cis-elements #1 to #11 to an expression unit, and that the secretory capacity in cells can be enhanced through this localization process.

Example 10: Effect of the Chain Length of Intra-Motif Sequence

The motif sequence $GAN_1-(X)_n-ACN_2$ identified in cis-element #1 was investigated for an effective chain length n by the following procedure. Different cis-element #3-derived variants of $GAG-(X)_n-ACV$ (V represents A, G or C) with n being varied from 1 to 9(mer) were constructed according to the same procedure as in Example 8 (FIG. 9A). Also constructed was a motif-deficient variant (motif delete). For the purpose of evaluating the SEAP secretory activities of the different elements, analysis of their secretion activities was made according to the procedure described in Example 5. According to the results of this analysis, a comparable activity to that of cis-element #3 was obtained in the cases of n=3 to 6 (FIG. 9B). Hence, it was found that the chain-X length n of the motif $GAN_1-(X)_n-ACN_2$ in a cis-element, which plays an important role in the activation of secretion in this system, ranges from 3 to 6 residues.

Example 11: Influences of Nucleotide Substitutions/Insertions in Motif Sequence Investigation was made of the influences of nucleotide substitutions and insertions in a motif on expression enhancement activity. Different cis-element #3-derived variants composed of the motif $GAN_1-(X)_n-ACN_2$ in cis-element #3, wherein $N_1$ and $N_2$ are independently A, G, C or T, were constructed by the same procedure as in Example 8 (FIG. 10A). Also constructed were other variants in which the motif was inserted into the polyA sequence or the polyC sequence, as well as control variants (FIG. 10A). The secretory activities of the different elements were analyzed according to the procedure described in Example 5. According to the results of this analysis, a comparable SEAP activity to that of cis-element #3 was obtained in all the cases where $N_2$ in cis-element #3 was substituted from G to A or C or T (FIG. 10B). Likewise, a comparable SEAP activity to that of cis-element #3 was obtained in all the cases where $N_1$ in cis-element #3 was substituted from G to A or C or T (FIG. 10B). Furthermore, the element having the motif inserted thereinto also had a comparable activity to that of cis-element #3. Hence, it was demonstrated that the motif having high activity is $GAN_1-(X)_n-ACN_2$ (wherein $N_1$ and $N_2$ can be independently any of the nucleotides A, T, C and G, and n is an integer of 3 to 6).

Example 12: Decrease in Collagen Secretion in Association with Expression Suppression of SF3b4

Figures 11, 12:
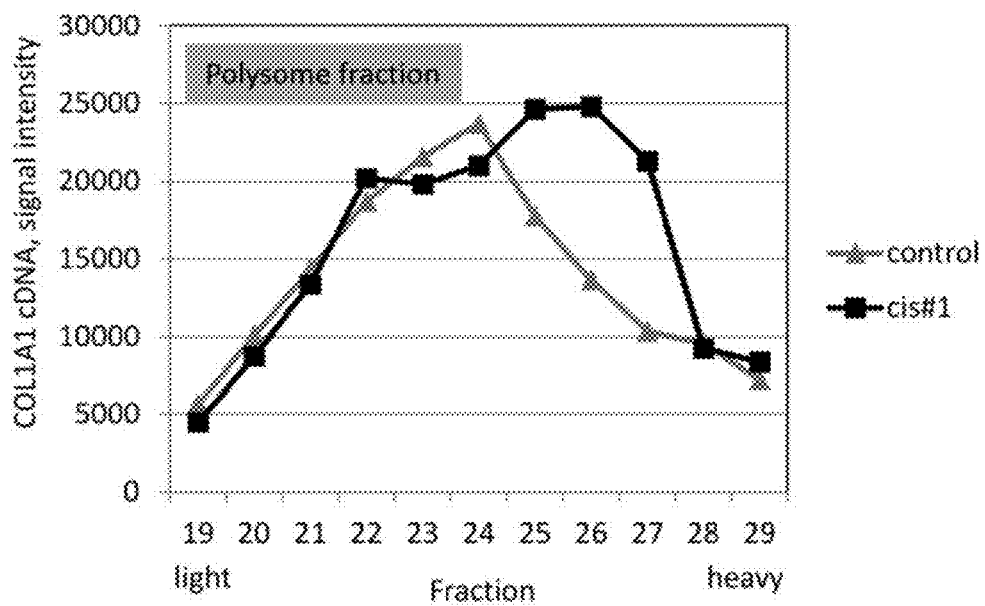
FIG. 11 shows that collagen production is remarkably suppressed through suppression of SF3b4 expression.
FIG. 12 shows that the COL1A1 cDNA weight in polysome fraction shifted towards higher density fractions in the presence of a cis-element as compared to the absence of a cis-element.

Investigation was made of the influence of SF3b4 expression suppression on collagen secretion. First, siRNA directed against SF3b4 (Life Technologies, human SF3b4 siRNA HSS115684) was transfected into human embryonic lung (HEL) fibroblasts according to the standard protocol for the Oligofectamine reagent (produced by Life Technologies). The transfected cells were cultured for 4 days under the condition of DMEM supplemented with 0.1% FBS and 200 μM ascorbic acid phosphate ester. Then, the medium was harvested, and the COL1A1 procollagen content in culture supernatant and the SF3b4 protein content in cell fractions were analyzed according to the procedure described in Example 6. According to the results of this analysis, when the amount of SF3b4 expressed intracellularly decreased to 20% of the control, the secreted COL1A1 procollagen amount decreased to 10% (FIG. 11). Hence, it was demonstrated that collagen production is remarkably suppressed through suppression of SF3b4 expression.

Example 13: Influence of a p180/SF3b4-Coexpressing Suspension Cell Line on Collagen Secretion A CHO-S cell line stably coexpressing human p180 protein and human SF3b4 protein was established according to the procedure described below. First, pCDNA-p180/54R was transfected into CHO-S cells (produced by Life Technologies) by a lipofection method, and the transfected cells were cultured for 14 days in the presence of 300 μg/mL of zeocin, whereby drug selection was done. After zeocin-resistant cell line colonies were isolated, pEF-SF3b4 was transfected by a lipofection method, and drug selection was done under the condition of 600 μg/mL hygromycin. After the culture for 14 days, cell line colonies resistant to both zeocin and hygromycin were isolated to establish the CHO-S-derived cell line 54#160 which stably coexpresses human p180 protein and human SF3b4 protein.

The plasmids prCMV-COL1A1 and prCMV-COL1A1-ORF were each transfected by a lipofection method into each of the control CHO-S cells and the prepared 54#160 cells. The transfected cells were cultured for 96 hours in a serum-free CD FortiCHO medium supplemented with 8 mM L-glutamine (Life Technologies), and then the COL1A1 procollagen content in culture supernatant was analyzed by Western blotting. In the case of genetic introduction of prCMV-COL1A1 containing cis-element #1, the procollagen content in the 54#160 cells increased by about 3.5 times as compared to that in the control CHO-S cells, which was taken as 1. In the case of genetic introduction of prCMV-COL1A1-ORF not containing cis-element #1, the procollagen content in culture supernatant was below the limit of detection by Western blotting.

Hence, it was demonstrated that cis-element #1 is capable of enhancing the synthesis/secretion of collagen macromolecules in suspended CHO-S cells under a serum-free condition, and that the secretory activity of suspended CHO cells can be more remarkably enhanced by the three factors cis-element #1, SF3b4 protein and p180 protein.

Example 14: Shift of mRNA Distribution in Polysome Towards Heavier Fractions by Cis-Element #1

The plasmids prCMV-COL1A1 and prCMV-COL1A1-ORF were each transfected by a lipofection method into the CHO YA7 cells. After 40 hours, respective membrane fractions were prepared according to the procedure described in Example 3. The resultant membrane fractions were subjected to centrifugation with a sucrose density gradient from 15 to 50% sucrose to fractionate them into a polysome fraction. mRNA was extracted from each of the resultant polysome fractions according to the procedure described in Example 5, and COL1A1 cDNA was quantified by quantitative PCR. Also, the amount of procollagen then secreted was analyzed by the procedure described in Example 6. According to the results of this analysis, the COL1A1 cDNA distribution in polysome fraction showed a peak at fraction 24 in the case of prCMV-COL1A1-ORF not containing a cis-element, and at fraction 26 in the presence of cis#1, which indicated a shift of the distribution towards heavier fractions (FIG. 12). In addition, with the shift of peak, the secreted procollagen amount increased by 4.9 times over the control in the presence of cis-element #1. It was demonstrated that cis-element #1, in the presence of p180 and SF3b4, shows a capability of inducing a shift of mRNA distribution towards heavier fractions, which correlates with an increase in expression.

INDUSTRIAL APPLICABILITY

It was found that, in the recombinant cell of the present invention which has enhanced expression of the full length or a portion of p180 protein and the full length or a portion of SF3b4 protein, a DNA encoding a protein as a product of interest is transformed, whereby a synthetic or secretory capacity of the protein as a product of interest is dramatically enhanced.

SEQUENCE LISTING FREE TEXT

SEQ ID NO: 1: Nucleotide sequence encoding human p180

SEQ ID NO: 2: Amino acid sequence of human p180 protein

SEQ ID NO: 3: Nucleotide sequence encoding human SF3b4

SEQ ID NO: 4: Amino acid sequence of human SF3b4 protein

SEQ ID NO: 5: cis-element #1

SEQ ID NO: 6: cis-element #2

SEQ ID NO: 7: cis-element #3

SEQ ID NO: 8: cis-element #4

SEQ ID NO: 9: cis-element-containing primer designed for cis-element #3

SEQ ID NO: 10: cis-element-containing primer designed for cis-element #3

SEQ ID NO: 11: cis-element-containing primer designed for cis-element #4

SEQ ID NO: 12: cis-element-containing primer designed for cis-element #4

SEQ ID NO: 13: cis-element-containing primer designed for cis-element #2, in which the BglII recognition sequence is added towards the 5' end SEQ ID NO: 14: cis-element-containing primer designed for cis-element #2, in which the HindIII recognition sequence is added towards the 3' end SEQ ID NO: 15: Primer for amplifying cis-element #1, in which the BglII recognition sequence is added towards the 5' end SEQ ID NO: 16: Primer for amplifying cis-element #1, in which the HindIII recognition sequence is added towards the 3' end SEQ ID NO: 17: Motif in cis-element (9mer)

SEQ ID NO: 18: Motif in cis-element (10mer)

SEQ ID NO: 19: Motif in cis-element (11mer)

SEQ ID NO: 20: Motif in cis-element (12mer)

SEQ ID NO: 21: cis-element #5

SEQ ID NO: 22: cis-element #6

SEQ ID NO: 23: cis-element #7

SEQ ID NO: 24: cis-element #8

SEQ ID NO: 25: cis-element #9

SEQ ID NO: 26: cis-element #10

SEQ ID NO: 27: cis-element #11

SEQ ID NO: 28: cis-element-containing primer designed for cis-element #5, in which the BglII recognition sequence is added towards the 5' end SEQ ID NO: 29: cis-element-containing primer designed for cis-element #5, in which the HindIII recognition sequence is added towards the 3' end SEQ ID NO: 30: cis-element-containing primer designed for cis-element #6, in which the BglII recognition sequence is added towards the 5' end SEQ ID NO: 31: cis-element-containing primer designed for cis-element #6, in which the HindIII recognition sequence is added towards the 3' end SEQ ID NO: 32: cis-element-containing primer designed for cis-element #8

SEQ ID NO: 33: cis-element-containing primer designed for cis-element #8

SEQ ID NO: 34: cis-element-containing primer designed for cis-element #9

SEQ ID NO: 35: cis-element-containing primer designed for cis-element #9

SEQ ID NO: 36: cis-element-containing primer designed for cis-element #10

SEQ ID NO: 37: cis-element-containing primer designed for cis-element #10

SEQ ID NO: 38: cis-element-containing primer designed for cis-element #11, in which the BglII recognition sequence is added towards the 5' end SEQ ID NO: 39: cis-element-containing primer designed for cis-element #11, in which the HindIII recognition sequence is added towards the 3' end.

The invention claimed is:

1. A method for increasing an amount of a protein product of interest expressed in a cell expression system comprising inserting a cis-element recognized by or interacting with an RNA-binding protein in an expression unit for expressing the protein product of interest,
wherein the expression unit comprises a cDNA encoding a protein product of interest consisting of a nucleic acid sequence encoding the full-length of the protein product of interest,
wherein the cis-element is inserted downstream of a promoter and upstream of a start codon of the cDNA encoding the protein product of interest, whereby the amount of the protein product of interest expressed in the cell expression system is increased,
wherein the cis-element comprises two or more motifs consisting of a nucleotide sequence containing 9mer to 12mer sequence of GAN1-(X)n-ACN2, wherein n=3 to 6, N1 and N2 are independently selected from adenine (A), thymine (T), cytosine (C), or guanine (G), and X is selected from adenine (A), thymine (T), cytosine (C), or guanine (G),
wherein the RNA-binding protein is
(1) a protein consisting of an amino acid sequence of splicing factor 3B subunit 4 (SF3b4) set forth in SEQ ID NO: 4;
(2) a protein consisting of an amino acid sequence with at least 90% sequence identity to the amino acid sequence set forth in SEQ ID NO: 4, and which, when expressed in the cell, has an ability to enhance capacity of the cell for synthesis or secretion of the protein product of interest, wherein the ability is comparable to that of SF3b4 having the amino acid sequence set forth in SEQ ID NO: 4; or (3) a protein consisting of an amino acid sequence encoded by a nucleotide sequence with at least 90% sequence identity to the nucleotide sequence set forth in SEQ ID NO: 3, and which, when expressed in the cell, has an ability to enhance capacity of the cell for synthesis or secretion of the protein product of interest, wherein the ability is comparable to that of SF3b4 having the amino acid sequence set forth in SEQ ID NO: 4; and wherein the cell expression system is a recombinant cell transfected with a nucleic acid encoding an RNA-binding protein containing an RNA recognition motif (RRM) and a nucleic acid encoding a p180 protein, wherein said transfection provides for enhanced intracellular synthetic or secretory capacity of a protein product of interest.

2. The method according to claim 1, wherein the cis-element comprises (i) a nucleotide sequence containing 9mer to 12mer sequence motifs of GAG-(X)n-ACV, wherein n=3 to 6 and V is A, G, or C; and (ii) a nucleotide sequence set forth in one of SEQ ID NOs: 17 to 20.

3. The method according to claim 1, wherein the cis-element comprises a sequence selected from the group consisting of: a sequence derived from the nucleotide sequence of the 5' untranslated region of a type I collagen gene; a sequence derived from the nucleotide sequence of the 5' untranslated region of a fibronectin gene; a sequence derived from the nucleotide sequence of the 5' untranslated region of a matrix metalloproteinase 14 (MMP14) gene; and a sequence derived from the nucleotide sequence of the 5' untranslated region of a prolyl 4-hydroxylase A2 (P4HA2) gene.

4. The method according to claim 1, wherein the cis-element comprises SEQ ID NO: 5, or nucleotides at positions 1 to 102, positions 1 to 78, positions 1 to 60, positions 61 to 126, positions 16 to 57, positions 79 to 126, positions 103 to 126, positions 58 to 78, positions 51 to 78, positions 1 to 27, or positions 70 to 78 of SEQ ID NO: 5.

5. The method according to claim 1, wherein the cell expression system comprises a cis-element comprising four of the motifs.

6. A method for increasing an amount of a protein product of interest expressed in a cell expression system comprising:
(a) inserting a cis-element recognized by or interacting with an RNA-binding protein in an expression unit for expressing the protein product of interest, wherein the cis-element is inserted downstream of a promoter and upstream of a start codon in a nucleotide sequence encoding the protein product of interest, whereby the amount of the protein product of interest expressed in the cell expression system is increased,
wherein the cis-element comprises one or more motif(s) consisting of a nucleotide sequence containing 9mer to 12mer sequence of GAN1-(X)n-ACN2, wherein n=3 to 6, N1 and N2 are independently selected from adenine (A), thymine (T), cytosine (C), or guanine (G), and X is selected from adenine (A), thymine (T), cytosine (C), or guanine (G), and
(b) expressing the protein product of interest in the cell expression system, wherein the cell expression system is a recombinant cell transfected with a nucleic acid encoding an RNA-binding protein containing an RNA recognition motif (RRM) and transfected with both a nucleic acid encoding a p180 protein, wherein the RNA-binding protein is
(1) a protein consisting of an amino acid sequence of splicing factor 3B subunit 4 (SF3b4) set forth in SEQ ID NO: 4;
(2) a protein consisting of an amino acid sequence with at least 90% sequence identity to the amino acid sequence set forth in SEQ ID NO: 4, and which, when expressed in the cell, has an ability to enhance capacity of the cell for synthesis or secretion of the protein product of interest, wherein the ability is comparable to that of SF3b4 having the amino acid sequence set forth in SEQ ID NO: 4; or
(3) a protein consisting of an amino acid sequence encoded by a nucleotide sequence with at least 90% sequence identity to the nucleotide sequence set forth in SEQ ID NO: 3, and which, when expressed in the cell, has an ability to enhance capacity of the cell for synthesis or secretion of the protein product of interest, wherein the ability is comparable to that of SF3b4 having the amino acid sequence set forth in SEQ ID NO: 4.

7. An expression unit for expressing a protein product of interest comprising
(a) a cDNA encoding a protein product of interest consisting of a nucleic acid sequence encoding the full-length of the protein product of interest, and
(b) a cis-element recognized by or bound by an RNA-binding protein,
wherein the cis-element is inserted into the expression unit downstream of a promoter and and upstream of a start codon of the cDNA encoding the protein product of interest, whereby the amount of the protein product of interest expressed in a cell expression system is increased,
wherein the cis-element comprises two or more motifs consisting of a nucleotide sequence containing 9mer to 12mer sequence of GAN1-(X)n-ACN2, wherein n=3 to 6, N1 and N2 are independently selected from adenine (A), thymine (T), cytosine (C), or guanine (G), and X is selected from adenine (A), thymine (T), cytosine (C), or guanine (G),
wherein the RNA-binding protein is
(1) a protein consisting of an amino acid sequence of splicing factor 3B subunit 4 (SF3b4) set forth in SEQ ID NO: 4;
(2) a protein consisting of an amino acid sequence with at least 90% sequence identity to the amino acid sequence set forth in SEQ ID NO:4, and which, when expressed in the cell, has an ability to enhance capacity of the cell for synthesis or secretion of the protein product of interest, wherein the ability is comparable to that of SF3b4 having the amino acid sequence set forth in SEQ ID NO: 4; or
(3) a protein consisting of an amino acid sequence encoded by a nucleotide sequence with at least 90% sequence identity to the nucleotide sequence set forth in SEQ ID NO: 3, and which, when expressed in the cell, has an ability to enhance capacity of the cell for synthesis or secretion of the protein product of interest, wherein the ability is comparable to that of SF3b4 having the amino acid sequence set forth in SEQ ID NO: 4; and
wherein the cell expression system is a recombinant cell transfected with a nucleic acid encoding an RNA-binding protein containing an RNA recognition motif (RRM) and a nucleic acid encoding a p180 protein, wherein said transfection provides for enhanced intracellular synthetic or secretory capacity of a protein product of interest.

8. An expression vector comprising the expression unit according to claim 7.

9. The expression unit according to claim 7 comprising a cis-element comprising four of the motifs.

10. An expression unit for expressing a protein product of interest comprising
(a) a cDNA encoding a protein product of interest consisting of a nucleic acid sequence encoding the full-length of the protein product of interest, and
(b) a cis-element recognized by or bound by an RNA-binding protein,
wherein the cis-element is inserted into the expression unit downstream of a promoter and upstream of a start codon of the cDNA encoding the protein product of interest, whereby the amount of the protein product of interest expressed in a cell expression system is increased,
wherein the cis-element comprises one or more motif(s) consisting of a nucleotide sequence containing 9mer to 12mer sequence of GAN1-(X)n-ACN2, wherein n=3 to 6, N1 and N2 are independently selected from adenine (A), thymine (T), cytosine (C), or guanine (G), and X is selected from adenine (A), thymine (T), cytosine (C), or guanine (G),
wherein the RNA-binding protein is
(1) a protein consisting of an amino acid sequence of splicing factor 3B subunit 4 (SF3b4) set forth in SEQ ID NO: 4;
(2) a protein consisting of an amino acid sequence with at least 90% sequence identity to the amino acid sequence set forth in SEQ ID NO: 4, and which, when expressed in the cell, has an ability to enhance capacity of the cell for synthesis or secretion of the protein product of interest, wherein the ability is comparable to that of SF3b4 having the amino acid sequence set forth in SEQ ID NO: 4; or
(3) a protein consisting of an amino acid sequence encoded by a nucleotide sequence with at least 90% sequence identity to the nucleotide sequence set forth in SEQ ID NO: 3, and which, when expressed in the cell, has an ability to enhance capacity of the cell for synthesis or secretion of the protein product of interest, wherein the ability is comparable to that of SF3b4 having the amino acid sequence set forth in SEQ ID NO: 4; wherein the cell expression system is a recombinant cell transfected with a nucleic acid encoding an RNA-binding protein containing an RNA recognition motif (RRM) and transfected with both a nucleic acid encoding a p180 protein, wherein said transfection provides for enhanced intracellular synthetic or secretory capacity of a protein product of interest; and
wherein the expression unit comprises a cDNA encoding a protein product of interest consisting of a nucleic acid sequence encoding the full-length of the protein product of interest.

11. An expression vector comprising an expression unit for expressing a protein product of interest comprising
(a) a cDNA encoding a protein product of interest consisting of a nucleic acid sequence encoding the full-length of the protein product of interest, and
(b) a cis-element recognized by or bound by an RNA-binding protein,
wherein the cis-element is inserted into the expression unit downstream of a promoter and upstream of a start codon of the cDNA encoding the protein product of interest, whereby the amount of the protein product of interest expressed in a cell expression system is increased,
wherein the cis-element comprises one or more motif(s) consisting of a nucleotide sequence containing 9mer to 12mer sequence of GAN1-(X)n-ACN2, wherein n=3 to 6, N1 and N2 are independently selected from adenine (A), thymine (T), cytosine (C), or guanine (G), and X is selected from adenine (A), thymine (T), cytosine (C), or guanine (G),
wherein the RNA-binding protein is
(1) a protein consisting of an amino acid sequence of splicing factor 3B subunit 4 (SF3b4) set forth in SEQ ID NO: 4;
(2) a protein consisting of an amino acid sequence with at least 90% sequence identity to the amino acid sequence set forth in SEQ ID NO: 4, and which, when expressed in the cell, has an ability to enhance capacity of the cell for synthesis or secretion of the protein product of interest, wherein the ability is comparable to that of SF3b4 having the amino acid sequence set forth in SEQ ID NO: 4; or
(3) a protein consisting of an amino acid sequence encoded by a nucleotide sequence with at least 90% sequence identity to the nucleotide sequence set forth in SEQ ID NO: 3, and which, when expressed in the cell, has an ability to enhance capacity of the cell for synthesis or secretion of the protein product of interest, wherein the ability is comparable to that of SF3b4 having the amino acid sequence set forth in SEQ ID NO: 4; wherein the cell expression system is a recombinant cell transfected with a nucleic acid encoding an RNA-binding protein containing an RNA recognition motif (RRM) and transfected with both a nucleic acid encoding a p180 protein, wherein said transfection provides for enhanced intracellular synthetic or secretory capacity of a protein product of interest; and
wherein the expression unit comprises a cDNA encoding a protein product of interest consisting of a nucleic acid sequence encoding the full-length of the protein product of interest.

\* \* \* \* \*

SEQUENCE LISTING

```
<160> NUMBER OF SEQ ID NOS: 48

<210> SEQ ID NO 1
<211> LENGTH: 4623
<212> TYPE: DNA
<213> ORGANISM: Homo sapiens
<220> FEATURE:
<221> NAME/KEY: CDS
<222> LOCATION: (1)..(4623)

<400> SEQUENCE: 1 atg gat att tac gac act caa acc ttg ggg gtt gtg gtc ttt gga gga     48
Met Asp Ile Tyr Asp Thr Gln Thr Leu Gly Val Val Val Phe Gly Gly
1               5                   10                  15 ttc atg gtt gtt tct gcc att ggc atc ttc ctg gtg tcg act ttc tcc     96
Phe Met Val Val Ser Ala Ile Gly Ile Phe Leu Val Ser Thr Phe Ser
            20                  25                  30
```

-continued

| | | |
|---|---|---|
| atg aag gaa acg tca tat gaa gaa gcc cta gcc aac cag cgc aag gag<br>Met Lys Glu Thr Ser Tyr Glu Glu Ala Leu Ala Asn Gln Arg Lys Glu<br>35 40 45 | | 144 |
| atg gcg aaa act cac cac cag aaa gtc gag aag aaa aag aag gag aaa<br>Met Ala Lys Thr His His Gln Lys Val Glu Lys Lys Lys Lys Glu Lys<br>50 55 60 | | 192 |
| aca gtg gag aag aaa gga aag acc aag aaa aag gaa gag aaa cct aat<br>Thr Val Glu Lys Lys Gly Lys Thr Lys Lys Lys Glu Glu Lys Pro Asn<br>65 70 75 80 | | 240 |
| ggg aag ata cct gat cat gat cca gcc ccc aat gtg act gtc ctc ctt<br>Gly Lys Ile Pro Asp His Asp Pro Ala Pro Asn Val Thr Val Leu Leu<br>85 90 95 | | 288 |
| cga gaa cca gtg cgg gct cct gct gtg gct gtg gct cca acc cca gtg<br>Arg Glu Pro Val Arg Ala Pro Ala Val Ala Val Ala Pro Thr Pro Val<br>100 105 110 | | 336 |
| cag ccc ccc att atc gtt gct cct gtc gcc aca gtt cca gcc atg ccc<br>Gln Pro Pro Ile Ile Val Ala Pro Val Ala Thr Val Pro Ala Met Pro<br>115 120 125 | | 384 |
| cag gag aag ctg gcc tcc tcc ccc aag gac aaa aag aag aag gag aaa<br>Gln Glu Lys Leu Ala Ser Ser Pro Lys Asp Lys Lys Lys Lys Glu Lys<br>130 135 140 | | 432 |
| aaa gtg gca aaa gtg gaa cca gct gtc agc tct gta gtg aat tcc atc<br>Lys Val Ala Lys Val Glu Pro Ala Val Ser Ser Val Val Asn Ser Ile<br>145 150 155 160 | | 480 |
| cag gtt ctc act tcg aag gct gcc atc ttg gaa act gct ccc aag gag<br>Gln Val Leu Thr Ser Lys Ala Ala Ile Leu Glu Thr Ala Pro Lys Glu<br>165 170 175 | | 528 |
| gtg ccg atg gtg gtg gtg ccc cca gtg ggt gcc aag ggc aac aca cca<br>Val Pro Met Val Val Val Pro Pro Val Gly Ala Lys Gly Asn Thr Pro<br>180 185 190 | | 576 |
| gcc act ggc act act cag ggc aaa aag gcg gag ggg act cag aat caa<br>Ala Thr Gly Thr Thr Gln Gly Lys Lys Ala Glu Gly Thr Gln Asn Gln<br>195 200 205 | | 624 |
| agc aaa aag gct gaa gga gcc cca aac cag ggc aga aag gca gag gga<br>Ser Lys Lys Ala Glu Gly Ala Pro Asn Gln Gly Arg Lys Ala Glu Gly<br>210 215 220 | | 672 |
| acc cca aac cag ggc aaa aag aca gag gga acc cca aac caa ggg aaa<br>Thr Pro Asn Gln Gly Lys Lys Thr Glu Gly Thr Pro Asn Gln Gly Lys<br>225 230 235 240 | | 720 |
| aag gca gag gga acc cca aac caa ggc aaa aag gca gaa gga acc cca<br>Lys Ala Glu Gly Thr Pro Asn Gln Gly Lys Lys Ala Glu Gly Thr Pro<br>245 250 255 | | 768 |
| aac caa ggc aaa aag gcg gag ggg gcc cag aac cag ggt aaa aag gta<br>Asn Gln Gly Lys Lys Ala Glu Gly Ala Gln Asn Gln Gly Lys Lys Val<br>260 265 270 | | 816 |
| gat aca acc cca aac cag ggg aaa aag gtg gag ggg gcc cca acc cag<br>Asp Thr Thr Pro Asn Gln Gly Lys Lys Val Glu Gly Ala Pro Thr Gln<br>275 280 285 | | 864 |
| ggc aga aag gcc gag ggg gct cag aac cag gcc aaa aag gta gaa ggg<br>Gly Arg Lys Ala Glu Gly Ala Gln Asn Gln Ala Lys Lys Val Glu Gly<br>290 295 300 | | 912 |
| gcc cag aac cag ggc aaa aag gca gag ggg gcc cag aat cag ggc aaa<br>Ala Gln Asn Gln Gly Lys Lys Ala Glu Gly Ala Gln Asn Gln Gly Lys<br>305 310 315 320 | | 960 |
| aag gga gag ggg gcc cag aac cag ggc aag aag gcc gag ggg gcc cag<br>Lys Gly Glu Gly Ala Gln Asn Gln Gly Lys Lys Ala Glu Gly Ala Gln<br>325 330 335 | | 1008 |
| aat cag ggc aag aag gcc gag ggg gcc cag aat cag ggc aag aag gcc<br>Asn Gln Gly Lys Lys Ala Glu Gly Ala Gln Asn Gln Gly Lys Lys Ala<br>340 345 350 | | 1056 |

-continued

| | |
|---|---|
| gag ggg gcc cag aat cag ggc aag aag gcc gag ggg gcc cag aat cag<br>Glu Gly Ala Gln Asn Gln Gly Lys Lys Ala Glu Gly Ala Gln Asn Gln<br>355                         360                      365 | 1104 |
| ggc aag aag gct gag ggg gct cag aac cag ggc aaa aag gcc gag ggg<br>Gly Lys Lys Ala Glu Gly Ala Gln Asn Gln Gly Lys Lys Ala Glu Gly<br>370                       375                   380 | 1152 |
| gct cag aac cag ggc aaa aaa gta gaa ggg gcc cag aac cag ggc aag<br>Ala Gln Asn Gln Gly Lys Lys Val Glu Gly Ala Gln Asn Gln Gly Lys<br>385                   390                   395                 400 | 1200 |
| aag gct gag ggt gcc cag aac cag ggc aaa aag gcc gag ggg gcc cag<br>Lys Ala Glu Gly Ala Gln Asn Gln Gly Lys Lys Ala Glu Gly Ala Gln<br>                     405                   410                   415 | 1248 |
| aat cag ggc aaa aag gcc gag ggg gcc cag aac cag ggc aag aag gca<br>Asn Gln Gly Lys Lys Ala Glu Gly Ala Gln Asn Gln Gly Lys Lys Ala<br>         420                   425                   430 | 1296 |
| gag ggg gcc cag aac cag ggc aag aag gcc gag ggg gcc cag aac cag<br>Glu Gly Ala Gln Asn Gln Gly Lys Lys Ala Glu Gly Ala Gln Asn Gln<br>435                       440                     445 | 1344 |
| gac aag aag gcc gag ggg gcc cag aac cag ggc agg aag gcc gag ggg<br>Asp Lys Lys Ala Glu Gly Ala Gln Asn Gln Gly Arg Lys Ala Glu Gly<br>450                       455                   460 | 1392 |
| gcc cag aac cag ggc agg aag gcc gag ggg gcc cag aac cag ggc aag<br>Ala Gln Asn Gln Gly Arg Lys Ala Glu Gly Ala Gln Asn Gln Gly Lys<br>465                       470                   475                 480 | 1440 |
| aag gcc gag ggg gcc cag aac cag ggc aag aag gcc gag ggg acc ccg<br>Lys Ala Glu Gly Ala Gln Asn Gln Gly Lys Lys Ala Glu Gly Thr Pro<br>                     485                   490                   495 | 1488 |
| aac cag ggc aag aag gcc gag ggg acc ccg aac cag ggc aag aag gcc<br>Asn Gln Gly Lys Lys Ala Glu Gly Thr Pro Asn Gln Gly Lys Lys Ala<br>         500                   505                   510 | 1536 |
| gag ggg gcc cag aac cag ggc aag aag gcc gag ggg gcc cag aac cag<br>Glu Gly Ala Gln Asn Gln Gly Lys Lys Ala Glu Gly Ala Gln Asn Gln<br>515                       520                   525 | 1584 |
| ggc aag aag gcc gag ggg acc ccg aac cag ggc aag aag gcc gag ggg<br>Gly Lys Lys Ala Glu Gly Thr Pro Asn Gln Gly Lys Lys Ala Glu Gly<br>530                       535                   540 | 1632 |
| gcc cag aac cag ggc aag aag gcc gag ggg gcc cag aac cag ggc aag<br>Ala Gln Asn Gln Gly Lys Lys Ala Glu Gly Ala Gln Asn Gln Gly Lys<br>545                       550                   555                 560 | 1680 |
| aag gcc gag ggg gcc cag aac cag ggc aag aag gcc gag ggg gcc cag<br>Lys Ala Glu Gly Ala Gln Asn Gln Gly Lys Lys Ala Glu Gly Ala Gln<br>                     565                   570                   575 | 1728 |
| aac cag ggc aag aag gcc gag ggg gcc cag aac cag ggc aag aag gcc<br>Asn Gln Gly Lys Lys Ala Glu Gly Ala Gln Asn Gln Gly Lys Lys Ala<br>         580                   585                   590 | 1776 |
| gag ggt gct cag aac cag ggc aaa aaa gta gaa ggg gcc cag aac cag<br>Glu Gly Ala Gln Asn Gln Gly Lys Lys Val Glu Gly Ala Gln Asn Gln<br>595                       600                   605 | 1824 |
| ggc aag aag gct gag ggg gcc cag aac cag ggc aag aag gcc gag ggg<br>Gly Lys Lys Ala Glu Gly Ala Gln Asn Gln Gly Lys Lys Ala Glu Gly<br>610                       615                   620 | 1872 |
| gct cag aac cag ggc aaa aag gcc gag gga gcc cag aac cag ggc caa<br>Ala Gln Asn Gln Gly Lys Lys Ala Glu Gly Ala Gln Asn Gln Gly Gln<br>625                       630                   635                 640 | 1920 |
| aaa gga gag gga gcc cag aat cag ggt aaa aag aca gaa ggg gct cag<br>Lys Gly Glu Gly Ala Gln Asn Gln Gly Lys Lys Thr Glu Gly Ala Gln<br>                     645                   650                   655 | 1968 |
| ggc aaa aag gca gaa agg agt ccc aac caa ggc aaa aaa gga gag gga<br>Gly Lys Lys Ala Glu Arg Ser Pro Asn Gln Gly Lys Lys Gly Glu Gly<br>         660                   665                   670 | 2016 |

```
                                         -continued
gct ccc atc cag ggc aaa aag gca gat tcg gtt gct aat cag ggc aca       2064
Ala Pro Ile Gln Gly Lys Lys Ala Asp Ser Val Ala Asn Gln Gly Thr
            675                 680                 685 aag gta gag ggt att aca aac cag ggg aaa aaa gca gaa ggg tcc ccc       2112
Lys Val Glu Gly Ile Thr Asn Gln Gly Lys Lys Ala Glu Gly Ser Pro
            690                 695                 700 agt gaa ggc aaa aag gca gaa ggg tcc ccc aac caa ggc aaa aag gca       2160
Ser Glu Gly Lys Lys Ala Glu Gly Ser Pro Asn Gln Gly Lys Lys Ala
705                 710                 715                 720 gac gca gct gcc aat cag ggt aaa aag aca gag tca gct tct gtc cag       2208
Asp Ala Ala Ala Asn Gln Gly Lys Lys Thr Glu Ser Ala Ser Val Gln
                725                 730                 735 ggc aga aat aca gat gtg gcc cag agc cca gag gca cca aag caa gag       2256
Gly Arg Asn Thr Asp Val Ala Gln Ser Pro Glu Ala Pro Lys Gln Glu
            740                 745                 750 gct cct gcc aag aag aag tct ggt tca aag aaa aaa ggt gag cct ggg       2304
Ala Pro Ala Lys Lys Lys Ser Gly Ser Lys Lys Lys Gly Glu Pro Gly
            755                 760                 765 ccc cca gat gcc gac ggc cct ctc tac ctc ccc tac aag acg ctg gtc       2352
Pro Pro Asp Ala Asp Gly Pro Leu Tyr Leu Pro Tyr Lys Thr Leu Val
            770                 775                 780 tcc acg gtt ggg agc atg gtg ttc aac gag ggc gag gcc cag cgg ctc       2400
Ser Thr Val Gly Ser Met Val Phe Asn Glu Gly Glu Ala Gln Arg Leu
785                 790                 795                 800 atc gag atc ctg tcc gag aag gct ggc atc att cag gac acc tgg cac       2448
Ile Glu Ile Leu Ser Glu Lys Ala Gly Ile Ile Gln Asp Thr Trp His
                805                 810                 815 aag gcc act cag aag ggt gac cct gtg gcg att ctg aaa cgc cag ctg       2496
Lys Ala Thr Gln Lys Gly Asp Pro Val Ala Ile Leu Lys Arg Gln Leu
            820                 825                 830 gaa gag aag gaa aaa ctg ctg gcc aca gaa cag gaa gat gcg gct gtc       2544
Glu Glu Lys Glu Lys Leu Leu Ala Thr Glu Gln Glu Asp Ala Ala Val
            835                 840                 845 gcc aag agc aaa ctg agg gag ctc aac aag gag atg gca gca gaa aag       2592
Ala Lys Ser Lys Leu Arg Glu Leu Asn Lys Glu Met Ala Ala Glu Lys
            850                 855                 860 gcc aaa gca gca gcc ggg gag gcc aaa gtg aaa aag cag ctg gtg gcc       2640
Ala Lys Ala Ala Ala Gly Glu Ala Lys Val Lys Lys Gln Leu Val Ala
865                 870                 875                 880 cgg gag cag gag atc acg gct gtg cag gca cgc atg cag gcc agc tac       2688
Arg Glu Gln Glu Ile Thr Ala Val Gln Ala Arg Met Gln Ala Ser Tyr
                885                 890                 895 cgg gag cac gtg aag gag gtg cag cag ctg cag ggc aag atc cgg act       2736
Arg Glu His Val Lys Glu Val Gln Gln Leu Gln Gly Lys Ile Arg Thr
            900                 905                 910 ctt cag gag cag ctg gag aat ggc ccc aac acg cag ctg gcc cgc ctg       2784
Leu Gln Glu Gln Leu Glu Asn Gly Pro Asn Thr Gln Leu Ala Arg Leu
            915                 920                 925 cag cag gag aac tcc atc ctg cgg gat gcc ttg aac cag gcc acg agc       2832
Gln Gln Glu Asn Ser Ile Leu Arg Asp Ala Leu Asn Gln Ala Thr Ser
            930                 935                 940 cag gtg gag agc aag cag aac gca gag ctg gcc aag ctt cgg cag gag       2880
Gln Val Glu Ser Lys Gln Asn Ala Glu Leu Ala Lys Leu Arg Gln Glu
945                 950                 955                 960 ctc agc aag gtc agc aaa gag ctg gtg gag aag tca gag gct gtg cgg       2928
Leu Ser Lys Val Ser Lys Glu Leu Val Glu Lys Ser Glu Ala Val Arg
                965                 970                 975 caa gat gag cag cag cgg aaa gct ctg gaa gcc aag gca gct gcc ttc       2976
Gln Asp Glu Gln Gln Arg Lys Ala Leu Glu Ala Lys Ala Ala Ala Phe
            980                 985                 990
```

-continued

| | | |
|---|---|---|
| gag aag cag gtc ctg cag ctg cag gcg tcc cac agg gag agt gag gag<br>Glu Lys Gln Val Leu Gln Leu Gln Ala Ser His Arg Glu Ser Glu Glu<br>      995                          1000                        1005 | 3024 | |
| gcc ctg cag aag cgc ctg gac gag gtc agc cgg gag ctg tgc cac<br>Ala Leu Gln Lys Arg Leu Asp Glu Val Ser Arg Glu Leu Cys His<br>1010                        1015                          1020 | 3069 | |
| acg cag agc agc cac gcc agc ctc cgg gcg gat gcc gag aag gcc<br>Thr Gln Ser Ser His Ala Ser Leu Arg Ala Asp Ala Glu Lys Ala<br>1025                        1030                        1035 | 3114 | |
| cag gag caa cag cag cag atg gcc gag ctg cac agc aag tta cag<br>Gln Glu Gln Gln Gln Gln Met Ala Glu Leu His Ser Lys Leu Gln<br>1040                        1045                        1050 | 3159 | |
| tcc tcc gag gca gag gtg cgc agc aaa tgc gag gag ctg agt ggc<br>Ser Ser Glu Ala Glu Val Arg Ser Lys Cys Glu Glu Leu Ser Gly<br>1055                        1060                        1065 | 3204 | |
| ctc cac ggg cag ctc cag gag gcc agg gcg gag aac tcc cag ctc<br>Leu His Gly Gln Leu Gln Glu Ala Arg Ala Glu Asn Ser Gln Leu<br>1070                        1075                        1080 | 3249 | |
| aca gag aga atc cgt tcc att gag gcc ctg ctg gag gcg ggc cag<br>Thr Glu Arg Ile Arg Ser Ile Glu Ala Leu Leu Glu Ala Gly Gln<br>1085                        1090                        1095 | 3294 | |
| gcg cgg gat gcc cag gac gtc cag gcc agc cag gcg gag gct gac<br>Ala Arg Asp Ala Gln Asp Val Gln Ala Ser Gln Ala Glu Ala Asp<br>1100                        1105                        1110 | 3339 | |
| cag cag cag act cgc ctc aag gag ctg gag tcc cag gtg tcg ggt<br>Gln Gln Gln Thr Arg Leu Lys Glu Leu Glu Ser Gln Val Ser Gly<br>1115                        1120                        1125 | 3384 | |
| ctg gag aag gag gcc atc gag ctc agg gag gcc gtc gag cag cag<br>Leu Glu Lys Glu Ala Ile Glu Leu Arg Glu Ala Val Glu Gln Gln<br>1130                        1135                        1140 | 3429 | |
| aaa gtg aag aac aat gac ctc cgg gag aag aac tgg aag gcc atg<br>Lys Val Lys Asn Asn Asp Leu Arg Glu Lys Asn Trp Lys Ala Met<br>1145                        1150                        1155 | 3474 | |
| gag gca ctg gcc acg gcc gag cag gcc tgc aag gag aag ctg cac<br>Glu Ala Leu Ala Thr Ala Glu Gln Ala Cys Lys Glu Lys Leu His<br>1160                        1165                        1170 | 3519 | |
| tcc ctg acc cag gcc aag gag gaa tcg gag aag cag ctc tgt ctg<br>Ser Leu Thr Gln Ala Lys Glu Glu Ser Glu Lys Gln Leu Cys Leu<br>1175                        1180                        1185 | 3564 | |
| att gag gcg cag acc atg gag gcc ctg ctg gct ctg ctc cca gaa<br>Ile Glu Ala Gln Thr Met Glu Ala Leu Leu Ala Leu Leu Pro Glu<br>1190                        1195                        1200 | 3609 | |
| ctc tct gtc ttg gca caa cag aat tac acc gag tgg ctg cag gat<br>Leu Ser Val Leu Ala Gln Gln Asn Tyr Thr Glu Trp Leu Gln Asp<br>1205                        1210                        1215 | 3654 | |
| ctc aaa gag aaa ggc ccc acg ctg ctg aag cac ccg cca gct ccc<br>Leu Lys Glu Lys Gly Pro Thr Leu Leu Lys His Pro Pro Ala Pro<br>1220                        1225                        1230 | 3699 | |
| gcg gag cct tcc tcg gac ctg gcc tcc aag ttg agg gag gcc gag<br>Ala Glu Pro Ser Ser Asp Leu Ala Ser Lys Leu Arg Glu Ala Glu<br>1235                        1240                        1245 | 3744 | |
| gag acg cag agc aca ctg cag gcc gag tgt gac cag tac cgc agc<br>Glu Thr Gln Ser Thr Leu Gln Ala Glu Cys Asp Gln Tyr Arg Ser<br>1250                        1255                        1260 | 3789 | |
| atc ctg gcg gag acg gag ggc atg ctc aga gac ctg cag aag agc<br>Ile Leu Ala Glu Thr Glu Gly Met Leu Arg Asp Leu Gln Lys Ser<br>1265                        1270                        1275 | 3834 | |
| gtg gag gag gag gag cag gtg tgg agg gcc aag gtg ggc gcc gca<br>Val Glu Glu Glu Glu Gln Val Trp Arg Ala Lys Val Gly Ala Ala<br>1280                        1285                        1290 | 3879 | |

```
gag gag gag ctc cag aag tcc cgg gtc aca gtg aag cat ctc gaa      3924
Glu Glu Glu Leu Gln Lys Ser Arg Val Thr Val Lys His Leu Glu
        1295                1300                1305 gag att gta gag aag cta aaa gga gaa ctt gaa agt tcg gac cag      3969
Glu Ile Val Glu Lys Leu Lys Gly Glu Leu Glu Ser Ser Asp Gln
    1310                1315                1320 gtg agg gag cac acg tcg cat ttg gag gca gag ctg gaa aag cac      4014
Val Arg Glu His Thr Ser His Leu Glu Ala Glu Leu Glu Lys His
1325                1330                1335 atg gcg gcc gcc agc gcc gag tgc cag aac tac gcc aag gag gtg      4059
Met Ala Ala Ala Ser Ala Glu Cys Gln Asn Tyr Ala Lys Glu Val
        1340                1345                1350 gca ggg ctg agg caa ctt ctc cta gaa tct caa tct cag ctc gat      4104
Ala Gly Leu Arg Gln Leu Leu Leu Glu Ser Gln Ser Gln Leu Asp
    1355                1360                1365 gcc gcc aag agc gaa gcc cag aaa cag agc gat gag ctt gcc ctg      4149
Ala Ala Lys Ser Glu Ala Gln Lys Gln Ser Asp Glu Leu Ala Leu
1370                1375                1380 gtc agg cag cag ttg agt gaa atg aag agc cac gta gag gat ggt      4194
Val Arg Gln Gln Leu Ser Glu Met Lys Ser His Val Glu Asp Gly
        1385                1390                1395 gac att gct ggg gcc cca gct tcc tcc cca gag gcg ccc cca gcc      4239
Asp Ile Ala Gly Ala Pro Ala Ser Ser Pro Glu Ala Pro Pro Ala
    1400                1405                1410 gag cag gac ccc gtt cag ctg aag acg cag ctg gag tgg aca gaa      4284
Glu Gln Asp Pro Val Gln Leu Lys Thr Gln Leu Glu Trp Thr Glu
1415                1420                1425 gcc atc ctg gag gat gag cag aca cag cgg cag aag ctc acg gcc      4329
Ala Ile Leu Glu Asp Glu Gln Thr Gln Arg Gln Lys Leu Thr Ala
        1430                1435                1440 gag ttt gag gag gct cag acc tcg gca tgt cgg tta caa gaa gaa      4374
Glu Phe Glu Glu Ala Gln Thr Ser Ala Cys Arg Leu Gln Glu Glu
    1445                1450                1455 ttg gag aag ctc cgc aca gcc ggc ccc cta gag tct tca gaa aca      4419
Leu Glu Lys Leu Arg Thr Ala Gly Pro Leu Glu Ser Ser Glu Thr
1460                1465                1470 gag gag gcc tca cag ctg aag gag aga cta gaa aaa gag aag aag      4464
Glu Glu Ala Ser Gln Leu Lys Glu Arg Leu Glu Lys Glu Lys Lys
        1475                1480                1485 tta aca agt gac ctg ggg cgc gcc gcc acg aga ctg cag gag ctt      4509
Leu Thr Ser Asp Leu Gly Arg Ala Ala Thr Arg Leu Gln Glu Leu
    1490                1495                1500 ctg aag acg acc cag gag cag ctg gca agg gag aag gac acg gtg      4554
Leu Lys Thr Thr Gln Glu Gln Leu Ala Arg Glu Lys Asp Thr Val
1505                1510                1515 aag aag ctg cag gaa cag ctg gaa aag gca gag gac ggc agc agc      4599
Lys Lys Leu Gln Glu Gln Leu Glu Lys Ala Glu Asp Gly Ser Ser
        1520                1525                1530 tca aag gag ggc acc tct gtc tga                                  4623
Ser Lys Glu Gly Thr Ser Val
    1535                1540

<210> SEQ ID NO 2
<211> LENGTH: 1540
<212> TYPE: PRT
<213> ORGANISM: Homo sapiens
```

-continued

```
<400> SEQUENCE: 2

Met Asp Ile Tyr Asp Thr Gln Thr Leu Gly Val Val Phe Gly Gly
1               5                   10                  15

Phe Met Val Val Ser Ala Ile Gly Ile Phe Leu Val Ser Thr Phe Ser
            20                  25                  30

Met Lys Glu Thr Ser Tyr Glu Glu Ala Leu Ala Asn Gln Arg Lys Glu
        35                  40                  45

Met Ala Lys Thr His His Gln Lys Val Glu Lys Lys Lys Glu Lys
    50                  55                  60

Thr Val Glu Lys Lys Gly Lys Thr Lys Lys Glu Glu Lys Pro Asn
65                  70                  75                  80

Gly Lys Ile Pro Asp His Asp Pro Ala Pro Asn Val Thr Val Leu Leu
                85                  90                  95

Arg Glu Pro Val Arg Ala Pro Ala Val Ala Val Ala Pro Thr Pro Val
                100                 105                 110

Gln Pro Pro Ile Ile Val Ala Pro Val Ala Thr Val Pro Ala Met Pro
            115                 120                 125

Gln Glu Lys Leu Ala Ser Ser Pro Lys Asp Lys Lys Lys Glu Lys
    130                 135                 140

Lys Val Ala Lys Val Glu Pro Ala Val Ser Ser Val Val Asn Ser Ile
145                 150                 155                 160

Gln Val Leu Thr Ser Lys Ala Ala Ile Leu Glu Thr Ala Pro Lys Glu
                165                 170                 175

Val Pro Met Val Val Val Pro Val Gly Ala Lys Gly Asn Thr Pro
                180                 185                 190

Ala Thr Gly Thr Thr Gln Gly Lys Lys Ala Glu Gly Thr Gln Asn Gln
            195                 200                 205

Ser Lys Lys Ala Glu Gly Ala Pro Asn Gln Gly Arg Lys Ala Glu Gly
    210                 215                 220

Thr Pro Asn Gln Gly Lys Lys Thr Glu Gly Thr Pro Asn Gln Gly Lys
225                 230                 235                 240

Lys Ala Glu Gly Thr Pro Asn Gln Gly Lys Lys Ala Glu Gly Thr Pro
                245                 250                 255

Asn Gln Gly Lys Lys Ala Glu Gly Ala Gln Asn Gln Gly Lys Lys Val
                260                 265                 270

Asp Thr Thr Pro Asn Gln Gly Lys Lys Val Glu Gly Ala Pro Thr Gln
            275                 280                 285

Gly Arg Lys Ala Glu Gly Ala Gln Asn Gln Ala Lys Lys Val Glu Gly
        290                 295                 300

Ala Gln Asn Gln Gly Lys Lys Ala Glu Gly Ala Gln Asn Gln Gly Lys
305                 310                 315                 320

Lys Gly Glu Gly Ala Gln Asn Gln Gly Lys Lys Ala Glu Gly Ala Gln
                325                 330                 335

Asn Gln Gly Lys Lys Ala Glu Gly Ala Gln Asn Gln Gly Lys Lys Ala
            340                 345                 350

Glu Gly Ala Gln Asn Gln Gly Lys Lys Ala Glu Gly Ala Gln Asn Gln
        355                 360                 365

Gly Lys Lys Ala Glu Gly Ala Gln Asn Gln Gly Lys Lys Ala Glu Gly
    370                 375                 380

Ala Gln Asn Gln Gly Lys Lys Val Glu Gly Ala Gln Asn Gln Gly Lys
385                 390                 395                 400

Lys Ala Glu Gly Ala Gln Asn Gln Gly Lys Lys Ala Glu Gly Ala Gln
                405                 410                 415
```

```
Asn Gln Gly Lys Lys Ala Glu Gly Ala Gln Asn Gln Gly Lys Lys Ala
            420                 425                 430

Glu Gly Ala Gln Asn Gln Gly Lys Lys Ala Glu Gly Ala Gln Asn Gln
            435                 440                 445

Asp Lys Lys Ala Glu Gly Ala Gln Asn Gln Gly Arg Lys Ala Glu Gly
            450                 455                 460

Ala Gln Asn Gln Gly Arg Lys Ala Glu Gly Ala Gln Asn Gln Gly Lys
465                 470                 475                 480

Lys Ala Glu Gly Ala Gln Asn Gln Gly Lys Lys Ala Glu Gly Thr Pro
                485                 490                 495

Asn Gln Gly Lys Lys Ala Glu Gly Thr Pro Asn Gln Gly Lys Lys Ala
            500                 505                 510

Glu Gly Ala Gln Asn Gln Gly Lys Lys Ala Glu Gly Ala Gln Asn Gln
            515                 520                 525

Gly Lys Lys Ala Glu Gly Thr Pro Asn Gln Gly Lys Lys Ala Glu Gly
            530                 535                 540

Ala Gln Asn Gln Gly Lys Lys Ala Glu Gly Ala Gln Asn Gln Gly Lys
545                 550                 555                 560

Lys Ala Glu Gly Ala Gln Asn Gln Gly Lys Lys Ala Glu Gly Ala Gln
                565                 570                 575

Asn Gln Gly Lys Lys Ala Glu Gly Ala Gln Asn Gln Gly Lys Lys Ala
            580                 585                 590

Glu Gly Ala Gln Asn Gln Gly Lys Lys Val Glu Gly Ala Gln Asn Gln
            595                 600                 605

Gly Lys Lys Ala Glu Gly Ala Gln Asn Gln Gly Lys Lys Ala Glu Gly
            610                 615                 620

Ala Gln Asn Gln Gly Lys Lys Ala Glu Gly Ala Gln Asn Gln Gly Gln
625                 630                 635                 640

Lys Gly Glu Gly Ala Gln Asn Gln Gly Lys Lys Thr Glu Gly Ala Gln
                645                 650                 655

Gly Lys Lys Ala Glu Arg Ser Pro Asn Gln Gly Lys Lys Gly Glu Gly
            660                 665                 670

Ala Pro Ile Gln Gly Lys Lys Ala Asp Ser Val Ala Asn Gln Gly Thr
            675                 680                 685

Lys Val Glu Gly Ile Thr Asn Gln Gly Lys Lys Ala Glu Gly Ser Pro
            690                 695                 700

Ser Glu Gly Lys Lys Ala Glu Gly Ser Pro Asn Gln Gly Lys Lys Ala
705                 710                 715                 720

Asp Ala Ala Ala Asn Gln Gly Lys Lys Thr Glu Ser Ala Ser Val Gln
                725                 730                 735

Gly Arg Asn Thr Asp Val Ala Gln Ser Pro Glu Ala Pro Lys Gln Glu
            740                 745                 750

Ala Pro Ala Lys Lys Lys Ser Gly Ser Lys Lys Gly Glu Pro Gly
            755                 760                 765

Pro Pro Asp Ala Asp Gly Pro Leu Tyr Leu Pro Tyr Lys Thr Leu Val
            770                 775                 780

Ser Thr Val Gly Ser Met Val Phe Asn Glu Gly Glu Ala Gln Arg Leu
785                 790                 795                 800

Ile Glu Ile Leu Ser Glu Lys Ala Gly Ile Ile Gln Asp Thr Trp His
                805                 810                 815

Lys Ala Thr Gln Lys Gly Asp Pro Val Ala Ile Leu Lys Arg Gln Leu
            820                 825                 830
```

-continued

```
Glu Glu Lys Glu Lys Leu Leu Ala Thr Glu Gln Glu Asp Ala Ala Val
            835                 840                 845
Ala Lys Ser Lys Leu Arg Glu Leu Asn Lys Glu Met Ala Ala Glu Lys
    850                 855                 860
Ala Lys Ala Ala Ala Gly Glu Ala Lys Val Lys Lys Gln Leu Val Ala
865                 870                 875                 880
Arg Glu Gln Glu Ile Thr Ala Val Gln Ala Arg Met Gln Ala Ser Tyr
                885                 890                 895
Arg Glu His Val Lys Glu Val Gln Leu Gln Gly Lys Ile Arg Thr
            900                 905                 910
Leu Gln Glu Gln Leu Glu Asn Gly Pro Asn Thr Gln Leu Ala Arg Leu
        915                 920                 925
Gln Gln Glu Asn Ser Ile Leu Arg Asp Ala Leu Asn Gln Ala Thr Ser
    930                 935                 940
Gln Val Glu Ser Lys Gln Asn Ala Glu Leu Ala Lys Leu Arg Gln Glu
945                 950                 955                 960
Leu Ser Lys Val Ser Lys Glu Leu Val Glu Lys Ser Glu Ala Val Arg
                965                 970                 975
Gln Asp Glu Gln Gln Arg Lys Ala Leu Glu Ala Lys Ala Ala Ala Phe
            980                 985                 990
Glu Lys Gln Val Leu Gln Leu Gln  Ala Ser His Arg Glu  Ser Glu Glu
        995                 1000                 1005
Ala Leu Gln Lys Arg Leu Asp  Glu Val Ser Arg Glu  Leu Cys His
        1010                 1015                 1020
Thr Gln Ser Ser His Ala Ser  Leu Arg Ala Asp Ala  Glu Lys Ala
        1025                 1030                 1035
Gln Glu Gln Gln Gln Gln Met  Ala Glu Leu His Ser  Lys Leu Gln
        1040                 1045                 1050
Ser Ser Glu Ala Glu Val Arg  Ser Lys Cys Glu Glu  Leu Ser Gly
        1055                 1060                 1065
Leu His Gly Gln Leu Gln Glu  Ala Arg Ala Glu Asn  Ser Gln Leu
        1070                 1075                 1080
Thr Glu Arg Ile Arg Ser Ile  Glu Ala Leu Leu Glu  Ala Gly Gln
        1085                 1090                 1095
Ala Arg Asp Ala Gln Asp Val  Gln Ala Ser Gln Ala  Glu Ala Asp
        1100                 1105                 1110
Gln Gln Gln Thr Arg Leu Lys  Glu Leu Glu Ser Gln  Val Ser Gly
        1115                 1120                 1125
Leu Glu Lys Glu Ala Ile Glu  Leu Arg Glu Ala Val  Glu Gln Gln
        1130                 1135                 1140
Lys Val Lys Asn Asn Asp Leu  Arg Glu Lys Asn Trp  Lys Ala Met
        1145                 1150                 1155
Glu Ala Leu Ala Thr Ala Glu  Gln Ala Cys Lys Glu  Lys Leu His
        1160                 1165                 1170
Ser Leu Thr Gln Ala Lys Glu  Glu Ser Glu Lys Gln  Leu Cys Leu
        1175                 1180                 1185
Ile Glu Ala Gln Thr Met Glu  Ala Leu Leu Ala Leu  Leu Pro Glu
        1190                 1195                 1200
Leu Ser Val Leu Ala Gln Gln  Asn Tyr Thr Glu Trp  Leu Gln Asp
        1205                 1210                 1215
Leu Lys Glu Lys Gly Pro Thr  Leu Leu Lys His Pro  Pro Ala Pro
        1220                 1225                 1230
```

```
Ala Glu Pro Ser Ser Asp Leu Ala Ser Lys Leu Arg Glu Ala Glu
    1235                1240                1245

Glu Thr Gln Ser Thr Leu Gln Ala Glu Cys Asp Gln Tyr Arg Ser
    1250                1255                1260

Ile Leu Ala Glu Thr Glu Gly Met Leu Arg Asp Leu Gln Lys Ser
    1265                1270                1275

Val Glu Glu Glu Gln Val Trp Arg Ala Lys Val Gly Ala Ala
    1280                1285                1290

Glu Glu Leu Gln Lys Ser Arg Val Thr Val Lys His Leu Glu
    1295                1300                1305

Glu Ile Val Glu Lys Leu Lys Gly Glu Leu Glu Ser Ser Asp Gln
    1310                1315                1320

Val Arg Glu His Thr Ser His Leu Glu Ala Glu Leu Glu Lys His
    1325                1330                1335

Met Ala Ala Ala Ser Ala Glu Cys Gln Asn Tyr Ala Lys Glu Val
    1340                1345                1350

Ala Gly Leu Arg Gln Leu Leu Leu Glu Ser Gln Ser Gln Leu Asp
    1355                1360                1365

Ala Ala Lys Ser Glu Ala Gln Lys Gln Ser Asp Glu Leu Ala Leu
    1370                1375                1380

Val Arg Gln Gln Leu Ser Glu Met Lys Ser His Val Glu Asp Gly
    1385                1390                1395

Asp Ile Ala Gly Ala Pro Ala Ser Ser Pro Glu Ala Pro Pro Ala
    1400                1405                1410

Glu Gln Asp Pro Val Gln Leu Lys Thr Gln Leu Glu Trp Thr Glu
    1415                1420                1425

Ala Ile Leu Glu Asp Glu Gln Thr Gln Arg Gln Lys Leu Thr Ala
    1430                1435                1440

Glu Phe Glu Glu Ala Gln Thr Ser Ala Cys Arg Leu Gln Glu Glu
    1445                1450                1455

Leu Glu Lys Leu Arg Thr Ala Gly Pro Leu Glu Ser Ser Glu Thr
    1460                1465                1470

Glu Glu Ala Ser Gln Leu Lys Glu Arg Leu Glu Lys Glu Lys Lys
    1475                1480                1485

Leu Thr Ser Asp Leu Gly Arg Ala Ala Thr Arg Leu Gln Glu Leu
    1490                1495                1500

Leu Lys Thr Thr Gln Glu Gln Leu Ala Arg Glu Lys Asp Thr Val
    1505                1510                1515

Lys Lys Leu Gln Glu Gln Leu Glu Lys Ala Glu Asp Gly Ser Ser
    1520                1525                1530

Ser Lys Glu Gly Thr Ser Val
    1535                1540

<210> SEQ ID NO 3
<211> LENGTH: 1275
<212> TYPE: DNA
<213> ORGANISM: Homo sapiens
<220> FEATURE:
<221> NAME/KEY: CDS
<222> LOCATION: (1)..(1275)

<400> SEQUENCE: 3 atg gct gcc ggg ccg atc tcc gag cgg aat cag gat gcc act gtg tac   48
Met Ala Ala Gly Pro Ile Ser Glu Arg Asn Gln Asp Ala Thr Val Tyr
1               5                   10                  15
```

-continued

| | | |
|---|---|---|
| gtg ggg ggc ctg gat gag aag gtt agt gaa ccg ctg ctg tgg gaa ctg<br>Val Gly Gly Leu Asp Glu Lys Val Ser Glu Pro Leu Leu Trp Glu Leu<br>20              25                  30 | 96 |
| ttt ctc cag gct gga cca gta gtc aac acc cac atg cca aag gat aga<br>Phe Leu Gln Ala Gly Pro Val Val Asn Thr His Met Pro Lys Asp Arg<br>35              40                  45 | 144 |
| gtc act ggc cag cac caa ggc tat ggc ttt gtg gaa ttc ttg agt gag<br>Val Thr Gly Gln His Gln Gly Tyr Gly Phe Val Glu Phe Leu Ser Glu<br>50              55                  60 | 192 |
| gaa gat gct gac tat gcc att aag atc atg aac atg atc aaa ctc tat<br>Glu Asp Ala Asp Tyr Ala Ile Lys Ile Met Asn Met Ile Lys Leu Tyr<br>65          70                  75              80 | 240 |
| ggg aag cca ata cgg gtg aac aaa gca tca gct cac aaa aac ctg<br>Gly Lys Pro Ile Arg Val Asn Lys Ala Ser Ala His Asn Lys Asn Leu<br>85              90                  95 | 288 |
| gat gta ggg gcc aac att ttc att ggg aac ctg gac cct gag att gat<br>Asp Val Gly Ala Asn Ile Phe Ile Gly Asn Leu Asp Pro Glu Ile Asp<br>100              105                  110 | 336 |
| gag aag ttg ctt tat gat act ttc agc gcc ttt ggg gtc atc tta caa<br>Glu Lys Leu Leu Tyr Asp Thr Phe Ser Ala Phe Gly Val Ile Leu Gln<br>115              120                  125 | 384 |
| acc ccc aaa att atg cgg gac cct gac aca ggc aac tcc aaa ggt tat<br>Thr Pro Lys Ile Met Arg Asp Pro Asp Thr Gly Asn Ser Lys Gly Tyr<br>130              135                  140 | 432 |
| gcc ttt att aat ttt gct tca ttt gat gct tcg gat gca gca att gaa<br>Ala Phe Ile Asn Phe Ala Ser Phe Asp Ala Ser Asp Ala Ala Ile Glu<br>145              150                  155              160 | 480 |
| gcc atg aat ggg cag tac ctc tgt aac cgt cct atc acc gta tct tat<br>Ala Met Asn Gly Gln Tyr Leu Cys Asn Arg Pro Ile Thr Val Ser Tyr<br>165              170                  175 | 528 |
| gcc ttc aag aag gac tcc aag ggt gag cgc cat ggc tca gca gcc gaa<br>Ala Phe Lys Lys Asp Ser Lys Gly Glu Arg His Gly Ser Ala Ala Glu<br>180              185                  190 | 576 |
| cga ctt ctg gca gct cag aac ccg ctc tcc cag gct gat cgc cct cat<br>Arg Leu Leu Ala Ala Gln Asn Pro Leu Ser Gln Ala Asp Arg Pro His<br>195              200                  205 | 624 |
| cag ctg ttt gca gat gca cct cct cca ccc tct gct ccc aat cct gtg<br>Gln Leu Phe Ala Asp Ala Pro Pro Pro Pro Ser Ala Pro Asn Pro Val<br>210              215                  220 | 672 |
| gta tca tca ttg ggg tct ggg ctt cct cca cca ggc atg cct cct cct<br>Val Ser Ser Leu Gly Ser Gly Leu Pro Pro Pro Gly Met Pro Pro Pro<br>225              230                  235              240 | 720 |
| ggc tcc ttc cca ccc cca gtg cca cct cct gga gcc ctc cca cct ggg<br>Gly Ser Phe Pro Pro Pro Val Pro Pro Pro Gly Ala Leu Pro Pro Gly<br>245              250                  255 | 768 |
| ata ccc cca gcc atg ccc cca cct atg cct cct ggg gct gca gga<br>Ile Pro Pro Ala Met Pro Pro Pro Met Pro Pro Gly Ala Ala Gly<br>260              265                  270 | 816 |
| cat ggc ccc cca tcg gca gga acc cca ggg gca gga cat cct ggt cat<br>His Gly Pro Pro Ser Ala Gly Thr Pro Gly Ala Gly His Pro Gly His<br>275              280                  285 | 864 |
| gga cac tca cat cct cac cca ttc cca ccg ggt ggg atg ccc cat cca<br>Gly His Ser His Pro His Pro Phe Pro Pro Gly Gly Met Pro His Pro<br>290              295                  300 | 912 |
| ggg atg tct cag atg cag ctt gca cac cat ggc cct cat ggc tta gga<br>Gly Met Ser Gln Met Gln Leu Ala His His Gly Pro His Gly Leu Gly<br>305              310                  315              320 | 960 |
| cat ccc cac gct gga ccc cca ggc tct ggg ggc cag cca ccg ccc cga<br>His Pro His Ala Gly Pro Pro Gly Ser Gly Gly Gln Pro Pro Pro Arg<br>325              330                  335 | 1008 |

| | | | | | | | | | | | | |
|---|---|---|---|---|---|---|---|---|---|---|---|---|
| cca | cca | cct | gga | atg | cct | cat | cct | gga | cct | cct | cca | atg | ggc | atg | ccc | 1056 |
| Pro | Pro | Pro | Gly | Met | Pro | His | Pro | Gly | Pro | Pro | Pro | Met | Gly | Met | Pro | |
| | | | 340 | | | | | 345 | | | | | 350 | | | |

| ccc | cga | ggg | cct | cca | ttc | gga | tct | ccc | atg | ggt | cac | cca | ggt | cct | atg | 1104 |
|---|---|---|---|---|---|---|---|---|---|---|---|---|---|---|---|---|
| Pro | Arg | Gly | Pro | Pro | Phe | Gly | Ser | Pro | Met | Gly | His | Pro | Gly | Pro | Met | |
| | | 355 | | | | | 360 | | | | | 365 | | | | |

| cct | ccg | cat | ggt | atg | cgt | gga | cct | cct | cca | ctg | atg | ccc | ccc | cat | gga | 1152 |
|---|---|---|---|---|---|---|---|---|---|---|---|---|---|---|---|---|
| Pro | Pro | His | Gly | Met | Arg | Gly | Pro | Pro | Pro | Leu | Met | Pro | Pro | His | Gly | |
| | 370 | | | | | 375 | | | | | 380 | | | | | |

| tac | act | ggc | cct | cca | cga | ccc | cca | ccc | tat | ggc | tac | cag | cgg | ggg | cct | 1200 |
|---|---|---|---|---|---|---|---|---|---|---|---|---|---|---|---|---|
| Tyr | Thr | Gly | Pro | Pro | Arg | Pro | Pro | Pro | Tyr | Gly | Tyr | Gln | Arg | Gly | Pro | |
| 385 | | | | | 390 | | | | | 395 | | | | | 400 | |

| ctc | cct | cca | ccc | aga | ccc | act | ccc | cgg | cca | cca | gtt | ccc | cct | cga | ggc | 1248 |
|---|---|---|---|---|---|---|---|---|---|---|---|---|---|---|---|---|
| Leu | Pro | Pro | Pro | Arg | Pro | Thr | Pro | Arg | Pro | Pro | Val | Pro | Pro | Arg | Gly | |
| | | | | 405 | | | | | 410 | | | | | 415 | | |

| cca | ctt | cga | ggc | cct | ctc | cct | cag | taa | | | | | | | | 1275 |
|---|---|---|---|---|---|---|---|---|---|---|---|---|---|---|---|---|
| Pro | Leu | Arg | Gly | Pro | Leu | Pro | Gln | | | | | | | | | |
| | | | 420 | | | | | | | | | | | | | |

<210> SEQ ID NO 4
<211> LENGTH: 424
<212> TYPE: PRT
<213> ORGANISM: Homo sapiens

<400> SEQUENCE: 4

Met Ala Ala Gly Pro Ile Ser Glu Arg Asn Gln Asp Ala Thr Val Tyr
1               5                   10                  15

Val Gly Gly Leu Asp Glu Lys Val Ser Glu Pro Leu Leu Trp Glu Leu
            20                  25                  30

Phe Leu Gln Ala Gly Pro Val Val Asn Thr His Met Pro Lys Asp Arg
        35                  40                  45

Val Thr Gly Gln His Gln Gly Tyr Gly Phe Val Glu Phe Leu Ser Glu
    50                  55                  60

Glu Asp Ala Asp Tyr Ala Ile Lys Ile Met Asn Met Ile Lys Leu Tyr
65                  70                  75                  80

Gly Lys Pro Ile Arg Val Asn Lys Ala Ser Ala His Asn Lys Asn Leu
                85                  90                  95

Asp Val Gly Ala Asn Ile Phe Ile Gly Asn Leu Asp Pro Glu Ile Asp
            100                 105                 110

Glu Lys Leu Leu Tyr Asp Thr Phe Ser Ala Phe Gly Val Ile Leu Gln
        115                 120                 125

Thr Pro Lys Ile Met Arg Asp Pro Asp Thr Gly Asn Ser Lys Gly Tyr
    130                 135                 140

Ala Phe Ile Asn Phe Ala Ser Phe Asp Ala Ser Asp Ala Ala Ile Glu
145                 150                 155                 160

Ala Met Asn Gly Gln Tyr Leu Cys Asn Arg Pro Ile Thr Val Ser Tyr
                165                 170                 175

Ala Phe Lys Lys Asp Ser Lys Gly Glu Arg His Gly Ser Ala Ala Glu
            180                 185                 190

Arg Leu Leu Ala Ala Gln Asn Pro Leu Ser Gln Ala Asp Arg Pro His
        195                 200                 205

Gln Leu Phe Ala Asp Ala Pro Pro Pro Ser Ala Pro Asn Pro Val
    210                 215                 220

Val Ser Ser Leu Gly Ser Gly Leu Pro Pro Gly Met Pro Pro
225                 230                 235                 240

Gly Ser Phe Pro Pro Val Pro Pro Gly Ala Leu Pro Pro Gly
                245                 250                 255

Ile Pro Pro Ala Met Pro Pro Met Pro Gly Ala Ala Gly
            260             265             270

His Gly Pro Pro Ser Ala Gly Thr Pro Ala Gly His Pro Gly His
        275                 280                 285

Gly His Ser His Pro His Pro Phe Pro Pro Gly Met Pro His Pro
    290                 295                 300

Gly Met Ser Gln Met Gln Leu Ala His His Gly Pro His Gly Leu Gly
305                 310                 315                 320

His Pro His Ala Gly Pro Pro Gly Ser Gly Gly Gln Pro Pro Arg
                325                 330                 335

Pro Pro Pro Gly Met Pro His Pro Gly Pro Pro Met Gly Met Pro
            340                 345                 350

Pro Arg Gly Pro Pro Phe Gly Ser Pro Met Gly His Pro Gly Pro Met
        355                 360                 365

Pro Pro His Gly Met Arg Gly Pro Pro Leu Met Pro Pro His Gly
    370                 375                 380

Tyr Thr Gly Pro Pro Arg Pro Pro Tyr Gly Tyr Gln Arg Gly Pro
385                 390                 395                 400

Leu Pro Pro Pro Arg Pro Thr Pro Arg Pro Pro Val Pro Arg Gly
                405                 410                 415

Pro Leu Arg Gly Pro Leu Pro Gln
            420

<210> SEQ ID NO 5
<211> LENGTH: 126
<212> TYPE: DNA
<213> ORGANISM: Homo sapiens

<400> SEQUENCE: 5
tcgtcggagc agacgggagt ttctcctcgg ggtcggagca ggaggcacgc ggagtgtgag      60
gccacgcatg agcggacgct aaccccctcc ccagccacaa agagtctaca tgtctagggt    120
ctagac                                                               126

<210> SEQ ID NO 6
<211> LENGTH: 266
<212> TYPE: DNA
<213> ORGANISM: Homo sapiens

<400> SEQUENCE: 6
gcccgcgccg gctgtgctgc acagggggag gagagggaac cccaggcgcg agcgggaaga      60
ggggacctgc agccacaact tctctggtcc tctgcatccc ttctgtccct ccacccgtcc    120
ccttccccac cctctggccc ccaccttctt ggaggcgaca accccggga ggcattagaa     180 gggatttttc ccgcaggttg cgaagggaag caaacttggt ggcaacttgc ctcccggtgc    240
gggcgtctct cccccaccgt ctcaac                                         266

<210> SEQ ID NO 7
<211> LENGTH: 27
<212> TYPE: DNA
<213> ORGANISM: Homo sapiens

<400> SEQUENCE: 7
tcgtcggagc agacgggagt ttctcct                                         27

```
<210> SEQ ID NO 8
<211> LENGTH: 32
<212> TYPE: DNA
<213> ORGANISM: Homo sapiens

<400> SEQUENCE: 8
ccaccttctt ggaggcgaca accccggga gg                              32

<210> SEQ ID NO 9
<211> LENGTH: 33
<212> TYPE: DNA
<213> ORGANISM: Artificial Sequence
<220> FEATURE:
<223> OTHER INFORMATION: A primer for amplifying the portion of cis-
      element of cis-element #3.

<400> SEQUENCE: 9
gatcttcgtc ggagcagacg ggagtttctc cta                            33

<210> SEQ ID NO 10
<211> LENGTH: 33
<212> TYPE: DNA
<213> ORGANISM: Artificial Sequence
<220> FEATURE:
<223> OTHER INFORMATION: A primer for amplifying the portion of cis-
      element of cis-element #3.

<400> SEQUENCE: 10
agcttaggag aaactcccgt ctgctccgac gaa                            33

<210> SEQ ID NO 11
<211> LENGTH: 30
<212> TYPE: DNA
<213> ORGANISM: Artificial Sequence
<220> FEATURE:
<223> OTHER INFORMATION: A primer for amplifying the portion of cis-
      element of cis-element #4.

<400> SEQUENCE: 11
gatcttctgc atcccttctg tccctccaca                                30

<210> SEQ ID NO 12
<211> LENGTH: 30
<212> TYPE: DNA
<213> ORGANISM: Artificial Sequence
<220> FEATURE:
<223> OTHER INFORMATION: A primer for amplifying the portion of cis-
      element of cis-element #4.

<400> SEQUENCE: 12
agcttgtgga gggacagaag ggatgcagaa                                30

<210> SEQ ID NO 13
<211> LENGTH: 27
<212> TYPE: DNA
<213> ORGANISM: Artificial Sequence
<220> FEATURE:
<223> OTHER INFORMATION: A primer for amplifying the portion of cis-
      element of cis-element #2.

<400> SEQUENCE: 13
aaaaaaagat ctgcccgcgc cggctgt                                   27

<210> SEQ ID NO 14
<211> LENGTH: 29
<212> TYPE: DNA
<213> ORGANISM: Artificial Sequence
```

```
<220> FEATURE:
<223> OTHER INFORMATION: A primer for amplifying the portion of cis-
      element of cis-element #2.

<400> SEQUENCE: 14
aaaaaaaagc ttgttgagac ggtgggga                                      29

<210> SEQ ID NO 15
<211> LENGTH: 27
<212> TYPE: DNA
<213> ORGANISM: Artificial Sequence
<220> FEATURE:
<223> OTHER INFORMATION: A primer for amplifying the portion of cis-
      element of cis-element #1.

<400> SEQUENCE: 15
aaaaaaagat cttcgtcgga gcagacg                                       27

<210> SEQ ID NO 16
<211> LENGTH: 27
<212> TYPE: DNA
<213> ORGANISM: Artificial Sequence
<220> FEATURE:
<223> OTHER INFORMATION: A primer for amplifying the portion of cis-
      element of cis-element #1.

<400> SEQUENCE: 16 aaaaaaagc ttgtctagac cctagac                                        27

<210> SEQ ID NO 17
<211> LENGTH: 9
<212> TYPE: DNA
<213> ORGANISM: Homo sapiens
<220> FEATURE:
<221> NAME/KEY: misc_feature
<222> LOCATION: (4)..(6)
<223> OTHER INFORMATION: "n" is a, c, g, or t
<220> FEATURE:
<221> NAME/KEY: misc_feature
<222> LOCATION: (9)..(9)
<223> OTHER INFORMATION: "v" is a or g or c.

<400> SEQUENCE: 17 gagnnnacv                                                            9

<210> SEQ ID NO 18
<211> LENGTH: 10
<212> TYPE: DNA
<213> ORGANISM: Homo sapiens
<220> FEATURE:
<221> NAME/KEY: misc_feature
<222> LOCATION: (4)..(7)
<223> OTHER INFORMATION: "n" is a, c, g, or t
<220> FEATURE:
<221> NAME/KEY: misc_feature
<222> LOCATION: (10)..(10)
<223> OTHER INFORMATION: "v" is a or g or c.

<400> SEQUENCE: 18 gagnnnnacv                                                          10

<210> SEQ ID NO 19
<211> LENGTH: 11
<212> TYPE: DNA
<213> ORGANISM: Homo sapiens
<220> FEATURE:
<221> NAME/KEY: misc_feature
<222> LOCATION: (4)..(8)
<223> OTHER INFORMATION: "n" is a, c, g, or t
```

```
<220> FEATURE:
<221> NAME/KEY: misc_feature
<222> LOCATION: (11)..(11)
<223> OTHER INFORMATION: "v" is a or g or c.

<400> SEQUENCE: 19
gagnnnnnac v                                                              11

<210> SEQ ID NO 20
<211> LENGTH: 12
<212> TYPE: DNA
<213> ORGANISM: Homo sapiens
<220> FEATURE:
<221> NAME/KEY: misc_feature
<222> LOCATION: (4)..(9)
<223> OTHER INFORMATION: "n" is a, c, g, or t
<220> FEATURE:
<221> NAME/KEY: misc_feature
<222> LOCATION: (12)..(12)
<223> OTHER INFORMATION: "r" is a or g
<220> FEATURE:
<221> NAME/KEY: misc_feature
<222> LOCATION: (12)..(12)
<223> OTHER INFORMATION: "v" is a or g or c.

<400> SEQUENCE: 20
gagnnnnnna cv                                                             12

<210> SEQ ID NO 21
<211> LENGTH: 60
<212> TYPE: DNA
<213> ORGANISM: Homo sapiens

<400> SEQUENCE: 21
tcgtcggagc agacgggagt ttctcctcgg ggtcggagca ggaggcacgc ggagtgtgag          60

<210> SEQ ID NO 22
<211> LENGTH: 66
<212> TYPE: DNA
<213> ORGANISM: Homo sapiens

<400> SEQUENCE: 22
gccacgcatg agcggacgct aaccccctcc ccagccacaa agagtctaca tgtctagggt          60
ctagac                                                                    66

<210> SEQ ID NO 23
<211> LENGTH: 181
<212> TYPE: DNA
<213> ORGANISM: Homo sapiens

<400> SEQUENCE: 23
aacgggcgcc gcggcgggga gaagacgcag agcgctgctg ggctgccggg tctcccgctt         60 cccctcctg ctccaagggc ctcctgcatg agggcgcggt agagaccccgg acccgcgccg        120 tgctcctgcc gtttcgctgc gctccgcccg ggcccggctc agccaggccc cgcggtgagc        180
c                                                                       181

<210> SEQ ID NO 24
<211> LENGTH: 30
<212> TYPE: DNA
<213> ORGANISM: Homo sapiens

<400> SEQUENCE: 24 caggggagg agagggaacc ccaggcgcga                                           30
```

```
<210> SEQ ID NO 25
<211> LENGTH: 32
<212> TYPE: DNA
<213> ORGANISM: Homo sapiens

<400> SEQUENCE: 25
gagcgggaag aggggacctg cagccacaac tt                              32

<210> SEQ ID NO 26
<211> LENGTH: 60
<212> TYPE: DNA
<213> ORGANISM: Homo sapiens

<400> SEQUENCE: 26 caggggagg agagggaacc ccaggcgcga gcgggaagag gggacctgca gccacaactt  60

<210> SEQ ID NO 27
<211> LENGTH: 113
<212> TYPE: DNA
<213> ORGANISM: Homo sapiens

<400> SEQUENCE: 27
tcgtcggagc agacgggagt ttctcctcgg ggtcggagca ggaggcacgc ggagtgtgag  60
gccacgcatg agcggacgct aaccccctcc ccagccacaa agagtctaca tgt         113

<210> SEQ ID NO 28
<211> LENGTH: 32
<212> TYPE: DNA
<213> ORGANISM: Artificial Sequence
<220> FEATURE:
<223> OTHER INFORMATION: A primer for amplifying the portion of cis-
      element of cis-element #5.

<400> SEQUENCE: 28
aaaaaaagat cttcgtcgga gcagacggga gt                              32

<210> SEQ ID NO 29
<211> LENGTH: 32
<212> TYPE: DNA
<213> ORGANISM: Artificial Sequence
<220> FEATURE:
<223> OTHER INFORMATION: A primer for amplifying the portion of cis-
      element of cis-element #5.

<400> SEQUENCE: 29
aaaaaaaagc ttctcacact ccgcgtgcct cc                              32

<210> SEQ ID NO 30
<211> LENGTH: 32
<212> TYPE: DNA
<213> ORGANISM: Artificial Sequence
<220> FEATURE:
<223> OTHER INFORMATION: A primer for amplifying the portion of cis-
      element of cis-element #6.

<400> SEQUENCE: 30
aaaaaaagat ctgccacgca tgagcggacg ct                              32

<210> SEQ ID NO 31
<211> LENGTH: 32
<212> TYPE: DNA
<213> ORGANISM: Artificial Sequence
<220> FEATURE:
<223> OTHER INFORMATION: A primer for amplifying the portion of cis-
      element of cis-element #6.
```

```
<400> SEQUENCE: 31
aaaaaaaagc ttgtctagac cctagacatg ta                                32

<210> SEQ ID NO 32
<211> LENGTH: 36
<212> TYPE: DNA
<213> ORGANISM: Artificial Sequence
<220> FEATURE:
<223> OTHER INFORMATION: A primer for amplifying the portion of cis-
      element of cis-element #8.

<400> SEQUENCE: 32
gatctcaggg ggaggagagg gaacccagg cgcgaa                             36

<210> SEQ ID NO 33
<211> LENGTH: 36
<212> TYPE: DNA
<213> ORGANISM: Artificial Sequence
<220> FEATURE:
<223> OTHER INFORMATION: A primer for amplifying the portion of cis-
      element of cis-element #8.

<400> SEQUENCE: 33
agctttcgcg cctggggttc cctctcctcc ccctga                            36

<210> SEQ ID NO 34
<211> LENGTH: 38
<212> TYPE: DNA
<213> ORGANISM: Artificial Sequence
<220> FEATURE:
<223> OTHER INFORMATION: A primer for amplifying the portion of cis-
      element of cis-element #9.

<400> SEQUENCE: 34
gatctgagcg ggaagagggg acctgcagcc acaactta                          38

<210> SEQ ID NO 35
<211> LENGTH: 38
<212> TYPE: DNA
<213> ORGANISM: Artificial Sequence
<220> FEATURE:
<223> OTHER INFORMATION: A primer for amplifying the portion of cis-
      element of cis-element #9.

<400> SEQUENCE: 35
agcttaagtt gtggctgcag gtccctctt cccgctca                           38

<210> SEQ ID NO 36
<211> LENGTH: 66
<212> TYPE: DNA
<213> ORGANISM: Artificial Sequence
<220> FEATURE:
<223> OTHER INFORMATION: A primer for amplifying the portion of cis-
      element of cis-element #10.

<400> SEQUENCE: 36
gatctcaggg ggaggagagg gaacccagg cgcgagcggg aagagggac ctgcagccac    60 aactta                                                             66

<210> SEQ ID NO 37
<211> LENGTH: 66
<212> TYPE: DNA
<213> ORGANISM: Artificial Sequence
<220> FEATURE:
<223> OTHER INFORMATION: A primer for amplifying the portion of cis-
      element of cis-element #10.
```

<400> SEQUENCE: 37
agcttaagtt gtggctgcag gtcccctctt cccgctcgcg cctggggttc cctctcctcc    60
ccctga    66

<210> SEQ ID NO 38
<211> LENGTH: 32
<212> TYPE: DNA
<213> ORGANISM: Artificial Sequence
<220> FEATURE:
<223> OTHER INFORMATION: A primer for amplifying the portion of cis-
      element of cis-element #11.

<400> SEQUENCE: 38
aaaaaaagat cttcgtcgga gcagacggga gt    32

<210> SEQ ID NO 39
<211> LENGTH: 32
<212> TYPE: DNA
<213> ORGANISM: Artificial Sequence
<220> FEATURE:
<223> OTHER INFORMATION: A primer for amplifying the portion of cis-
      element of cis-element #11.

<400> SEQUENCE: 39
aaaaaaaagc ttacatgtag actctttgtg gc    32

<210> SEQ ID NO 40
<211> LENGTH: 25
<212> TYPE: DNA
<213> ORGANISM: Artificial Sequence
<220> FEATURE:
<223> OTHER INFORMATION: example of the motif in a cis-element

<400> SEQUENCE: 40
tcgtcggagg acgggagttt ctcct    25

<210> SEQ ID NO 41
<211> LENGTH: 26
<212> TYPE: DNA
<213> ORGANISM: Artificial Sequence
<220> FEATURE:
<223> OTHER INFORMATION: example of the motif in a cis-element

<400> SEQUENCE: 41
tcgtcggaga gacgggagtt tctcct    26

<210> SEQ ID NO 42
<211> LENGTH: 28
<212> TYPE: DNA
<213> ORGANISM: Artificial Sequence
<220> FEATURE:
<223> OTHER INFORMATION: example of the motif in a cis-element

<400> SEQUENCE: 42
tcgtcggagc agaacgggag tttctcct    28

<210> SEQ ID NO 43
<211> LENGTH: 29
<212> TYPE: DNA
<213> ORGANISM: Artificial Sequence
<220> FEATURE:
<223> OTHER INFORMATION: example of the motif in a cis-element

<400> SEQUENCE: 43
tcgtcggagc agaaacggga gtttctcct    29

```
-continued

<210> SEQ ID NO 44
<211> LENGTH: 30
<212> TYPE: DNA
<213> ORGANISM: Artificial Sequence
<220> FEATURE:
<223> OTHER INFORMATION: example of the motif in a cis-element

<400> SEQUENCE: 44
tcgtcggagc agaaaacggg agtttctcct                                    30

<210> SEQ ID NO 45
<211> LENGTH: 31
<212> TYPE: DNA
<213> ORGANISM: Artificial Sequence
<220> FEATURE:
<223> OTHER INFORMATION: example of the motif in a cis-element

<400> SEQUENCE: 45
tcgtcggagc agaaaaacgg gagtttctcc t                                  31

<210> SEQ ID NO 46
<211> LENGTH: 32
<212> TYPE: DNA
<213> ORGANISM: Artificial Sequence
<220> FEATURE:
<223> OTHER INFORMATION: example of the motif in a cis-element

<400> SEQUENCE: 46
tcgtcggagc agaaaaaacg ggagtttctc ct                                 32

<210> SEQ ID NO 47
<211> LENGTH: 33
<212> TYPE: DNA
<213> ORGANISM: Artificial Sequence
<220> FEATURE:
<223> OTHER INFORMATION: example of the motif in a cis-element

<400> SEQUENCE: 47
tcgtcggagc agaaaaaaac gggagtttct cct                                33

<210> SEQ ID NO 48
<211> LENGTH: 12
<212> TYPE: DNA
<213> ORGANISM: Artificial Sequence
<220> FEATURE:
<223> OTHER INFORMATION: example of the motif in a cis-element

<400> SEQUENCE: 48
ggagtttctc ct                                                       12
```